US008865429B2

(12) United States Patent

Hong et al.

(10) Patent No.: US 8,865,429 B2

(45) Date of Patent: Oct. 21, 2014

(54) INCREASED OIL CONTENT BY INCREASING YAP1 TRANSCRIPTION FACTOR ACTIVITY IN OLEAGINOUS YEASTS

(75) Inventors: Seung-Pyo Hong, Hockessin, DE (US); Zhixiong Xue, Chadds Ford, PA (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 200 days.

(21) Appl. No.: 13/339,461

(22) Filed: Dec. 29, 2011

(65) Prior Publication Data

US 2012/0329160 A1 Dec. 27, 2012

Related U.S. Application Data

(60) Provisional application No. 61/428,655, filed on Dec. 30, 2010.

(51) Int. Cl.

| | |
|---|---|
| ***C12P 21/06*** | (2006.01) |
| ***C12N 1/16*** | (2006.01) |
| ***C12P 7/64*** | (2006.01) |
| ***C07K 14/39*** | (2006.01) |

(52) U.S. Cl.

CPC ............... *C07K 14/39* (2013.01); *C12P 7/6427* (2013.01); *C12P 7/6409* (2013.01)

USPC ........................ 435/69.1; 435/134; 435/254.2

(58) Field of Classification Search

None

See application file for complete search history.

(56) References Cited

U.S. PATENT DOCUMENTS

| | | | |
|---|---|---|---|
| 7,238,482 | B2 | 7/2007 | Picataggio et al. |
| 7,550,286 | B2 | 6/2009 | Damude et al. |
| 7,588,931 | B2 | 9/2009 | Damude et al. |
| 7,932,077 | B2 | 4/2011 | Damude et al. |
| 2009/0093543 | A1 | 4/2009 | Xue et al. |
| 2010/0317072 | A1 | 12/2010 | Hong et al. |

OTHER PUBLICATIONS

International Search Report, PCT International Application No. PCT/US2011/067748, Mailed Apr. 28, 2012.

Akada et al., Use of Yap1 Overexpression Cassette Conferring Specific Resistance to Cerulenin and Cycloheximide as an Efficient Selectable Marker in the Yeast *Saccharomyces cerevisiae*, Yeast, vol. 19 (2002), pp. 17-28.

Avery et al., *Saccharomyces cerevisiae* Expresses Three Phospholipid Hydroperoxide Glutathione Peroxidases, The Journal of Biological Chemistry, vol. 276, No. 36, Issue of Sep. 7, 2001, pp. 33730-33735.

Avery et al., Genetic Dissection of the Phospholipid Hydroperoxidase Activity of Yeast Gpx3 Reveals its Functional Importance, The Journal of Biological Chemistry, vol. 279, No. 45, Issue of Nov. 5, 2004, pp. 46652-46658.

Chae et al., Cloning, Sequencing, and Mutatio of Thiol-Specific Antioxidant Gene of *Saccharomyces cerevisiae*, The Journal of Biological Chemistry, vol. 268, No. 22, Issue of Aug. 5, 1993, pp. 16815-16821.

Chen et al., The bZIP Transcription Factor CGAP1P is Involved in Multidrug Resistance and Require for Activation of Multidrug Transporter Gene CGFLR1 in *Candida glabrata*, Gene, vol. 386 (2007), pp. 63-72.

Delaunay et al., H2O2 Sensing Through Oxidation of the Yap1 Transcription Factor, The EMBO Journal, vol. 19, No. 19 (2000), pp. 5157-5166.

Delaunay et al., A Thiol Peroxidase is an H202 Receptor and Redox-Transducer in Gene Activation, Cell, vol. 111 (2002), pp. 471-481.

Godon et al., The H2O2 Stimulon in *Saccharomyces cerevisiae*, The Journal of Biological Chemistry, vol. 273, No. 34, Issue of Aug. 28, 1998, pp. 22480-22489.

Gulshan et al., Ybp1 and its Homologue Ybp2/Ybh1 Influence Oxidative-Stress Tolerance by Nonidentical Mechanisms in *Saccharomyces cerevisiae*, Eukaryotic Cell, vol. 3, No. 2 (2004), pp. 318-330.

Gulshan et al., Differential Oxidant Tolerance Determined by the Key Transcription Factor Yap1 is Controlled by Elevels of the Yap1-Binding Protein, Ybp1, The Journal of Biological Chemsitry, vol. 286, No. 39 (2011), pp. 34071-34081.

Howlett et al., Relationship Between Cadmium Sensitivity and Degree of Plasma Membrane Fatty Acid Unsaturation in *Saccharomyces cerevisiae*, Appl. Microbiol. Biotechnol., vol. 48 (1997), pp. 539-545.

Howlett et al., Induction of Lipid Peroxidation During Heavy Metal Stress in *Saccharomyces cerevisiae* and Influence of Plasma Membrane Fatty Acid Unsaturation, Applied and Environmental Microbiology, vol. 63, No. 8 (1997), pp. 2971-2976.

Ikner et al., Yeast Signaling Pathways in the Oxidative Stress Response, Mutation Research, vol. 569 (2005), pp. 13-27.

Inoue et al., Genetic Analysis of Glutathione Peroxidase in Oxidative Stress Response of *Saccharomyces cerevisiae*, The Journal of Biological Chemistry, vol. 274, No. 38, Issue of Sep. 17, 1999, pp. 27002-27009.

Lee et al., Yap1 and Skn7 Control Two Specialized Oxidative Stress Response Regulons in Yeast, The Journal of Biological Chemistry, vol. 274, No. 23, Issue of Jun. 4, 1999, pp. 16040-16046.

Moye-Rowley et al, Yeast Yap1 Encodes a Novel Form of the Jun Family of Transcriptional Activator Proteins, Genes & Development, vol. 3 (1989), pp. 283-292.

Porter et al., Mechanisms of Free Radical Oxidation of Unsaturated Lipids, Lipids, vol. 30, No. 4 (1995), pp. 277-290.

(Continued)

*Primary Examiner* — Nancy T Vogel

(57) ABSTRACT

Transgenic oleaginous yeast having increased oil content comprising increased Yap1 transcription factor activity, wherein the increased oil content is compared to the oil content of a non-transgenic oleaginous yeast, are described herein. The increased Yap1 transcription factor activity results from overexpressing a Yap1 transcription factor, by increasing the interaction between the transcription factor and a protein that is capable of activating the transcription factor, or by a combination thereof. Methods of using these yeast strains are also described.

10 Claims, 15 Drawing Sheets

(56) References Cited

OTHER PUBLICATIONS

Figure 1:
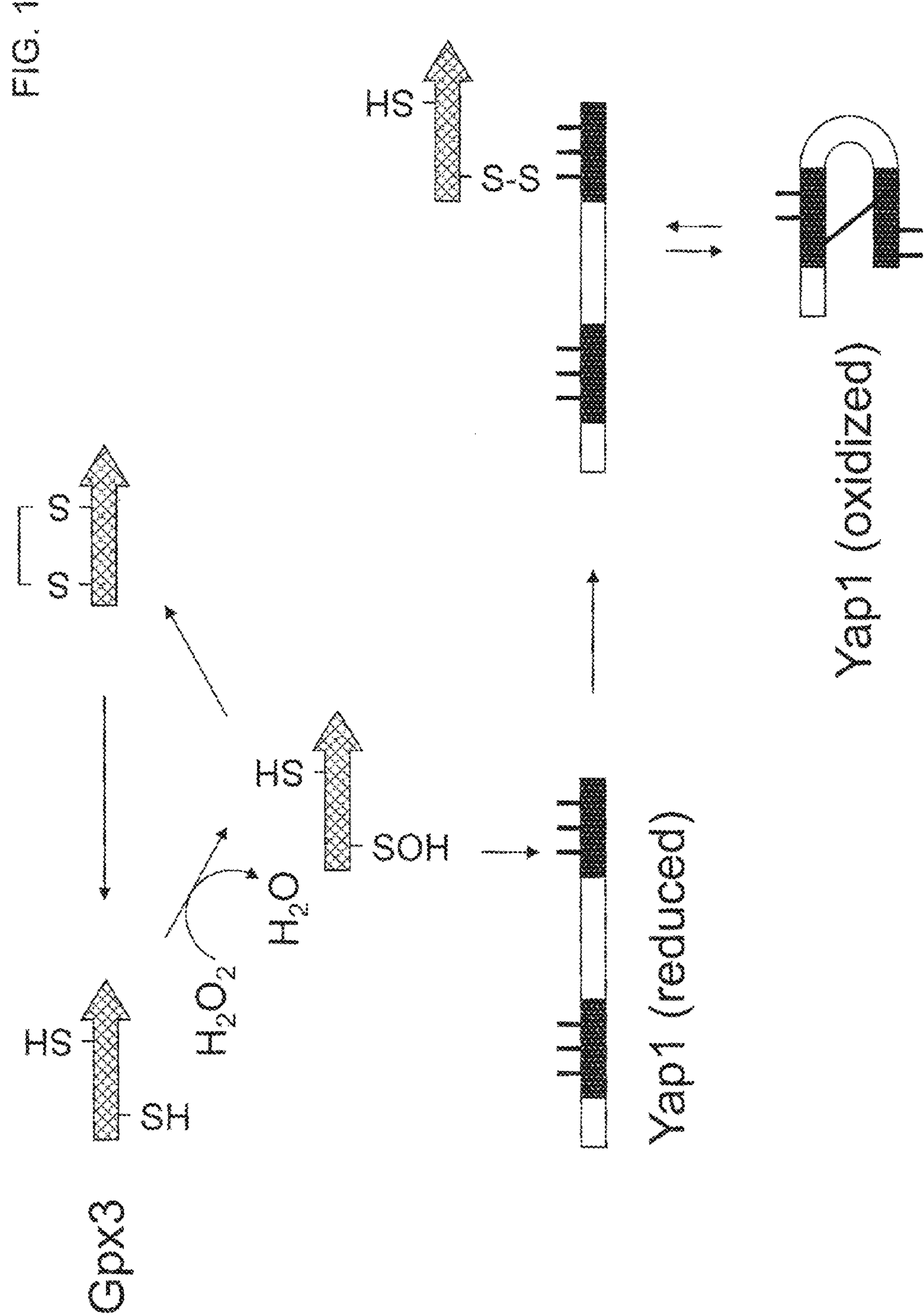

Okazaki et al., Multistep Disulfide Bond Formation in Yap1 is Required for Sensing and Transduction of H2O2 Stress Signal, Molecular Cell, vol. 27 (2007), pp. 675-688.
Tachibana et al., A Major Peroxiredoxin-Induced Activation of Yap1 Transcription Factor is Mediated by Reduction-Sensitive Disulfide Bonds and Reveals a Low Level of Transcriptional Activation, The Journal of Biological Chemistry, vol. 284, No. 7 (2009), pp. 4464-4472.
Trotter et al., The Yeast Tsa1 Peroxiredoxin in a Ribosome-Associated Antioxidant, Biochem. J., vol. 412 (2008), pp. 73-80.
Veal et al., Ybp1 is Required for the Hydrogen Peroxide-Induced Oxidation of the Yap1 Transcription Factor, The Journal of Biological Chemistry, vol. 278, No. 33, Issue of Aug. 15, 2003, pp. 30896-30904.
Veal et al., Additions and Corrections to Citation 22 (Above), The Journal of Biological Chemistry, vol. 279, No. 47, Issue of Nov. 19, 2004, p. 49562.
Kho et al, Gpx3-Dependent Responses Against Oxidative Stress in *Saccharomyces cerevisiae*, J. Microbiol. Biotechnol., vol. 18, No. 2 (2008), pp. 270-282.

FIG. 2A

```
ScYap1 (SEQ ID NO:2)      ----------------------------------MSVSTAKRSLDVVSPGSLAEFEGSKS
YlYap1 (SEQ ID NO:4)      MYSDYNIPGAMPASMAMPPFKQEFDYAQYDLNQPLPPQQQQQPIDLTPGGPLPVSDYSTS
                                                            :.  . ::.:*:.. *.*.  : *.*

ScYap1 (SEQ ID NO:2)      RHDEIENEHRR------TGTRDGEDSEQPKKKGSKTSKKQDLDPETK-------QKRTAQ
YlYap1 (SEQ ID NO:4)      SYTLDNDSQKRKMSPGESTSDGGADDESPEGDDGEADPKKPRKPGRKPETTIPASKRKAQ
                           :   ::.::*       : : .* *.*.*: ...::. *:  .*  *       .**.**

ScYap1 (SEQ ID NO:2)      NRAAQRAFRERKERKMKELEKKVQSLESIQQQNEVEATFLRDQLITLVNELKKYRPETRN
YlYap1 (SEQ ID NO:4)      NRAAQRAFRERKEKHLRDLETKISQLEGETAAKNSENEFLRFQVQRLQNELKLYREKPAG
                          ************:::::**.*:..**.    :: *  *** *:  * **** ** :. .

ScYap1 (SEQ ID NO:2)      DSKVLEYLARRDPNLHFSKNNVNHSNSEPIDTPNDDIQENVKQKMNFTFQYPLDNDNDND
YlYap1 (SEQ ID NO:4)      TSGASGVSGAGAPASNVHSAPIPEMSSKP-----------------FTFEFPSYN-----
                           *  .    .   *  :. .  : . .*:*                 ***::*  *

ScYap1 (SEQ ID NO:2)      NSKNVGKQLPSPNDPSHSAPMPINQTQKKLSDATDSSSATLDSLSNSNDVLNNTPNSSTS
YlYap1 (SEQ ID NO:4)      --------VPKPTDVEREAREQLQREQIRGYLQRKPSSVASDTTSPASQTSCNQSPCTNP
                                  :*.*.* .:.*   ::: * :      ..**.: *: * :.:.  * . .:..

ScYap1 (SEQ ID NO:2)      MDWLDNVIYTNRFVSGDDGSNSKTKNLDSNMFSNDFNFENQFDEQVSEFCSKMNQVCGTR
YlYap1 (SEQ ID NO:4)      SAYTS--------PQSQSGSVSQQKPLLG---ATIAAMNGKPDPHAVDFCAELSKACVN-
                            : .          ..:.** *: * * .   :.   ::.: * :. :**::::.:.* .
```

FIG. 2B

```
ScYap1 (SEQ ID NO:2)    QCPIPKKPISALDKEVFASSSILSSNSPALTNTWESHSNITDNTPANVIATDATKYENSF
YlYap1 (SEQ ID NO:4)    KAELLQRSATASASPTTSNTVVPSAAAPGSTQQSAGQPSVSTPTSS--------------
                        :. : ::. :*  . . :.: : *: :*. *:   .:..::  *.:

ScYap1 (SEQ ID NO:2)    SGFGRLGFDMSANHYVVNDNSTGSTDSTGSTGNKNKKNNNNSDDVLPFISESPFDMNQVT
YlYap1 (SEQ ID NO:4)    ---------TTAPPQLSASVATAGSDLPGSD----------------FLFDMPFDMDFMS
                                 :*   :  . :*..:* .**                *: : ****: ::

ScYap1 (SEQ ID NO:2)    NFFSPGSTGIGNNAASNTNPSLLQSSKEDIPFINANLAFPDDNSTNIQLQPFSESQSQNK
YlYap1 (SEQ ID NO:4)    ------------------------------------------------YRDPVSETAHLDD
                                                                          :*.**:   :.

ScYap1 (SEQ ID NO:2)    FDYDMFFRDSSKEGNNLFGEFLEDDDDDKKAANMSDDESSLIKNQLINEEPELPKQYLQS
YlYap1 (SEQ ID NO:4)    FSLPELTTETS---------------------MFDPLDPHSSSDVISGKP------LST
                        *.    :  ::*                     * *  ..  ..::*. :*      *.:

ScYap1 (SEQ ID NO:2)    VPGNESEISQKNGSSLQNADKINNGNDNDNDNDVVPSKEGSLLRCSEIWDRITTHPKYSD
YlYap1 (SEQ ID NO:4)    MGATHSGVNNGQGSGAPEVKKE------EDEDLLMFSKPKTLMNCTAVWDRITSHPKFGD
                        : ...* :.: :**.  :..*       :::: :: **  :*:.*: :*****:***:.*

ScYap1 (SEQ ID NO:2)    IDVDGLCSELMAKAKCSERGVVINAEDVQLALNKHMN
YlYap1 (SEQ ID NO:4)    IDIEGLCSELRNKAKCSESGVVLTELDVDGVLSTFQ-
                        **::******  ****** ***:.  **: .*...
```

| | |
|---|---|
| * - single, fully conserved residue | . - conservation of weak groups |
| : - conservation of strong groups | - no consensus |

B
pYRH61
8043 bp
FBA1p
PMB1
AP'
CEN6
ARSH4
PstI (4239)
NcoI (4008)
URA3
F1 ORI
EcoRI (2207)
FBAt
ClaI (1803)
NotI (1613)
NcoI (1557)
PstI (977)
Yl Yap1 YALI0F03388g
HindIII (520)
SmaI (230)
XmaI (228)
NcoI (47)
SpeI (1)
A
pYRH60
7412 bp
SphI (1)
F1 Ori
BspHI (789)
Amp
BspHI (1797)
ColE1
PstI (2517)
AscI (2761)
5' Yap1
HindIII (3242)
BsiWI (3641)
HindIII (3653)
ClaI (4144)
BspHI (4768)
Ura3
NcoI (6139)
EcoRI (6211)
PstI (6231)
PstI (6249)
ClaI (6293)
NcoI (6814)
3' Yap1
EcoRI (6966)
PstI (7316)
NcoI (7322)
ClaI (7369)

FIG. 4
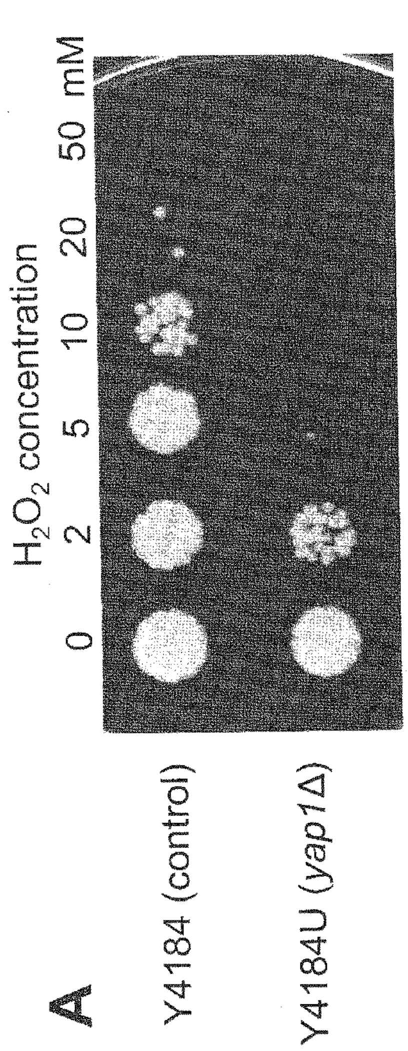
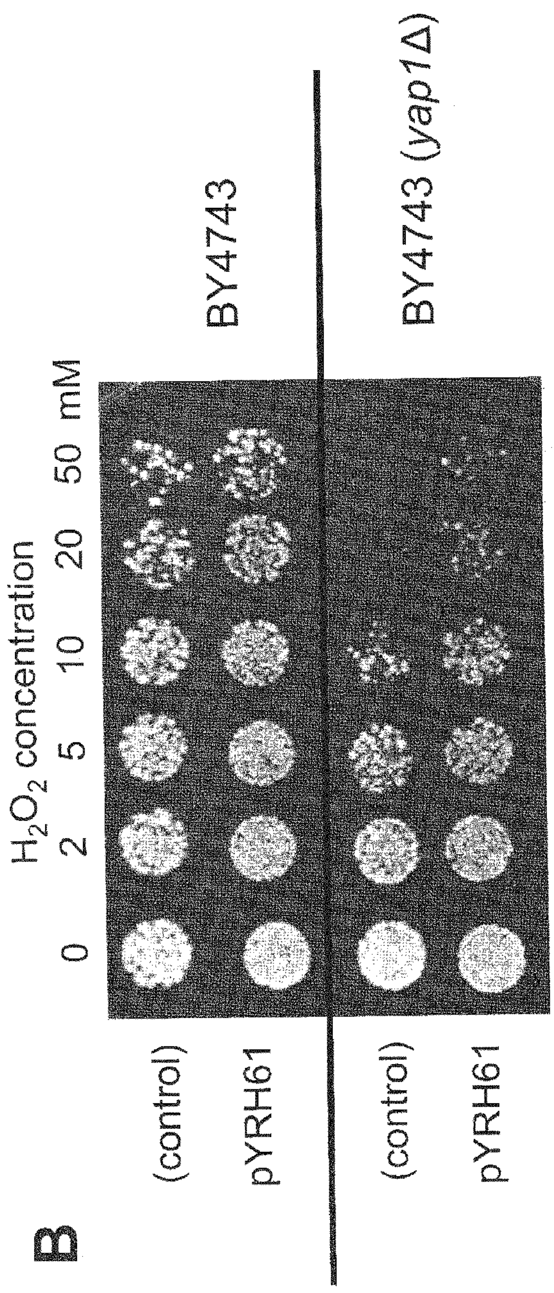

B
pYRH65
Gpx3
Pex20-3'
LipY-5'
Amp
LipY-3'
Ura3
FBAINm
A
pYRH43
Pex20-3'
ColE1
Amp
f1 ori
ARS 18
Ura3
FBAINm
Yap1

FIG. 6

```
ScGpx3 (SEQ ID NO:26)   MS------EFYKLAPVDKKGQPFPFDQLKGKVVLIVNVASKCGFTPQYKELEALYKRYKD
YlGpx3 (SEQ ID NO:28)   MSAEKTNTAFYNLAPLDKNGEPFPFKQLEGKVVLIVNVASKCGFTPQYKGLEEVYQKYKD
                        **       **:***:**:*:****.**:******************** ** :*::***

ScGpx3 (SEQ ID NO:26)   EGFTIIGFPCNQFGHQEPGSDEEIAQFCQLNYGVTFPIMKKIDVNGGNEDPVYKFLKSQK
YlGpx3 (SEQ ID NO:28)   QGFTIIGFPCNQFGGQEPGSADEISSFCQLNYGVTFPVLQKINVNGNDADPVYVYLKEQK
                        :************* ***** :**:.**********:::**:***.: **** :**.**

ScGpx3 (SEQ ID NO:26)   SGMLGLRGIKWNFEKFLVDKKGKVYERYSSLTKPSSLSETIEELLKEVE
YlGpx3 (SEQ ID NO:28)   AGLLGFRGIKWNFEKFLVDKHGNVVDRYASLKTPAGLESTIETLLKKP-
                        :*:**:*************:*:* :**:**..*:.*..*** ***:
```

| | |
|---|---|
| * - single, fully conserved residue | . - conservation of weak groups |
| : - conservation of strong groups | - no consensus |

FIG. 7

```
ScTsa1 (SEQ ID NO:34)   MVAQVQKQAPTFKKTAVVDGVFDEVSLDKYKGKYVVLAFIPLAFTFVCPTEIIAFSEAAK
YlTsa1 (SEQ ID NO:36)   MVATVQHPAPDFKKTAVSGGVFEEVSLDQFKGKWVVLAFIPLAFTFVCPTEIIAYSDAVS
                        *** **: ** ******  .***:*****::***:*********************:*:*..

ScTsa1 (SEQ ID NO:34)   KFEEQGAQVLFASTDSEYSLLAWTNIPRKEGGLGPINIPLLADTNHSLSRDYGVLIEEEG
YlTsa1 (SEQ ID NO:36)   QFKERGAEVLFASTDSEYSLLAWTNVARKDGGLGPVNIPLLADTNHTLSKDYGVLIPEAG
                         :*:*:**:*****************:.**:*****:**********:**:****** * *

ScTsa1 (SEQ ID NO:34)   VALRGLFIIDPKGVIRHITINDLPVGRNVDEALRLVEAFQWTDKNGTVLPCNWTPGAATI
YlTsa1 (SEQ ID NO:36)   VALRGIFIIDPKGVVRQITINDLPVGRSVEETLRLIDAFQFTEKHGEVCPANWQKGSDTI
                        *****:********:*:**********.*:*:***::***:*:*:* * *.**  *: **

ScTsa1 (SEQ ID NO:34)   KPTVEDSKEYFEAANK
YlTsa1 (SEQ ID NO:36)   KADPVNAKEYFEKANK
                        *.   ::***** ***
```

* - single, fully conserved residue
: - conservation of strong groups
. - conservation of weak groups
- no consensus

FIG. 8A

```
ScYbp1 (SEQ ID NO:38)   ---MEPIDDILFEVTDAFKTQKEDLLELVTLIDIYG---EQVNQEGSYEEKTRFIETLNT
YlYbp1 (SEQ ID NO:40)   MQLTDDHKKDLEKLGEELKGKEEHTVAGEDEEDVNHGADDSEDAEDEDAEDENDYTELDV
                            :  .. * :: : :* ::*. :      *:     :. : *..  *. .    *:.

ScYbp1 (SEQ ID NO:38)   LLEDNPSTTGEIGWDLPKGLLKFLSKDNVDVNGRLGTNMIVQGVMKCFYAISIQGEPKKC
YlYbp1 (SEQ ID NO:40)   DIVCQFIKDAAREAEKTGDYISYATVIDIHCSDPSRYKHVDRVKILTSLLEVLRTNPKIC
                         :  :  . .    : . . :.: :  ::. ..    : : :  :       :: :** *

ScYbp1 (SEQ ID NO:38)   LITGLELLSSLCS----KDFSKSDQQNKED-------FVDKKANTLPPEGVIENSSNRKD
YlYbp1 (SEQ ID NO:40)   EEIGWDLPALLLPYFNVEDFDFNDGLEGHPTFYPLIMLFSTLAEYGNPKELFLKTVETLS
                           * :* : * .    :**. .*  : .        :... *:   *: :: :: :  .

ScYbp1 (SEQ ID NO:38)   FPSYGESKSSNEFFLKLKS----------YILFEFIGASLKRISTLFPSKYLGAAVSTIE
YlYbp1 (SEQ ID NO:40)   TLTCDRAPENDKLKFKQAESLRKFEVCKFHVLEELMSSCMKKIKTQYPSRFLASAASAIL
                          : ..: ..::: :*  .          ::* *::.:.:*:*.* :**::*.:*.*:*

ScYbp1 (SEQ ID NO:38)   KFVYSHADTFEDALFLL----RRVYTFCRNY-IPPDPPKDIQLNEDFTREMFDKVVEEES
YlYbp1 (SEQ ID NO:40)   MFSARNAALFRHFPLIVGILARRVYVFIRDWGMDGDEPMDMSPDE---QAKSAKILQSLS
                         *   :*  *..  :::    ****.* *:: :  * * *:. :*   :    *:::. *

ScYbp1 (SEQ ID NO:38)   ELQVRLLRRLCTFGISTPIKTVTTNADVKYYCALNQQKFELSAYYTEYLELFCRYYQMAF
YlYbp1 (SEQ ID NO:40)   TYFFYSWFHRVAVRWSSNLFREIKHSIHELPRAERAKYDNPKSNGSAVYTIYNRWGTLAL
                           .    : :.   *: :    .::  :   * . :  : .:  :    :: *:  :*:
```

FIG. 8B

```
ScYbp1 (SEQ ID NO:38)   SLDVDIEGEFQNVIKECRIIYKSVPQEISAVNDEAKLVLERMVYKLAYTFEVQKAAKEKN
YlYbp1 (SEQ ID NO:40)   SLDLDPSQYFLPLIQEIQEDVQEATKGGLDDTLAGFSKSSLSDASPIAFVDYSMYDDASE
                        ***:* .   * :*:* :   :...:     .  .    .    .    .: .   . .:

ScYbp1 (SEQ ID NO:38)   VGLDYNGVILFSGIHYLETNQH-LVKEMNITDAIYLYLRFTTPSLYSKVYYNVAVESVSR
YlYbp1 (SEQ ID NO:40)   IPLSQEGLLMLATQYMMENRDHSLNISLDQLVSLTLYLVHRSS---PKEPLPFAITDLLL
                        : *. :*:::::  : :*..:* *  .::    :: *** . :.    .*   .*: .:

ScYbp1 (SEQ ID NO:38)   YWLWYAITTEPLEDVKKELKNLSVFVTKTLLHVLLQKNCIQVNQQLRMITFTLLTRLLCL
YlYbp1 (SEQ ID NO:40)   FWGWWTLK----DMERPEVRQLDEAFYVKYLQFLVFISASSPLPEIRNIAYTLCGRLLYL
                        :* *:::.    :  : *:::*.  .  . *:.*:  .. .   ::* *::**  *** *

ScYbp1 (SEQ ID NO:38)   IPEKVAFEFILDVLKTSPLPLAKTSVLCVFKDLSRRRISTKDNDSETDLIVEKLSKLKVN
YlYbp1 (SEQ ID NO:40)   QHESVSFAFIADTIADCPFENAQVAMVGILKRLMIP-----------DEISDQLSKLRIP
                          *.*:* ** *.:  .*:  *:.::: ::* *              *  * ::****::

ScYbp1 (SEQ ID NO:38)   DSNKAQQSNIRHYIQLDSSKMKAVHDCCLQTIQDSFTADAKKSDILLLLTYLNIFIVLKK
YlYbp1 (SEQ ID NO:40)   DVPTREG----VEHQKASQTTIPTTPEHVDTIKSLCNAALEQENTHLVITWLNFLSTVK-
                        *  . :        *  *..  ..    ::**:.  .*  ::.:  *::*:**:: .:*

ScYbp1 (SEQ ID NO:38)   TWDEDLLKIVCSKIDSNLKSVEPDKLPKYKEIVDKNESLNDYFTGIK
YlYbp1 (SEQ ID NO:40)   -LDCGFAGDYAERVEKVIDEVEDENDRTLIRLALDVLAKTV------
                          * .:    ..:::. :..** ::  .  .:. .  :  .
```

| | |
|---|---|
| * - single, fully conserved residue | . - conservation of weak groups |
| : - conservation of strong groups | - no consensus |

FIG. 9A

```
CaYbp1 (SEQ ID NO:47)    -----------------------------------------MSETDHSETSESTIEPFQF
SsYbp1 (SEQ ID NO:45)    -----------------------------------------MSESDVSENSESTIEPFVF
CgYbp1 (SEQ ID NO:43)    -------------------------------------------------------MSDAF
ScYbp1 (SEQ ID NO:38)    --------------------------------------------------------MEPI
ZrYbp1 (SEQ ID NO:46)    --------------------------------------------------------MENI
KlYbp1 (SEQ ID NO:44)    ----------------------------------------------------MPLEVERF
YlYbp1 (SEQ ID NO:40)    MQLTDDHKKDLEKLGEELKGKEEHTVAGEDEEDVNHGADDSEDAEDEDAEDENDYTELDV

CaYbp1 (SEQ ID NO:47)    EKVMENLESGAQDALQSKDFLSYSTLLDIYLNDP-TKYSNEEKEQLLGHILTILSENKQL
SsYbp1 (SEQ ID NO:45)    ERVLESLKTAATETLESKDYLSYSTLLDIYLGEP-AKYTYDEREELLSALLSILSANPGL
CgYbp1 (SEQ ID NO:43)    EEVCDALKASFTDDKE--DSLTLVTMIDTLSEEVDEGFEVKEKEQFLELLLNLLEADTEL
ScYbp1 (SEQ ID NO:38)    DDILFEVTDAFKTQKE--DLLELVTLIDIYGEQVNQEGSYEEKTRFIETLNTLLEDNPST
ZrYbp1 (SEQ ID NO:46)    DTVCENLEKAFAEQKD--DSVTLATIIDMYVVQINDEGSNKDKEQFLTKLLDQLRASPDI
KlYbp1 (SEQ ID NO:44)    KEIEEKLLTAFVEEKS--DIITLVTILDLYSEEVNFKGSLEQKYEYLSEVLSLLQQNKDV
YlYbp1 (SEQ ID NO:40)    DIVCQFIKDAAREAEKTGDYISYATVIDIHCSDP-SRYKHVDRVKILTSLLEVLRTNPKI
                               :  .     .  * :   *::*    :        :: . :  :   *  .

CaYbp1 (SEQ ID NO:47)    TYEIGWDLPQLLILYVDS-DYEFNGPIRDSPGVYKILKIFENLAINGNHKELFLKSCELL
SsYbp1 (SEQ ID NO:45)    TYEIGWDLPGLLILYVDS-DFDFTGGLRKAPCVYKILKIFEVLAINGNPKELFLKSCELL
CgYbp1 (SEQ ID NO:43)    VSAVGWDLPRTLLRFCNAKNIKNSDRLRKCKVVTICMAIFNLLALHAKPQECLVTTLELL
ScYbp1 (SEQ ID NO:38)    TGEIGWDLPKGLLKFLSKDNVDVNGRLGTNMIVQGVMKCFYAISIQGEPKKCLITGLELL
ZrYbp1 (SEQ ID NO:46)    VAEIGWDLPRGLLKFYNKKNIDVDAKLKSNPIVGLVMQCFSEVALSGNPKECLLTGCEIL
KlYbp1 (SEQ ID NO:44)    VYEIGWDLPKILIKFIHWGNNNHLGADRSKKFLTVIMKCFNEVALFGNPKECFFAGCELM
YlYbp1 (SEQ ID NO:40)    CEEIGWDLPALLLPYFNVEDFDFNDGLEGHPTFYPLIMLFSTLAEYGNPKELFLKTVETL
                            :*****  *: :    : .          .   :  *  ::  .: :: :.   * :
```

FIG. 9B

```
CaYbp1 (SEQ ID NO:47)   NDLELSQ-------------------DEDIELLKREN-----------------------
SsYbp1 (SEQ ID NO:45)   TTISADD------------------SQVTDDSSIKEK-----------------------
CgYbp1 (SEQ ID NO:43)   SELNFKN-------------IVEECHQLSEDGSDNNTAEEDNDAVEDYMKDR-DQP----
ScYbp1 (SEQ ID NO:38)   SSLCSKD-------------FSKSDQQNKEDFVDKKANTLPPEGVIENSSNRKDFPSYG-
ZrYbp1 (SEQ ID NO:46)   SELTTIQ-------------IN---EQMLEDDSKEEGDVTKDEKKTDEKGEWIPEPP---
KlYbp1 (SEQ ID NO:44)   SSLRINDESLVRFIVEEEPVMDPENEDSGDETYTEDEGSSDKTEEEEEKNAVKDSPTPKS
YlYbp1 (SEQ ID NO:40)   STLTCDR------------------APENDKLKFKQAESLR-------------------
                        . :                           .   ..

CaYbp1 (SEQ ID NO:47)   ----------------------FFEIKLYCVFELIDACLKKIHTLYPSRFLAMTVSSFNN
SsYbp1 (SEQ ID NO:45)   ----------------------FFDVKLYCIFELVDSCFKRIKTYYPSRFLAMTVASFIN
CgYbp1 (SEQ ID NO:43)   --------------------EIIFGVKSYALFELAGSLIRRVATLHPSKYLEEAVTAIRK
ScYbp1 (SEQ ID NO:38)   --------------ESKSSNEFFLKLKSYILFEFIGASLKRISTLFPSKYLGAAVSTIEK
ZrYbp1 (SEQ ID NO:46)   ---------------HRDPVEFFLYLNSYVLFELIQTALKRIASLYPSKFLGMAVSAIYK
KlYbp1 (SEQ ID NO:44)   ANESIPDLKEGYAFYGRLPQEVITELRFYSIIELMGSTLKRIVTLHPSKFLSEAVEAFSR
YlYbp1 (SEQ ID NO:40)   ---------------------KFEVCKFHVLEELMSSCMKKIKTQYPSRFLASAASAILM
                                              :   . : : *:  : :::: : .**::*  :. ::

CaYbp1 (SEQ ID NO:47)   LMFKLTKQHGSLGNYHFVM----KRVYSFCRNYISPPLP---TNAKEMPQEELDKIVKDE
SsYbp1 (SEQ ID NO:45)   LAHK--NGNDSPNNISFIM----KRAYTFARNYSSPPLP--DSDGDKMSPEDLSKIKEDE
CgYbp1 (SEQ ID NO:43)   YVTN---NTEVVEDVKFIL----RRVFAFCRGYIPPEPPRQLIVDLKMNHEEYDEIMNSE
ScYbp1 (SEQ ID NO:38)   FVYS---HADTFEDALFLL----RRVYTFCRNYIPPDPPKDIQLNEDFTREMFDKVVEEE
ZrYbp1 (SEQ ID NO:46)   FVRN---NIDEVYNTPFIL----RRIYTFCRGYIPPEIPKQLLENTKLEKKELDKITEDE
KlYbp1 (SEQ ID NO:44)   FNLQ---NNEDVDDCLFIL----RRLYSFIRGYIPPSPPP--DADKQVSAEELEEIKVSE
YlYbp1 (SEQ ID NO:40)   FSAR---NAALFRHFPLIVGILARRVYVFIRDWGMDG-----DEPMDMSPDEQAKSAKIL
                                     .  :::    :* : * *.:             ..  .   :
```

FIG. 9C

```
CaYbp1 (SEQ ID NO:47)   EYLQRRLLTGFLTQVIYLANINGTEGYSIEHFSWLQQQSKSKIKFVFERDG--AFCDRFV
SsYbp1 (SEQ ID NO:45)   EYLQRKLLTGFISQLIQLMSNDNLNGYTLDHLSFLQVPHRGQLKKYFEYSVNLPVMDRLA
CgYbp1 (SEQ ID NO:43)   IELQVRLLRNLCTFSVAYCVKFLNDKTEVVYFHKLI---NKDLQLPEFYRSVHDIISRYY
ScYbp1 (SEQ ID NO:38)   SELQVRLLRRLCTFGISTPIKTVTTNADVKYYCALN---QQKFELSAYYTEYLELFCRYY
ZrYbp1 (SEQ ID NO:46)   SILQGQLLRSLSTFAVGECLKNKASRLDLEYFHRLR---NTEFHLSENDEELVLISKRFY
KlYbp1 (SEQ ID NO:44)   EVLQRKLLCNILTSALHQLLKARTCISLLNYHSHLQG-IPTLSTSSEYLGQLTDILSRYY
YlYbp1 (SEQ ID NO:40)   QSLSTYFFYSWFHRVAVRWSSNLFREIKHSIHELPRAERAKYDNPKSNGSAVYTIYNRWG
                          *.  ::                                                 .  *

CaYbp1 (SEQ ID NO:47)   ELASSFDIDLLKCFQ-GFITDSHKLLIGIDYKNKNKSEDEIIELLFERVVVDYQKNVLTS
SsYbp1 (SEQ ID NO:45)   ELALSYDINLTQHFK-SMVADSHTLLRSFDYS---IDRDELSAQIFEKVVVDYQKTLAMS
CgYbp1 (SEQ ID NO:43)   QIAFSFDIDLNDEFN-DILRETRGIYEDVIKRINETNNTDKNAKSDILLKAGYYYEVQK-
ScYbp1 (SEQ ID NO:38)   QMAFSLDVDIEGEFQ-NVIKECRIIYKSVPQEISAVNDEAKLVLERMVYKLAYTFEVQK-
ZrYbp1 (SEQ ID NO:46)   QLMFSFDLDVKEQFL-SFIEETKGIYKALPPDSEIPNDEARRAIGQVVYQLSYTYQLQK-
KlYbp1 (SEQ ID NO:44)   QLATSFDIDVSAEFKRLCVDESVRIYRSLPKDSEIKSDEELKEITNFVYQLAYTYEVEK-
YlYbp1 (SEQ ID NO:40)   TLALSLDLDPSQYFL----PLIQEIQEDVQEATKGGLDDTLAGFSKSSLSDASPIAFVDY
                         :  * *::    *          :   .                            .

CaYbp1 (SEQ ID NO:47)   IVDSDAKAIKDSIIGELILFTHSIAGKKNFAKPTMSIHDSLVMTLRLIIPQMVNPKFINA
SsYbp1 (SEQ ID NO:45)   IINSDAKEIRDSPLGIFLLYTHAISVRRTFDLIKVSFSDAVVLTLRVLVPELVQSTFVFK
CgYbp1 (SEQ ID NO:43)   --TAREKEINPDTKGIILLSGFNYIENGDHLI-DIDIADALYLYLRFASESLFSPTCHNV
ScYbp1 (SEQ ID NO:48)   --AAKEKNVGLDYNGVILFSGIHYLETNQHLVKEMNITDAIYLYLRFTTPSLYSKVYYNV
ZrYbp1 (SEQ ID NO:46)   --LTKLKHLELNSNGIFILSGLHYQETQKHLYPEISIKDTVLLYIRCATPSLFSSTYTNL
KlYbp1 (SEQ ID NO:44)   --IANVKEILLDPAGILILRSFSNEDFLPPSDAKITLQEAIYMYLRFVTPSMFSALFENR
YlYbp1 (SEQ ID NO:40)   SMYDDASEIPLSQEGLLMLATQYMMENRDHS-LNISLDQLVSLTLYLVHRSSPKEPLP-F
                              . :  .  * :::                : : : : : :     .  .
```

FIG. 9D

```
CaYbp1 (SEQ ID NO:47)   GNHDVVVFWVWFALYQQQIINSKNLQLEISYIPKVLLTTFFQCLLFIVIKSEGKPNFKYM
SsYbp1 (SEQ ID NO:45)   GVEDATIFWTWYALYQTSLNN-KSVETEIAAISPVLLTIYYQVIFFVVITNSNRPNFKYA
CgYbp1 (SEQ ID NO:43)   TIEGVARYWIWAALTTTDNN---ILKEKLAELSPLVLHSVLNLLLVKNCHQVNE-EIRMI
ScYbp1 (SEQ ID NO:38)   AVESVSRYWLWYAITTEPLE---DVKKELKNLSVFVTKTLLHVLLQKNCIQVNQ-QLRMI
ZrYbp1 (SEQ ID NO:46)   YAEGTARYWVWVAITNNKVQ---KLREELSELPSYIRTVFLQMVLMQSCNQPNE-EARMI
KlYbp1 (SEQ ID NO:44)   SSHDLARTWILFALTNNSTH---DLMDSLKDLPSYIITVYLQTELIRACLQIND-NLRRT
YlYbp1 (SEQ ID NO:40)   AITDLLLFWGWWTLKDMERP-------EVRQLDEAFYVKYLQFLVFISASSPLP-EIRNI
                          .    *   ::              .:  :   .      :  .     .    : :

CaYbp1 (SEQ ID NO:47)   LLTLLTKLLTLSP-DTGYEFIKDSLNNCPYESVYPSLIGVYKQLLLN---EKWDVNSIEL
SsYbp1 (SEQ ID NO:45)   VLTLLTRVLALSPEDLSYDFVKDSLHNCPYESEKPIMIGVLKELLTK---DKSSSTSDVT
CgYbp1 (SEQ ID NO:43)   TFTLITRILCLLPENCSYEFLMDELDNCAVVFGKSCVLGILRDLVIK---VDHSVSSNNT
ScYbp1 (SEQ ID NO:38)   TFTLLTRLLCLIPEKVAFEFILDVLKTSPLPLAKTSVLCVFKDLSRR---R-ISTKDNDS
ZrYbp1 (SEQ ID NO:46)   SFTLLTRIMCLMPEDTSFEFVLDTLLTCPFTHAKIAVLGILKDLMLRNCQNKQSLEEQFS
KlYbp1 (SEQ ID NO:44)   QFSILTRILCLLPEDFAFNFIRDTLLSCPYEQAKCCALAILKDMMQH-----ERKVPQKS
YlYbp1 (SEQ ID NO:40)   AYTLCGRLLYLQHESVSFAFIADTIADCPFENAQVAMVGILKRLMIP------DEISDQL
                         ::  ::: *   . .: *: * :  ..         : : : :

CaYbp1 (SEQ ID NO:47)   EKLNISSSS-SNTPPKLPPRNG-IKRKHFSLTNESLNDLVDLINNSSKNAFVEDNS--KI
SsYbp1 (SEQ ID NO:45)   EALANSEDSKVPLPPTLPPRASSASSRYFTLTKARLEDILALVQEAVDSAFVTHESTVAI
CgYbp1 (SEQ ID NO:43)   DTEDLSESMAQLKINNEKRAKKT----FITLDPKRAGEIEDLAIKTLKETKKS------M
ScYbp1 (SEQ ID NO:38)   ETDLIVEKLSKLKVNDSNKAQQSNIRHYIQLDSSKMKAVHDCCLQTIQDSFTAD-----A
ZrYbp1 (SEQ ID NO:46)   NMNLTSKDSDKRSTSTSPPSLPP--RAYIDINEDRMASIHSAAMMTFQDQKAK-------
KlYbp1 (SEQ ID NO:44)   DEDDLAKDMEKLKIKNSPPPLPS--RAYMLLNDDRIATLHSITLLAIDSCAAD------P
YlYbp1 (SEQ ID NO:40)   SKLRIPDVPTREGVEHQKASQTT-----IPTTPEHVDTIKSLCNAALE------------
                        .   .                            :         :      : .
```

FIG. 9E

```
CaYbp1 (SEQ ID NO:47)   DPSKLSTIAAYLNLLVAIKKDPVIVENKEKLTTLISSIENKIKSVKK-----SSQNQFEL
SsYbp1 (SEQ ID NO:45)   DPSKLSTLSAYLNLLVIIKKDPVVLQDKKALDKVVESAEENIAAVKEKHKKYPNSNKFEL
CgYbp1 (SEQ ID NO:43)   KKDYILLVLNYIKFFSTFAHK----WNKSKLNEFTTLVATNFS--D---SKMLPEINAII
ScYbp1 (SEQ ID NO:38)   KKSDILLLLTYLNIFIVLKKT----WDEDLLKIVCSKIDSNLKSVE---PDKLPKYKEIV
ZrYbp1 (SEQ ID NO:46)   GKDKHILILNFLNFFNGLSQK----WDKNLLQAVHKEVALQYNEKT---KEDVPEVGFIK
KlYbp1 (SEQ ID NO:44)   ESKKVKTLLTYLNFLNAFLTK----WDSVFLKEICDAVNDKLIKNEKVGDKDEPHYSLLV
YlYbp1 (SEQ ID NO:40)   -QENTHLVITWLNFLSTVK------LDCGFAGDYAERVEKVIDEVE-----DENDRTLIR
                          .    :  :::::  .         :

CaYbp1 (SEQ ID NO:47)   NAAGMLEITIERFNE
SsYbp1 (SEQ ID NO:45)   NAAGILEITIDRIKS
CgYbp1 (SEQ ID NO:43)   DANEKLRSLTE----
ScYbp1 (SEQ ID NO:38)   DKNESLNDYFTGIK-
ZrYbp1 (SEQ ID NO:46)   IANETLGKHL-----
KlYbp1 (SEQ ID NO:44)   STVASISSKL-----
YlYbp1 (SEQ ID NO:40)   LALDVLAKTV-----
                             :
```

```
* - single, fully conserved residue          . - conservation of weak groups
: - conservation of strong groups              - no consensus
```

INCREASED OIL CONTENT BY INCREASING YAP1 TRANSCRIPTION FACTOR ACTIVITY IN OLEAGINOUS YEASTS

This application claims the benefit of U.S. Provisional Application No. 61/428,655, filed Dec. 30, 2010, which is hereby incorporated by reference in its entirety.

FIELD OF THE INVENTION

This invention is in the field of biotechnology. More specifically, this invention pertains to oleaginous yeast strains comprising increased Yap1 transcription factor activity, resulting in increased oil content.

BACKGROUND OF THE INVENTION

Reactive oxygen species ["ROS"] are chemically reactive molecules containing oxygen and comprising unpaired valence shell electrons. ROS, such as hydroxyl radicals, superoxide anions, and hydrogen peroxide ["$H_2O_2$"], are generated continually as by-products of aerobic metabolism in cells, e.g., via incomplete reduction of oxygen to water during respiration. ROS are also produced during beta-oxidation of fatty acids by exposure to radiation, light, metals, and redox active drugs. Since ROS may perturbate the cellular redox status and ultimately cause toxic damage to cellular components, including lipids, proteins, and DNA, cells must possess a variety of means to sense levels of ROS and transduce the signal such that the cell is protected against the effects of oxidative stress and cellular integrity is maintained.

Typically, levels of ROS are controlled by use of the glutathione reduction-oxidation (re-dox) cycle and thioredoxin system, such that electrons are accepted from NADPH and utilized to reduce $H_2O_2$ to water. More specifically, the electrons are transferred from NADPH to thioredoxin reductase to thioredoxin to peroxiredoxins to $H_2O_2$, yielding water. Regulation of the multiple genes in this pathway is complex. The adaptive response to $H_2O_2$ in the yeast *Saccharomyces cerevisiae* has been found to involve a change in the expression of at least 167 proteins (Godon, C. et al., *J. Biol. Chem.,* 273:22480-22489 (1998)).

One means to sense levels of $H_2O_2$ in the yeast *S. cerevisiae* relies on a signaling pathway based on the master transcription factor for the oxidative stress response, i.e., the transcription factor protein Yap1. In response to $H_2O_2$ stress, a multi-step conformational change in Yap1 occurs based on the formation of at least one intra-molecular disulfide bond, a reaction catalyzed by peroxiredoxins such as Tsa1 and Gpx3 and facilitated by other proteins such as Ybp1. In this active oxidized form, Yap1 controls the expression of a large regulon of at least 32 different proteins, including those involved in cellular antioxidant defenses and glutathione/NADPH regeneration (Lee, J. et al., *J. Biol. Chem.,* 274:16040-16046 (1999)). Deactivation of Yap1 occurs by enzymatic reduction with Yap1-controlled thioredoxins, thus providing a mechanism for autoregulation. Mutant strains of *S. cerevisiae* lacking a functional Yap1 protein are hypersensitive to killing by $H_2O_2$.

It is known that fatty acids having more double bonds are more susceptible to lipid peroxidation. Thus, polyunsaturated fatty acids ["PUFAs"] are more susceptible to oxidative degradation by ROS because they contain multiple double bonds in between which lie methylene-$CH_2$-groups that possess especially reactive hydrogens. Avery, A. M. and S. V. Avery (*J. Biol. Chem.,* 276:33730-33735 (2001)) reported that a *S. cerevisiae* gpx1Δ/gpx2Δ/gpx3Δ mutant was defective for growth in medium supplemented with the PUFA alpha-linolenic acid ["ALA"; 18:3], wherein ALA can comprise up to 60% of the total membrane fatty acids; gpx1Δ, gpx2Δ and gpx3Δ mutants also demonstrated toxicity to the 18:3, although the effect was delayed based on the slower incorporation rate of exogenous 18:3 into membrane lipids.

Since ROS are continually produced in cells performing aerobic metabolism and since ROS can lead to cell damage and death, one of skill in the art will appreciate methods that increase the capacity of recombinantly engineered organisms to defend against ROS. This is especially true in those organisms that produce microbial oils, since the generation of ROS in certain microbial strains during production of these oils can lead to lower yields and/or reduced efficiency in microbial oil production.

It has been found that engineering oleaginous yeast to have increased Yap1 transcription factor activity and to produce PUFAs results in both increased lipid content ["TFAs % DCW"] and increased average PUFA titer ["PUFA % DCW"].

SUMMARY OF THE INVENTION

In one embodiment, the invention concerns a transgenic oleaginous yeast having increased oil content comprising increased Yap1 transcription factor activity wherein the increased oil content is compared to the oil content of a non-transgenic oleaginous yeast cell.

In a second embodiment, the increased Yap1 transcription factor activity results from overexpressing the Yap1 transcription factor, by increasing the interaction between the transcription factor and a protein that is capable of activating the transcription factor, or by a combination thereof.

In a third embodiment, the protein that is capable of activating the transcription factor is selected from the group consisting of: Gpx3, Ybp1 and Tsa1.

In a fourth embodiment, the Yap1 transcription factor comprises a nucleotide sequence encoding a polypeptide having transcription factor activity and comprising: (a) a bZIP leucine zipper motif; (b) an N-terminal Cys-rich domain comprising a sequence of at least two cysteine residues that are separated by at least 6 amino acids; and, (c) a C-terminal Cys-rich domain comprising a sequence of at least two cysteine residues that are separated by at least 8 amino acids.

In a fifth embodiment, the Gpx3 protein comprises: (a) a nucleotide sequence encoding a polypeptide capable of interacting with the Yap1 transcription factor to increase Yap1 transcription factor activity, wherein the polypeptide has at least 70% amino acid identity, based on the BLASTP method of alignment, when compared to a sequence selected from the group consisting of SEQ ID NO:26 [ScGpx3] or SEQ ID NO:28 [YlGpx3]; (b) a nucleotide sequence encoding a polypeptide capable of interacting with the Yap1 transcription factor to increase Yap1 transcription factor activity, wherein the nucleotide sequence has at least 70% sequence identity, based on the BLASTN method of alignment, when compared to a sequence selected from the group consisting of SEQ ID NO:25 [ScGpx3] or SEQ ID NO:27 [YlGpx3]; and, (c) a complement of the nucleotide sequence of (a) or (b), wherein the complement and the nucleotide sequence consist of the same number of nucleotides and are 100% complementary.

In a sixth embodiment, the Tsa1 protein comprises: (a) a nucleotide sequence encoding a polypeptide capable of interacting with the Yap1 transcription factor to increase Yap1 transcription factor activity, wherein the polypeptide has at least 70% amino acid identity, based on the BLASTP method of alignment, when compared to a sequence selected from the group consisting of SEQ ID NO:34 [ScTsa1] or SEQ ID NO:36 [YlTsa1]; (b) a nucleotide sequence encoding a polypeptide capable of interacting with the Yap1 transcription factor to increase Yap1 transcription factor activity, wherein the nucleotide sequence has at least 70% sequence identity, based on the BLASTN method of alignment, when compared to a sequence selected from the group consisting of SEQ ID NO:33 [ScTsa1] or SEQ ID NO:35 [YlTsa1]; and, (c) a complement of the nucleotide sequence of (a) or (b), wherein the complement and the nucleotide sequence consist of the same number of nucleotides and are 100% complementary.

In a seventh embodiment, the Ybp1 protein comprises: (a) a nucleotide sequence encoding a polypeptide capable of interacting with the Yap1 transcription factor to increase Yap1 transcription factor activity, wherein the polypeptide is selected from the group consisting of SEQ ID NO:38 [ScYbp1] or SEQ ID NO:40 [YlYbp1]; (b) a nucleotide sequence encoding a polypeptide capable of interacting with the Yap1 transcription factor to increase Yap1 transcription factor activity, wherein the polypeptide sequence is classified within a kinetochor_Ybp2 super family, based on the conserved domain method of analysis; or, (c) a complement of the nucleotide sequence of (a) or (b), wherein the complement and the nucleotide sequence consist of the same number of nucleotides and are 100% complementary In an eighth embodiment, the transgenic oleaginous yeast cell is from a genus selected from the group consisting of: *Yarrowia, Candida, Rhodotorula, Rhodosporidium, Cryptococcus, Trichosporon*, and *Lipomyces*. Preferably, the transgenic oleaginous yeast cell is *Yarrowia lipolytica*.

In a ninth embodiment, the transgenic oleaginous yeast cell produces at least one polyunsaturated fatty acid.

In a tenth embodiment, the invention concerns a method of increasing oil content in an oleaginous yeast comprising:

a) engineering the oleaginous yeast to overexpress a protein selected from the group consisting of:
   (i) a Yap1 transcription factor;
   (ii) a protein that is capable of activating the transcription factor;
   (iii) a combination of (a) and (b); and,
b) growing the oleaginous yeast under suitable conditions to result in increased oil content when compared to the oil content of a non-transgenic oleaginous yeast.

BRIEF DESCRIPTION OF THE DRAWINGS AND SEQUENCE DESCRIPTIONS

FIG. 1 is a diagram of the mechanism by which *Saccharomyces cerevisiae* GPX3 ["ScGPX3"] activates *S. cerevisiae* YAP1 ["ScYap1"]. ScGPX3 comprises Cys36 and Cys82, which either form an inter-molecular disulfide bond (—S—S—) or are reduced to contain thiol groups (—SH). ScYap1 comprises a N-terminal and a C-terminal Cys-rich domain (each shown in black); Cys 303, Cys310 and Cys315 and Cys598, Cys620 and Cys629 within these Cys-rich domains are shown as 6 vertical black lines. The thiol group (—SH) of Cys36 ScGpx3 reacts with $H_2O_2$, resulting in the release of water and formation of a suplhenic acid (—SOH). The —SOH then condenses with the —SH of Cys598 of ScYap1 (reduced form), forming an inter-molecular disulfide bond (—S—S—), which is then converted into an intra-molecular disulfide bond between Cys303 and Cys598 of ScYap1, thereby producing a conformational change in the oxidized ScYap1 protein.

FIG. 2A-B show a sequence comparison between ScYAP1 (SEQ ID NO:2) and YlYAP1 (SEQ ID NO:4). Underlined, bolded basic amino acids at positions 69-115 of ScYAP1 (corresponding to positions 115-166 of YlYAP1) represent the basic region of the bZIP domain for DNA binding. Bold leucine residues, shown with a star over the alignment, at positions 87, 94, 108, and 115 of ScYAP1 (corresponding to positions 138, 145, 159, and 166 of YlYAP1) are the leucine zipper motif of the bZIP domain. Boxed cysteine residues at positions 303, 310, 315, 598, 620 and 629 of ScYAP1 (corresponding to positions 309, 316, 483, 505 and 514 of YlYap1) are important (or likely important) for inter- and intra-molecular interactions.

Figure 3:
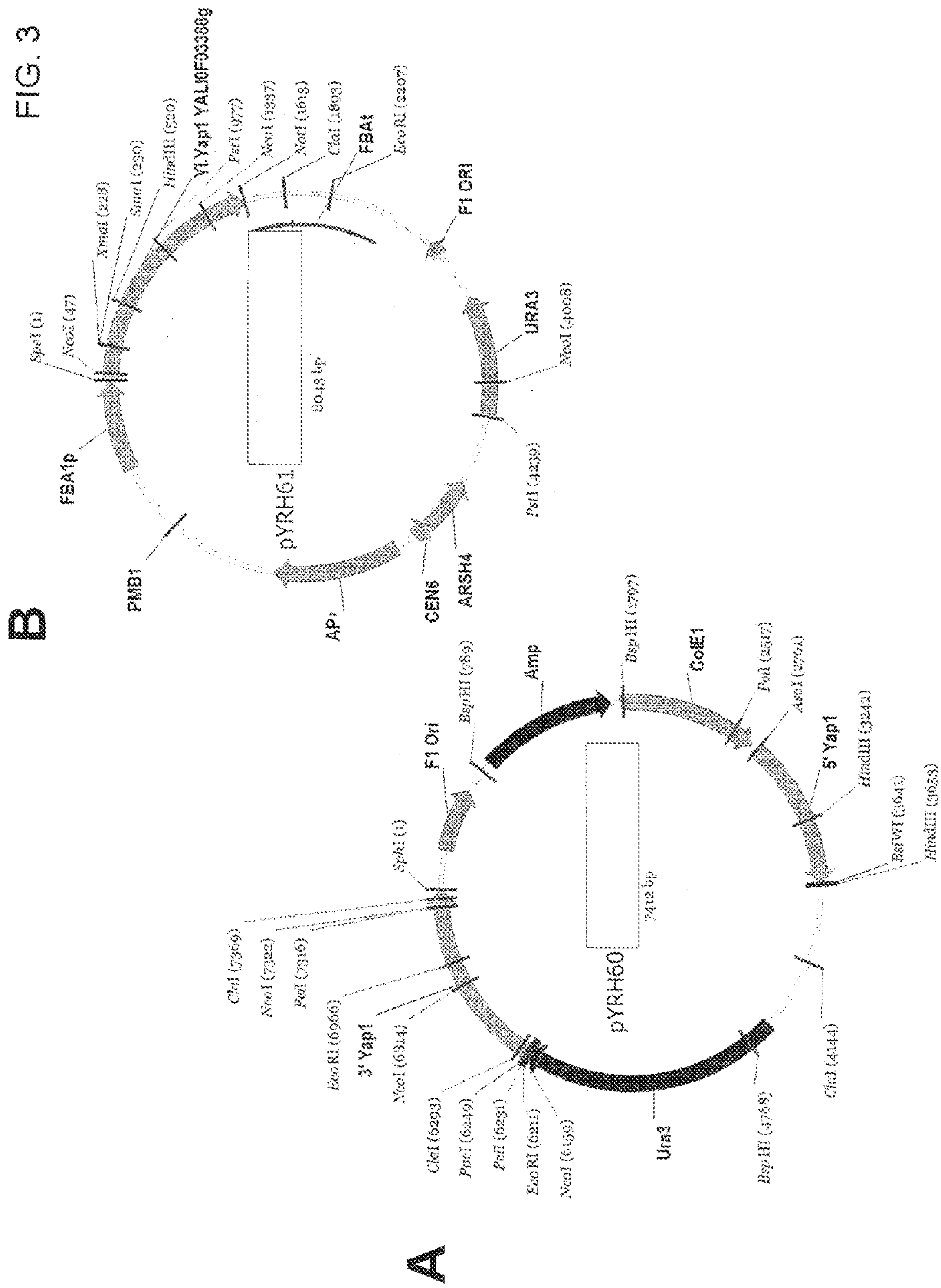

FIG. 3 provides plasmid maps for the following: (A) pYRH60; and, (B) pYRH61.

FIG. 4 shows $H_2O_2$ sensitivity assay results on YPD plates under increasing $H_2O_2$ concentrations, i.e., from 0 mM to 50 mM $H_2O_2$. (A) compares growth of *Y. lipolytica strains* Y4184 (control) and Y4184U (yap1Δ) cells. (B) compares growth of *S. cerevisiae* strains BY4743 (control) and BY4743 (yap1Δ) cells, transformed with either plasmid pRS316 (control) or pYRH61.

Figure 5:
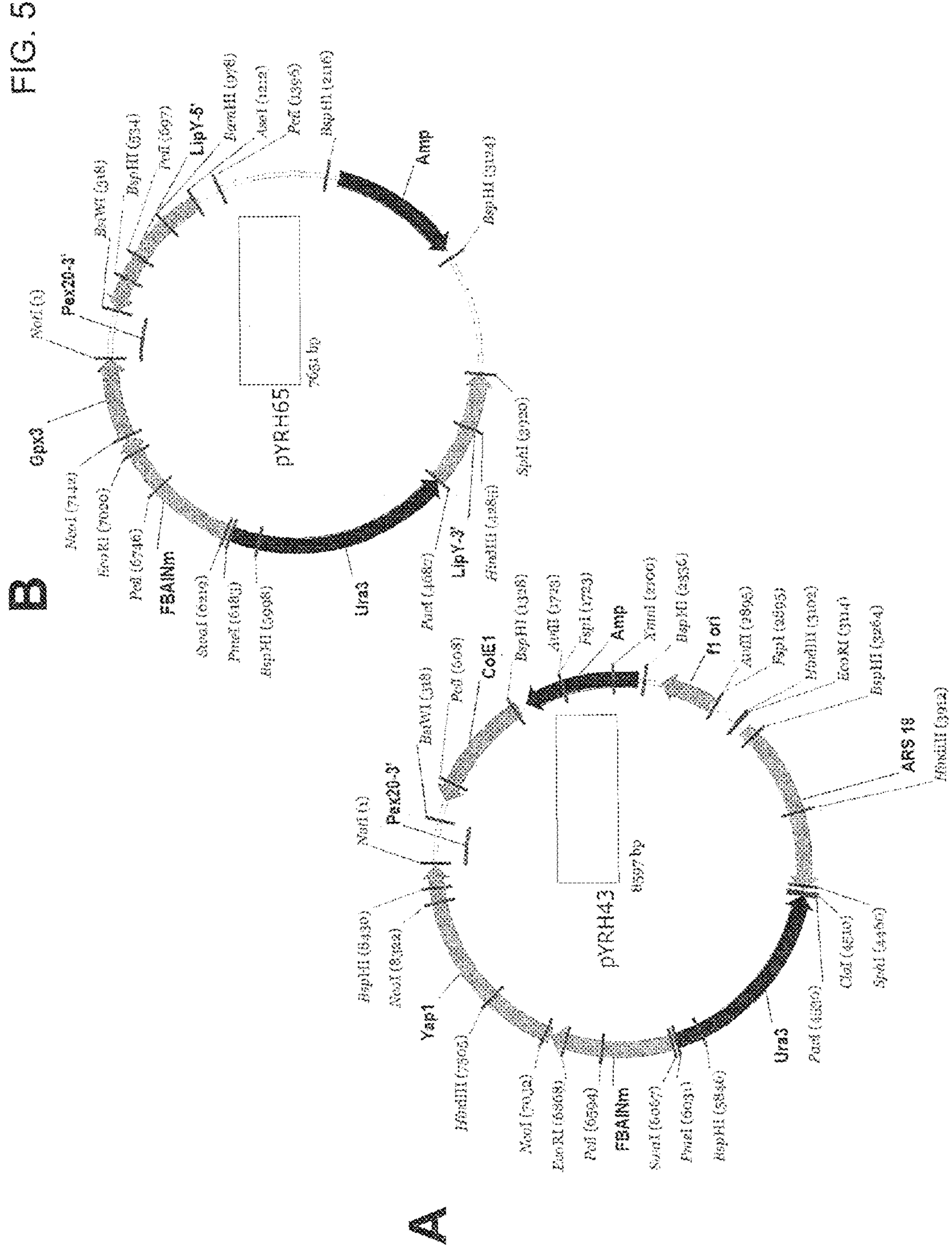

FIG. 5 provides plasmid maps for the following: (A) pYRH43; and, (B) pYRH65.

FIG. 6 is a sequence comparison between ScGPX3 (SEQ ID NO:26) and YlGPX3 (SEQ ID NO:28). Boxed cysteine residues at positions 36, 64 and 82 of ScGpx3 (corresponding to positions 42, 70 and 88 of YlGpx3) are important (or likely important) for inter- and intra-molecular interactions.

FIG. 7 is a sequence comparison between ScTsa1 (SEQ ID NO:34) and YlTsa1 (SEQ ID NO:36). Boxed cysteine residues at positions 48 and 171 of ScTsa1 (corresponding to positions 48 and 169 of YlTsa1) are important (or likely important) for inter- and intra-molecular interactions.

FIG. 8A-B show a sequence comparison between ScYbp1 (SEQ ID NO:38) and YlYbp1 (SEQ ID NO:40).

FIG. 9A-E show a sequence comparison between ScYbp1 (SEQ ID NO:38), YlYbp1 (SEQ ID NO:40), the *Candida glabrata* Ybp1 ["CgYbp1"] (SEQ ID NO:43), the *Kluyveromyces lactis* NRRL Y-1140 Ybp1 ["KlYbp1"] (SEQ ID NO:44), the *Scheffersomyces stipitis* CBS 6054 Ybp1 ["SsYbp1"] (SEQ ID NO:45), the *Zygosaccharomyces rouxii* CBS 732 Ybp1 ["ZrYbp1"] (SEQ ID NO:46), and the *Candida albicans* SC5314 Ybp1 ["CaYbp1"] (SEQ ID NO:47).

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-47 are ORFS encoding genes, proteins (or portions thereof), primers or plasmids, as identified in Table 1.

TABLE 1

Summary Of Nucleic Acid And Protein SEQ ID Numbers

| Description | Nucleic acid SEQ ID NO. | Protein SEQ ID NO. |
|---|---|---|
| *Saccharomyces cerevisiae* Yap1 (GenBank Accession No. NM_001182362) | 1 (1953 bp) | 2 (650 AA) |
| *Yarrowia lipolytica* Yap1 (GenBank Accession No. XM_504945) | 3 (1605 bp) | 4 (534 AA) |

TABLE 1-continued

Summary Of Nucleic Acid And Protein SEQ ID Numbers

| Description | Nucleic acid SEQ ID NO. | Protein SEQ ID NO. |
|---|---|---|
| Plasmid pYRH60 | 5 (7412 bp) | — |
| Plasmid pYPS161 | 6 (7966 bp) | — |
| *Yarrowia lipolytica* Yap1 promoter region | 7 (940 bp) | — |
| Primers YI-EF-1214F, YI-EF-1270R, YAP1-346F and YAP1-409R | 8-11 | — |
| Primer YL-EF-MGB-1235T containing reporter dye 5'-6-FAM and quencher 3'-TAMRA | 12 | — |
| Primer YAP1-366T containing reporter dye 5'-6-FAM and quencher 3'-TAMRA | 13 | — |
| Plasmid pYRH61 | 14 (8043 bp) | — |
| Primers Yl.Yap1-F-SpeI and Yap1-R | 15-16 | — |
| *Saccharomyces cerevisiae* FBA1 promoter region | 17 (601 bp) | — |
| *Saccharomyces cerevisiae* FBA1 terminator region | 18 (1022 bp) | — |
| Plasmid pRS316 | 19 (4887 bp) | — |
| Plasmid pYRH43 | 20 (8597 bp) | — |
| Primer Yap1-F | 21 | — |
| Primers ef-324F and ef-392R | 22, 23 | — |
| Primer ef-345T containing reporter dye 5'-6-FAM and quencher 3'- TAMRA | 24 | |
| *Saccharomyces cerevisiae* GPX3 (GenBank Accession No. NM_001179559) | 25 (492 bp) | 26 (163 AA) |
| *Yarrowia lipolytica* GPX3 (GenBank Accession No. XM_503454) | 27 (507 bp) | 28 (168 AA) |
| Plasmid pYRH65 | 29 (7651 bp) | — |
| Primers GPX3-F and GPX3-R | 30-31 | — |
| *Yarrowia lipolytica* Yap1 terminator region | 32 (1164 bp) | — |
| *Saccharomyces cerevisiae* Tsa1 (GenBank Accession No. NP_013684) | 33 (591 bp) | 34 (196 AA) |
| *Yarrowia lipolytica* Tsa1 (GenBank Accession No. XM_500915) | 35 (591 bp) | 36 (196 AA) |
| *Saccharomyces cerevisiae* Ybp1 (GenBank Accession No. NP_009775) | 37 (2025 bp) | 38 (674 AA) |
| *Yarrowia lipolytica* Ybp1 (GenBank Accession No. XM_500469) | 39 (2025 bp) | 40 (674 AA) |
| Mutant delta-5 desaturase motif: HPGs | — | 41 |
| Mutant delta-5 desaturase motif: HaGG | — | 42 |
| *Candida glabrata* Ybp1 (GenBank Accession No. CAG61477.1) | — | 43 (655 AA) |
| *Kluyveromyces lactis* NRRL Y-1140 Ybp1 (GenBank Accession No. XP_452453.1) | — | 44 (702 AA) |
| *Scheffersomyces stipitis* CBS 6054 Ybp1 (GenBank Accession No. XP_001386941.2) | — | 45 (673 AA) |
| *Zygosaccharomyces rouxii* CBS 732 Ybp1 (GenBank Accession No. XP_002495870.1) | — | 46 (664 AA) |
| *Candida albicans* SC5314 Ybp1 (GenBank Accession No. XP_722236.1) | — | 47 (664 AA) |

DETAILED DESCRIPTION OF THE INVENTION

All patents, patent applications, and publications cited herein are incorporated by reference in their entirety.

In this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

"Polyunsaturated fatty acid(s)" is abbreviated as "PUFA(s)".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

"Weight percent" is abbreviated as "wt %".

"Reactive oxygen species" is abbreviated as "ROS".

"Hydrogen peroxide" is abbreviated as "$H_2O_2$".

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

A "transcription factor" refers to a protein (or the DNA encoding that protein) which interacts with a DNA regulatory element to affect expression of a structural gene or expression of a second regulatory gene. More specifically, the transcription factor (either alone or in a complex with other proteins) affects transcription of DNA to mRNA, by e.g., activation or repression of transcription initiation. A transcription factor may comprise one or more DNA-binding domains which attach to specific sequences of DNA adjacent to the genes that they regulate.

"Yap1 transcription factor activity" refers to activity that occurs as a result of a Yap1 transcription factor, a transcriptional regulator of the AP-1 family involved in a cellular pathway that controls the oxidative stress response. Increased Yap1 transcription factor activity results in regulation of a family of proteins, which typically enables increased tolerance to ROS (e.g., when $H_2O_2$ stress is encountered). According to the present invention described herein, increased Yap1 transcription factor activity results in increased oil content.

A "Yap1 transcription factor" refers to a transcription factor having Yap1 transcription factor activity. In general, such a protein should have: (a) a bZIP leucine zipper motif; (b) an N-terminal Cys-rich domain comprising a sequence of at least two cysteine residues that are separated by at least six (6) amino acids; and, (c) a C-terminal Cys-rich domain comprising a sequence of at least two cysteine residues that are separated by at least eight (8) amino acids.

A "bZIP leucine zipper motif" is characterized as comprising: (i) a basic DNA binding region spanning approximately fourteen to sixteen amino acids (i.e., comprising arginine and lysine residues); and, (ii) an adjacent leucine-rich zipper region (i.e., comprising evenly spaced leucine residues allowing dimerization) (Hurst, N.C. Transcription factors 1: bZIP proteins. *Protein Profile,* 2:101-168 (1995)). Typically, the leucine residues are spaced at seven amino acid intervals; although other hydrophobic amino acids such as methionine, isoleucine, valine and phenylalanine have been reported to form zippers in combination with leucine.

The term "ScYAP1" (SEQ ID NO:1; GenBank Accession No. NM_001182362.1) refers to a Yap1 transcription factor of the AP-1 family isolated from *Saccharomyces cerevisiae* 5288c, encoded by SEQ ID NO:2. As annotated in GenBank, ScYAP1 is required for oxidative stress tolerance, and is activated by $H_2O_2$ through the multistep formation of disulfide bonds and transit from the cytoplasm to the nucleus. ScYAP1 also mediates resistance to cadmium.

The term "YlYAP1" (SEQ ID NO:4; YALI0F03388p; GenBank Accession No. XP_504945) refers to a Yap1 transcription factor isolated from *Yarrowia lipolytica*, encoded by SEQ ID NO:3 herein.

The term "a protein that is capable of activating the Yap1 transcription factor" refers to a protein that interacts with the Yap1 transcription factor in a manner that facilitates oxidation of the Yap1 transcription factor, such that the transcription factor comprises at least one intra-molecular disulfide bond and is thus in an "activated state". Preferred proteins that are capable of activating the Yap1 transcription factor include Yap1 binding protein (Ybp1) and the peroxiredoxin proteins, Gpx3 and Tsa1, although this should not be construed as limiting to the invention herein.

"Yap1 binding protein" or "Ybp1" refers to a binding protein that binds to a Yap1 transcription factor. As described in Gulshan, K. et al. (*J. Biol. Chem.,* 286(39):34071-34081 (2011)), Yap1 and Ybp1 are likely to directly interact in the cell, but further localization of the sites or domains of interaction has not been achieved.

The term "ScYbp1" (SEQ ID NO:38; GenBank Accession No. NP_009775.1) refers to a Yap1 binding protein isolated from *Saccharomyces cerevisiae* 5288c, encoded by SEQ ID NO:37 herein (Veal, E. A. et al., *J Biol Chem.,* 278(33): 30896-30904 (2003); Gulshan, K. et al., supra). As annotated in GenBank, ScYbp1 functions as a "protein required for oxidation of specific cysteine residues of the transcription factor Yap1p, resulting in the nuclear localization of Yap1p in response to stress".

The term "YlYbp1" (SEQ ID NO:40; YALI0B03762g; GenBank Accession No. XP_500469.1) refers to a Yap1 binding protein isolated from *Yarrowia lipolytica*, encoded by SEQ ID NO:39 herein.

A "peroxiredoxin protein" or "Prx protein" comprises redox-active cysteine residues. During catalysis, the peroxidatic cysteine is oxidized (e.g., by $H_2O_2$) to a sulfenic acid, which condenses with a resolving cysteine residue to form a disulfide (wherein the resolving cysteine residue is either within the same Prx molecule or within another Prx molecule, resulting in dimer formation). This disulfide bond is reduced by thioredoxin to regenerate the active Prx. Thus, Prx proteins are active in a redox cycle, accepting electrons from NADPH via thioredoxin and thioredoxin reductase. As defined by T. Tachibana et al. (*J. Biol. Chem.,* 284 (7):4464-4472 (2009)), proteins that show thioredoxin-dependent peroxidase activity in budding yeast include five Prx family proteins [i.e., Tsa1, Tsa2, Prx1, Ahp1, Dot5] and two glutathione peroxidase (Gpx)-like proteins [i.e., Gpx2, Gpx3], although "Prx" will be used herein to refer to both the Prx proteins and the Gpx-like proteins. Preferred Prx proteins that are capable of activating the Yap1 transcription factor include Gpx3 and Tsa1.

The term "ScGpx3" (SEQ ID NO:26; GenBank Accession No. NM_001179559.1; E.C. 1.11.1.15) refers to a thiol peroxidase isolated from *Saccharomyces cerevisiae* S288c, encoded by SEQ ID NO:25. As annotated in GenBank, ScGpx3 functions as a hydroperoxide receptor to sense intracellular $H_2O_2$ levels and transduce a redox signal to the Yap1p transcription factor.

The term "YlGpx3" (SEQ ID NO:28; YALI0E02310p; GenBank Accession No. XP_503454) refers to a thiol peroxidase isolated from *Yarrowia lipolytica*, encoded by SEQ ID NO:27 herein.

The term "ScTsa1" (SEQ ID NO:34; E.C. 1.11.1.15; GenBank Accession No. NP_013684) refers to a thioredoxin peroxidase isolated from *Saccharomyces cerevisiae* S288c, encoded by SEQ ID NO:33 herein (Trotter, E. W. et al., *Biochem J.,* 412(1):73-80 (2008)). As annotated in GenBank, ScTsa1 is of the peroxiredoxin (PRX) 2-Cys subfamily, wherein peroxiredoxins function as "thiol-specific antioxidant (TSA) proteins, which confer a protective role in cells through its peroxidase activity by reducing $H_2O_2$, peroxynitrite, and organic hydroperoxides".

The term "YlTsa1" (SEQ ID NO:36; YALI0B15125g; GenBank Accession No. XP_500915.1) refers to a thioredoxin peroxidase isolated from *Yarrowia lipolytica*, encoded by SEQ ID NO:35 herein.

Generally, the term "oleaginous" refers to those organisms that tend to store their energy source in the form of oil (Weete, In: Fungal Lipid Biochemistry, 2nd Ed., Plenum, 1980). During this process, the cellular oil content of oleaginous microorganisms generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)). For the purposes of the present application, the term "oleaginous" refers to those microorganisms that can accumulate at least about 25% of their dry cell weight ["DCW"] as oil.

The term "oleaginous yeast" refers to those oleaginous microorganisms classified as yeasts that can make oil, i.e., wherein oil can accumulate in excess of about 25% of their DCW. Examples of oleaginous yeast include, but are no means limited to, the following genera: *Yarrowia, Candida, Rhodotorula, Rhodosporidium, Cryptococcus, Trichosporon* and *Lipomyces*. The ability to accumulate oil in excess of about 25% of the DCW of the yeast may be through efforts of recombinant engineering or through the natural abilities of the organism.

The term "transgenic oleaginous yeast" generically refers to an oleaginous yeast that contains a foreign or heterologous nucleic acid fragment as a result of a transformation procedure. However, for the purposes herein, the term "transgenic oleaginous yeast" will specifically refer to an oleaginous yeast that contains a foreign or heterologous nucleic acid fragment(s) as a result of a transformation procedure, wherein expression of the foreign or heterologous nucleic acid(s) results in increased Yap1 transcription factor activity in the oleaginous yeast. Thus, for example, a transgenic oleaginous yeast of the invention herein may be genetically engineered to overexpress a chimeric gene encoding either a Yap1 transcription factor or a protein that is capable of activating the Yap1 transcription factor, wherein the Yap1 transcription factor or the protein that is capable of activating the Yap1 transcription is either a native gene or a foreign gene.

In contrast, a non-transgenic oleaginous yeast herein will refer to an oleaginous yeast having a genotype identical to the transgenic oleaginous yeast to which it is compared, with the exception that the non-transgenic oleaginous yeast has not been transformed with the foreign or heterologous nucleic acid(s) that results in increased Yap1 transcription factor activity in the transgenic oleaginous yeast and thus lacks this particular foreign or heterologous nucleic acid(s). To be clear, the non-transgenic oleaginous yeast of the invention herein may express at least one foreign gene or heterologous nucleic acid(s), but this does not result in increased Yap1 transcription factor activity.

"Transformation" refers to the transfer of a nucleic acid molecule into a host organism. The nucleic acid molecule may be a plasmid that replicates autonomously; or, it may integrate into the genome of the host organism. Host organisms containing the transformed nucleic acid fragments are referred to as "transgenic" or "recombinant" or "transformed" organisms or "transformants".

The term "'lipids" refer to any fat-soluble (i.e., lipophilic), naturally-occurring molecule. A general overview of lipids is provided in U.S. Pat. Appl. Pub. No. 2009-0093543-A1 (see Table 2 therein).

The term "oil" refers to a lipid substance that is liquid at 25° C.; the oil and is hydrophobic but is soluble in organic solvents. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of fatty acids in the total lipid will correspond with an increase or decrease in the concentration of fatty acids in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain long chain polyunsaturated and saturated fatty acids, as well as shorter chain saturated and unsaturated fatty acids.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including, e.g., the phosphatidylcholine and the phosphatidylethanolamine fractions) but not free fatty acids.

The terms "total lipid content" and "oil content" are used interchangeably herein, to refer to the lipid/oil content of cells as a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

Oil content of the transgenic oleaginous yeast of the invention must be compared to the oil content of the non-transgenic oleaginous yeast of the invention under comparable conditions of growth (e.g., type/amount of carbon source, type/amount of nitrogen source, carbon-to-nitrogen ratio, amount of mineral ions, oxygen level, growth temperature, pH, length of the biomass production phase, length of the oil accumulation phase and the time/method of cell harvest).

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in polymerase chain reaction ("PCR") in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Y. lipolytica* is provided in U.S. Pat. No. 7,125,672, incorporated herein by reference.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene (or "exogenous" gene) refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences", "transcription terminator" and "terminator" are used interchangeably herein and refer to DNA sequences located 3' downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "operably linked" refers to the association of nucleic acid sequences on a single nucleic acid fragment so that the function of one is affected by the other. For example, a promoter is operably linked with a coding sequence when it is capable of effecting the expression of that coding sequence. That is, the coding sequence is under the transcriptional control of the promoter. Coding sequences can be operably linked to regulatory sequences in sense or antisense orientation.

The term "expression", as used herein, refers to the transcription and stable accumulation of sense (mRNA) or antisense RNA. Expression may also refer to translation of mRNA into a polypeptide.

"Stable transformation" refers to the transfer of a nucleic acid fragment into the genome of a host organism, including both nuclear and organellar genomes, resulting in genetically stable inheritance (i.e., the nucleic acid fragment is "stably integrated"). In contrast, "transient transformation" refers to the transfer of a nucleic acid fragment into the nucleus, or DNA-containing organelle, of a host organism resulting in gene expression without integration or stable inheritance.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, and may be linear or circular, of a single- or double-stranded DNA or RNA, derived from any source, in which a number of nucleotide sequences have been joined or recombined into a unique construction that is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., an open reading frame ("ORF")); and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.* 215:403-410 (1990)); 3) DNASTAR (DNASTAR, Inc. Madison, Wis.); 4) Sequencher (Gene Codes Corporation, Ann Arbor, Mich.); and 5) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Sequence identity" or "identity" in the context of nucleic acid or polypeptide sequences refers to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: N.Y. (1991).

Sequence alignments and percent identity or similarity calculations may be determined using a variety of comparison methods designed to detect homologous sequences.

Multiple alignment of sequences can be performed using the "Clustal method of alignment" which encompasses several varieties of the algorithm including the "ClustalV method of alignment" and the "ClustalW method of alignment" (described by Higgins and Sharp, *CABIOS,* 5:151-153 (1989); Higgins, D. G. et al., *Comput. Appl. Biosci.,* 8:189-191 (1992)) and found in the MegAlign™ (version 8.0.2) program, above. After alignment of the sequences using either Clustal program, it is possible to obtain a "percent identity" by viewing the "sequence distances" table in the program.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "conserved domain method of analysis" refers to the "Identify Conserved Domains" tool of the National Center for Biotechnology Information ["NCBI"], which detects conserved domains within a protein sequence using a CD-search (Marchler-Bauer, A. and S. H. Bryant, *Nucleic Acids Res.,* 32(W)327-331 (2004); Marchler-Bauer, A. et al., *Nucleic Acids Res.,* 37(D)205-210 (2009); and Marchler-Bauer, A. et al., *Nucleic Acids Res.,* 39(D)225-229 (2011)).

The term "kinetochor_Ybp2 super family" refers to the Pfam08568 family of proteins described in the Pfam protein database (Finn, R. D. et al., *Nucleic Acids Res.,* 36 (Database issue):D281-D288 (2008)).

Standard recombinant DNA and molecular cloning techniques used herein are well known in the art and are described by Sambrook, J., Fritsch, E. F. and Maniatis, T., Molecular Cloning: A Laboratory Manual, $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

The activator protein 1 ["AP-1"] is a transcription factor which is a heterdimeric protein composed of subunits that are the products of at least three different proto-oncogene families: the Jun (c-Jun, v-Jun, JunB, JunD), Fos (c-Fos, v-Fos, FosB, FosB2, Fra-1, Fra-2) and activating transcription factor (B-ATF, ATF2, ATF3/LRF1) families. AP-1 regulates gene expression in response to a variety of stimuli, including cytokines, growth factors, stress, and bacterial and viral infections; thus, AP-1 controls a number of cellular processes by upregulating transcription of genes containing the AP-1 recognition element, having the sequence set forth as TGA(C/G)TCA. AP-1 binds to this DNA sequence via a basic amino acid region, while the dimeric structure is formed by a leucine zipper.

YAP1 is the *Saccharomyces cerevisiae* equivalent of AP-1, and has been concluded to function as the master transcription factor for the oxidative stress response (Moye-Rowley et al., *Genes Dev.,* 3:283-292 (1989)) (SEQ ID NO:2). Structurally, this protein possesses a bZip structural motif consisting of a leucine-rich zipper region and an adjacent basic region (i.e., comprising arginine and lysine residues), as well as an N-terminal Cys-rich domain (i.e., Cys303, Cys310 and Cys315) and a C-terminal Cys-rich domain (i.e., Cys598, Cys620 and Cys629).

Functionally, at least one intra-molecular disulfide bond forms between Cys303 and Cys598 in response to $H_2O_2$ stress, thereby causing a multi-step conformational change in Yap1 and nuclear accumulation of Yap1 (due to modifications to the nuclear export signal). In this active oxidized form, Yap1 controls the expression of a large regulon of at least 32 different proteins, including cellular antioxidants and enzymes of the glutathione and pentose phosphate pathways (Lee, J. et al., *J. Biol. Chem.,* 274:16040-16046 (1999)). Deactivation of Yap1 occurs by enzymatic reduction with Yap1-controlled thioredoxins, thus providing a mechanism for autoregulation.

The oxidation of the *S. cerevisiae* Yap1 protein does not occur directly in response to $H_2O_2$; instead, a constitutively expressed thiol peroxidase protein (e.g., Gpx3; SEQ ID NO:26) transduces the $H_2O_2$ signal and is responsible for catalyzing the formation of the intra-molecular disulfide bond (s) within Yap1 (Inoue et al., *J. Biol. Chem.,* 274:27002-27009 (1999); Delaunay, A., et al., *Cell,* 111:471-481 (2002)). Cys36 of this glutathione peroxidase (Gpx)-like protein initially bridges Cys598 of Yap1 by a disulfide bond, which is converted into the Yap1 intra-molecular disulfide bond (FIG. 1, recreated from Tachibana, T. et al., *J. Biol. Chem.,* 284:4464-4472 (2009); Okazaki et al., *Mol. Cell,* 27:675-688 (2007)). Gpx3 proteins not reacting with Yap1 are able to reduce $H_2O_2$ directly to water, resulting in formation of an intra-molecular disulfide bond between Cys36 and Cys82 of the Gpx3 protein. A Gpx3-independent pathway for Yap1 activation is also known (Azevedo, D., et al., *Free Radic. Biol, Med.,* 35:889-900 (2003)).

In addition to Gpx3, a suite of other peroxiredoxin (Prx) proteins comprising at least one redox-active cysteine residue may be capable of activating the Yap1 transcription factor (via direct or indirect means).

Specifically, T. Tachibana et al. (*J. Biol. Chem.,* 284 (7): 4464-4472 (2009)) identifies five Prx family proteins [i.e., Tsa1, Tsa2, Prx1, Ahp1, Dot5] and two Gpx-like proteins [i.e., Gpx2, Gpx3] as having thioredoxin-dependent peroxidase activity in budding yeast (all of which will be referred to generically herein as Prx proteins). The exact nature by which these proteins interact with Yap1 continues to be investigated. Tachibana, T. et al. (*J. Biol. Chem.,* 284:4464-4472 (2009)) report that *S. cerevisiae* Tsa1 (SEQ ID NO:34) interacts with Yap1 in a manner similar to that of Gpx3, based on Cys-48 and Cys-171.

Although the exact mechanism by which Yap1 and Ybp1 interact is unknown, Ybp1 has been demonstrated to also affect activation of the Yap1 transcription factor. Gulshan, K. et al. (*J. Biol. Chem.,* 286(39):34071-34081 (2011)) studied the interaction between Ybp1 and Yap1 in both *S. cerevisiae* and *Candida glabrata*; they report that "Yap1 and Ybp1 are likely to directly interact in the cell . . . efforts to further localize the interaction motifs of these two proteins were unsuccessful". It is hypothesized therein that the interaction of Yap1 and Ybp1 likely involves multiple, low-affinity interactions while oxidation of Yap1 likely triggers release of the folded protein from its Ybp1 partner. Ybp1 overproduction in *S. cerevisiae* was also reported to lead to increased $H_2O_2$ tolerance.

Mechanisms of oxidative stress response are relatively well conserved (although there are some differences among species) and Yap1p homologs, such as Cap1p in *Candida albicans* and Pap1p in *Schizosaccharomyces pombe*, are also known to transcriptionally regulate some anti-oxidant genes in response to oxidative stress (Ikner, A. and K. Shiozaki, *Mutat. Res.*, 569:13-27 (2005)). However, the means by which the oxidative stress response functions in oleaginous yeast is much less well characterized. Oleaginous yeast are naturally capable of oil synthesis and accumulation, wherein the total oil content can comprise greater than about 25% of the dry cell weight ["DCW"], more preferably greater than about 30% of the DCW, more preferably greater than about 40% of the DCW, more preferably greater than about 50% of the DCW, and most preferably greater than about 60% of the DCW (wherein this rate of oil accumulation is prior to any efforts to increase the native Yap1 transcription factor activity in the yeast, according to the invention herein). Various yeast are naturally classified as oleaginous; however, in alternate embodiments, a non-oleaginous organism can be genetically modified to become oleaginous, e.g., yeast such as *Saccharomyces cerevisiae* (see, Int'l App. Pub. No. WO 2006/102342).

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (such as, for example, but not limited to the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Like other organisms that conduct aerobic metabolism and thus rely on defenses against ROS (created via incomplete reduction of oxygen to water during respiration), obligatory aerobic oleaginous yeast also require various means to sense and respond to oxidative stress. In the present invention, homologs of *S. cerevisiae* Yap1, Gpx3, Tsa1 and Ybp1 genes have been identified in the oleaginous yeast, *Yarrowia lipolytica*, as summarized in the Table below. Alignments of each pair of proteins were created with CLUSTAL W (1.81) multiple sequence alignment (Thompson J. D., et al., *Nucleic Acids Res.* 22:4673-4680 (1994)).

TABLE 2

Yap1, Gpx3, Tsa1 And Ybp1 Homologs

| | *S. cerevisiae* | *Yarrowia lipolytica* | Percent Identity | Alignment |
|---|---|---|---|---|
| Yap1 | SEQ ID NO: 2 (GenBank Accession No. NM_001182362) | SEQ ID NO: 4 (YALI0F03388p) | ~21.1% | FIG. 2A-B |
| Gpx3 | SEQ ID NO: 26 (GenBank Accession No. NP_012303) | SEQ ID NO: 28 (YALI0E02310p) | ~71.8% | FIG. 6 |
| Tsa1 | SEQ ID NO: 34 (GenBank Accession No. NP_013684) | SEQ ID NO: 36 (YALI0B15125g) | ~74.0% | FIG. 7 |

TABLE 2-continued

Yap1, Gpx3, Tsa1 And Ybp1 Homologs

| | *S. cerevisiae* | *Yarrowia lipolytica* | Percent Identity | Alignment |
|---|---|---|---|---|
| Ybp1 | SEQ ID NO: 38 (GenBank Accession No. NP_009775.1) | SEQ ID NO: 40 (YALI0B03762g) | ~16.3% | FIG. 8A-B, FIG. 9A-E |

Surprisingly, when the *Y. lipolytica* Yap1 ["YlYap1"] and Gpx3 ["Y1Gpx3"] proteins were over-expressed to result in increased Yap1 transcription factor activity, the transgenic *Y. lipolytica* was found to have increased oil content (measured as TFAs % DCW), as compared to the oil content in a non-transgenic *Y. lipolytica.*

Thus, the instant invention concerns a transgenic oleaginous yeast having increased oil content comprising increased Yap1 transcription factor activity wherein the increased oil content is compared to the oil content of a non-transgenic oleaginous yeast.

It is hypothesized herein that increased oil content is observed in the transgenic oleaginous yeast since increased Yap1 transcription factor activity provides increased resistance to oxidative stresses. One beneficial outcome of this increased resistance to oxidative stresses is increased protection against lipid peroxidation, which thereby results in increased oil/lipid content in the transgenic oleaginous yeast. Among lipid molecules, PUFAs are particularly sensitive to ROS, and it was shown that the susceptibility of fatty acids to lipid peroxidation increased with the degree of fatty acyl chain unsaturation (Porter, N. A. et al., *Lipids*, 30:277-290 (1995)). The lipid peroxidation was shown to affect cell viability via generation of polar hydroperoxides which affect membrane integrity (Howlett, N. G. and S. V. Avery, *Appl. Microbiol. Biotechnol.*, 48(4):539-545 (1997); Howlett, N. G. and S. V. Avery, *Appl. Environ. Microbiol.*, 63(8):2971-2976 (1997)). However, no study has previously shown the effect of the Yap1 transcription factor overexpression in oil content.

Preferably, the transgenic oleaginous yeast of the present invention will be capable of producing at least 10-25% greater oil content than the oil content of a non-transgenic oleaginous yeast. More preferably, the increase in oil content is at least 25-45% greater, and most preferably the increase in oil content is at least 45-65% greater than the oil content of a non-transgenic oleaginous yeast. Thus, those skilled in the art will appreciate that the increase in oil content can be any integer percentage (or fraction thereof) from 10% up to and including 100% or greater, i.e., specifically, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% increase in oil content when compared to the oil content of a non-transgenic oleaginous yeast.

As described above, the microbial oil will comprise triacylglycerols (comprising long chain polyunsaturated and/or saturated fatty acids, as well as shorter chain saturated and/or unsaturated fatty acids), as well as other neutral lipids, phospholipids and free fatty acids.

In one embodiment, the increased Yap1 transcription factor activity in the transgenic oleaginous yeast having increased oil content results from overexpressing a Yap1 transcription factor. A suitable Yap1 transcription factor will preferably comprise a nucleotide sequence encoding a polypeptide having transcription factor activity and comprising:

a) a bZIP leucine zipper motif;

b) an N-terminal Cys-rich domain comprising a sequence of at least two cysteine residues that are separated by at least 6 amino acids; and, c) a C-terminal Cys-rich domain comprising a sequence of at least two cysteine residues that are separated by at least 8 amino acids.

A bZIP leucine zipper motif comprises a basic DNA binding region spanning approximately fourteen to sixteen amino acids (i.e., comprising arginine and lysine residues) and an adjacent leucine-rich zipper region (i.e., comprising evenly spaced leucine residues allowing dimerization) (Hurst, N. C., *Protein Profile,* 2:101-168 (1995)).

One preferred Yap1 transcription factor is the *Yarrowia lipolytica* Yap1 ["YlYap1"] polypeptide sequence, as set forth in SEQ ID NO:4. In alternate embodiments, the ScYAp1 (SEQ ID NO:2) or any of the sequences set forth in Table 4 (Example 1), or homologs or codon-optimized derivatives thereof, may be used in the present invention.

In another embodiment, the increased Yap1 transcription factor activity in the transgenic oleaginous yeast having increased oil content results by increasing the interaction between the transcription factor and a protein that is capable of activating the transcription factor (i.e., by overexpressing the protein capable of activating the transcription factor itself). Preferably, the protein that is capable of activating the transcription factor is selected from the group consisting of: Gpx3, Ybp1 and Tsa1.

For example, a suitable Gpx3 protein will comprise:

a) a nucleotide sequence encoding a polypeptide capable of interacting with the Yap1 transcription factor to increase Yap1 transcription factor activity, wherein the polypeptide has at least 70% amino acid identity, based on the BLASTP method of alignment, when compared to a sequence selected from the group consisting of SEQ ID NO:26 [ScGpx3] or SEQ ID NO:28 [YlGpx3];

b) a nucleotide sequence encoding a polypeptide capable of interacting with the Yap1 transcription factor to increase Yap1 transcription factor activity, wherein the nucleotide sequence has at least 70% sequence identity, based on the BLASTN method of alignment, when compared to a sequence selected from the group consisting of SEQ ID NO:25 [ScGpx3] or SEQ ID NO:27 [YlGpx3]; or c) a complement of the nucleotide sequence of (a) or (b), wherein the complement and the nucleotide sequence consist of the same number of nucleotides and are 100% complementary.

A suitable Gpx3 protein will comprise at least one redox-active cysteine residue, such as Cys36 and Cys82 of ScGpx3 (SEQ ID NO:26).

Preferably, the polypeptide sequence encoding Gpx3 is set forth in SEQ ID NO:28 ("YlGpx3"). In alternate embodiments, the polypeptide sequence encoding Gpx3 has at least 70% sequence identity based on the CLUSTALW method of alignment, when compared to SEQ ID NO:26 or SEQ ID NO:28, i.e., the polypeptide may have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity when compared thereto. In alternate embodiments, the sequences set forth in Table 9 (Example 5), or homologs or codon-optimized derivatives thereof, may be used in the present invention.

Similarly, a suitable Tsa1 protein will comprise:

a) a nucleotide sequence encoding a polypeptide capable of interacting with the Yap1 transcription factor to increase Yap1 transcription factor activity, wherein the polypeptide has at least 70% amino acid identity, based on the BLASTP method of alignment, when compared to a sequence selected from the group consisting of SEQ ID NO:34 [ScTsa1] or SEQ ID NO:36 [YlTsa1];

b) a nucleotide sequence encoding a polypeptide capable of interacting with the Yap1 transcription factor to increase Yap1 transcription factor activity, wherein the nucleotide sequence has at least 70% sequence identity, based on the BLASTN method of alignment, when compared to a sequence selected from the group consisting of SEQ ID NO:33 [ScTsa1] or SEQ ID NO:35 [YlTsa1]; or, c) a complement of the nucleotide sequence of (a) or (b), wherein the complement and the nucleotide sequence consist of the same number of nucleotides and are 100% complementary.

A suitable Tsa1 protein will comprise at least one redox-active cysteine residue, such as Cys48 and Cys171 of ScTsa1 (SEQ ID NO:34).

Preferably, the polypeptide sequence encoding Tsa1 is set forth in SEQ ID NO:36 ("YlTsa1"). In alternate embodiments, the polypeptide sequence encoding Tsa1 has at least 70% sequence identity based on the CLUSTALW method of alignment, when compared to SEQ ID NO:34 or SEQ ID NO:36, i.e., the polypeptide may have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity when compared thereto. In alternate embodiments, the sequences set forth in Table 12 (Example 9), or homologs or codon-optimized derivatives thereof, may be used in the present invention.

A suitable Ybp1 protein will comprise a nucleotide sequence encoding a polypeptide capable of interacting with the Yap1 transcription factor to increase Yap1 transcription factor activity, wherein the polypeptide sequence is classified within a kinetochor_Ybp2 super family, based on the conserved domain method of analysis.

Preferably, the polypeptide sequence encoding Ybp1 is set forth in SEQ ID NO:40 ("YlYbp1"). In alternate embodiments, the ScYbp1 (SEQ ID NO:38) or any of the sequences set forth in Table 13 or Table 14 (Example 10, i.e., including SEQ ID NOs:43-48), or homologs or codon-optimized derivatives thereof, may be used in the present invention.

For clarity, the increased Yap1 transcription factor activity in the transgenic oleaginous yeast of the present invention can be achieved by overexpression of a native Yap1 transcription factor, a foreign Yap1 transcription factor, a native protein that is capable of activating the transcription factor, a foreign protein that is capable of activating the transcription factor, or any combination thereof. Overexpression may occur, for example, by introducing additional copies of appropriate genes into the host cell on multicopy plasmids. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

As noted above, it may be desirable to codon-optimize any one of the Yap1, Gpx3, Tsa1 or Ybp1 proteins described above for expression in the oleaginous yeast of interest. For example, one could codon-optimize any of the sequences set forth in Tables 4, 9, 12, 13 or 14 for expression in *Y. lipolytica*. This is possible based on previous determination of the *Y. lipolytica* codon usage profile, identification of those codons that are preferred, and determination of the consensus sequence around the 'ATG' initiation codon (see U.S. Pat. No. 7,238,482).

In another embodiment, the sequences set forth in Tables 4, 9, 12, 13 or 14, or portions of thereof, may be used to search for Yap1, Gpx3, Tsa1 or Ybp1 homologs in the same or other species using sequence analysis software. In general, such computer software matches similar sequences by assigning degrees of homology to various substitutions, deletions, and other modifications. Use of software algorithms, such as the BLASTP method of alignment with a low complexity filter and the following parameters: Expect value=10, matrix=Blosum 62 (Altschul, et al., *Nucleic Acids Res.,* 25:3389-3402 (1997)), is well-known as a means for comparing any Yap1, Gpx3, Tsa1 or Ybp1 protein in Tables 4, 9, 12, 13 or 14 against a database of nucleic or protein sequences and thereby identifying similar known sequences within a preferred organism.

Use of a software algorithm to comb through databases of known sequences is particularly suitable for the isolation of homologs having a relatively low percent identity to publicly available Yap1, Gpx3, Tsa1 or Ybp1 sequences, such as those described in Tables 4, 9, 12, 13 or 14. It is predictable that isolation would be relatively easier for Yap1, Gpx3, Tsa1 or Ybp1 homologs of at least about 70%-75% identity and more preferably at least about 80%-85% identity to publicly available Yap1, Gpx3, Tsa1 or Ybp1 sequences. Further, those sequences that are at least about 85%-90% identical would be particularly suitable for isolation and those sequences that are at least about 90%-95% identical would be the most easily isolated.

Some Yap1, Gpx3, Tsa1 or Ybp1 homologs have also been isolated by the use of motifs unique to these enzymes. As one will appreciate, this is particularly useful with transcription factors, which share relatively low sequence homology with one another, despite sharing several conserved sequence motifs. Motifs (e.g., the basic DNA binding region and adjacent leucine-rich zipper region of the bZIP leucine zipper motif, N-terminal Cys-rich domain and C-terminal Cys-rich domain of a Yap1 transcription factor) are identified by their high degree of conservation in aligned sequences of a family of protein homologues. As unique "signatures", they can determine if a protein with a newly determined sequence belongs to a previously identified protein family. Similarly, Gpx3 and Tsa1 homologs are expected to comprise at least one redox-active cysteine residue, whose relative position within the protein sequence will be conserved. These motifs are useful as diagnostic tools for the rapid identification of novel homologous genes.

Any of the Yap1, Gpx3, Tsa1 or Ybp1 nucleic acid fragments described herein or in public literature, or any identified homologs, may be used to isolate genes encoding homologous proteins from the same or other species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies, such as polymerase chain reaction ["PCR"] (U.S. Pat. No. 4,683,202); ligase chain reaction ["LCR"] (Tabor, S. et al., *Proc. Natl. Acad. Sci. U.S.A.,* 82:1074 (1985)); or strand displacement amplification ["SDA"] (Walker, et al., *Proc. Natl. Acad. Sci. U.S.A.,* 89:392 (1992)); and, 3) methods of library construction and screening by complementation.

The present invention is also drawn to methods of increasing oil content in an oleaginous yeast, wherein said method comprises:

a) engineering the oleaginous yeast to overexpress a protein selected from the group consisting of:
   (i) a Yap1 transcription factor;
   (ii) a protein that is capable of activating the transcription factor;
   (iii) a combination of (a) and (b); and,
b) growing the oleaginous yeast under suitable conditions to result in increased oil content when compared to the oil content of a non-transgenic oleaginous yeast.

One of ordinary skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Maniatis, Silhavy, and Ausubel, as cited above.

In general, the choice of sequences included in a recombinant expression construct depends on the desired expression products, the nature of the host cell and the proposed means of separating transformed cells versus non-transformed cells. Typically, a vector contains at least one expression cassette, a selectable marker and sequences allowing autonomous replication or chromosomal integration. Suitable expression cassettes typically comprise a promoter, the coding sequence of a selected gene (e.g., encoding a polypeptide whose expression results in increased Yap1 transcription factor activity), and a terminator (i.e., a chimeric gene). Preferably, both control regions are derived from genes from the transformed host cell.

Virtually any promoter (i.e., native, synthetic, or chimeric) capable of directing expression of an ORF encoding a polypeptide of the invention herein will be suitable, although transcriptional and translational regions from *Y. lipolytica* are particularly useful. Expression can be accomplished in an induced or constitutive fashion. Induced expression can be accomplished by inducing the activity of a regulatable promoter operably linked to the gene of interest (e.g., Yap1, Gpx3, Tsa1, Ybp1), while constitutive expression can be achieved by the use of a constitutive promoter operably linked to the gene of interest.

A terminator can be derived from the 3' region of a gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is highly preferred.

Although not intended to be limiting, preferred promoters and terminators for use in a recombinant *Y. lipolytica* are those taught in U.S. Pat. Pub. No. 2009-0093543-A1, U.S. Pat. Pub. No. 2010-0068789-A1, U.S. Pat. Pub. No. 2011-0059496-A1, U.S. Provisional Pat. Appl. No. 61/469,933 (filed Mar. 31, 2011), U.S. Provisional Pat. Appl. No. 61/470,539 (filed Apr. 1, 2011), U.S. Provisional Pat. Appl. No.

61/471,736 (filed Apr. 5, 2011), and U.S. Provisional Pat. Appl. No. 61/472,742 (filed Apr. 7, 2011), the disclosure of each which is hereby incorporated herein by reference. More specifically, preferred promoters include: GPD, GPDIN, GPM, GPM/FBAIN, FBA, FBAIN, FBAINm, GPAT, YAT1, EXP1, DGAT2, EL1, ALK2, and SPS19.

Many specialized expression vectors have been created to obtain a high expression rate. Such vectors are made by adjusting certain properties that govern transcription, RNA stability, translation, protein stability and location, and secretion from the host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell.

Once a DNA cassette (e.g., comprising a chimeric gene comprising a promoter, an ORF encoding a polypeptide whose expression results in increased Yap1 transcription factor activity [e.g., Yap1, Gpx3, Tsa1, Ybp1], and a terminator) suitable for expression in an oleaginous yeast has been obtained, it is placed in a plasmid vector capable of autonomous replication in the host cell, or DNA fragment containing the chimeric gene is directly integrated into the genome. Integration of expression cassettes can occur randomly within the host genome or can be targeted through the use of constructs containing regions of homology with the genome sufficient to target recombination to a particular locus. Where constructs are targeted to an endogenous locus, all or some of the transcriptional and translational regulatory regions can be provided by the endogenous locus.

Constructs comprising a chimeric gene(s) of interest may be introduced into oleaginous yeast by any standard technique. These techniques include transformation (e.g., lithium acetate transformation [*Methods in Enzymology,* 194:186-187 (1991)]), bolistic impact, electroporation, microinjection, or any other method that introduces the gene(s) of interest into the host cell. More specific teachings applicable for *Y. lipolytica* include U.S. Pat. No. 4,880,741 and U.S. Pat. No. 5,071,764 and Chen, D. C. et al. (*Appl. Microbiol. Biotechnol.,* 48(2):232-235 (1997)). Preferably, integration of a linear DNA fragment into the genome of the host is favored in transformation of *Y. lipolytica* host cells. Integration into multiple locations within the genome can be particularly useful when high level expression of genes are desired. Preferred loci include those taught in U.S. Pat. Pub. No. 2009-0093543-A1.

The terms "transformed", "transformant" or "recombinant" are used interchangeably herein. A transformed host will have at least one copy of an expression construct and may have two or more, depending upon whether the expression cassette is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. No. 7,238,482, U.S. Pat. No. 7,259,255 and WO 2006/052870.

Stability of an integrated DNA fragment in oleaginous yeast is dependent on the individual transformants, the recipient strain and the targeting platform used. Thus, multiple transformants of a particular recombinant microbial host should be screened in order to obtain a strain displaying the desired expression level and pattern. Southern analysis of DNA blots (Southern, *J. Mol. Biol.,* 98:503 (1975)), Northern analysis of mRNA expression (Kroczek, *J. Chromatogr. Biomed. Appl.,* 618 (1-2):133-145 (1993)), Western analysis of protein expression, phenotypic analysis or GC analysis are suitable screening methods.

Suitable host cells for use in the invention herein are oleaginous yeast, capable of accumulating oil in excess of about 25% of their DCW, as defined above. In some embodiments herein, the oleaginous yeast host is a wildtype strain; in alternate embodiments, the oleaginous yeast host is a transformed or recombinant strain that was previously subjected to transformation with an expression construct that does not affect the native level of Yap1 transcription factor activity. For example, in some embodiments, the oleaginous yeast has been previously modified such that it is capable of producing at least one non-native product of interest, wherein examples of suitable non-native products of interest include, e.g., polyunsaturated fatty acids, carotenoids, amino acids, vitamins, sterols, flavonoids, organic acids, polyols and hydroxyesters, quinone-derived compounds and resveratrol, although this is not intended to be limiting herein.

It is noted that an oleaginous yeast host may produce "polyunsaturated fatty acids" (or "PUFAs") within its microbial oils (either through natural abilities or genetic modifications). Although the health benefits associated with PUFAs, especially omega-3 and omega-6 PUFAs, have been well documented, these molecules are particularly susceptible to lipid peroxidation within the cell since they contain multiple double bonds in between which lie methylene-$CH_2$-groups that possess especially reactive hydrogens. More specifically, PUFAs refer herein to fatty acids having at least 18 carbon atoms and 2 or more double bounds. The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["n-6"] versus "omega-3 fatty acids" ["n-3"] are provided in U.S. Pat. No. 7,238,482, which is hereby incorporated herein by reference. U.S. Pat. App. Pub. No. 2009-0093543-A1, Table 3, provides a detailed summary of the chemical and common names of omega-3 and omega-6 PUFAs and their precursors, and well as commonly used abbreviations.

Some examples of PUFAs, however, include, but are not limited to, linoleic acid ["LA", 18:2 omega-6], gamma-linolenic acid ["GLA", 18:3 omega-6], eicosadienoic acid ["EDA", 20:2 omega-6], dihomo-gamma-linolenic acid ["GLA", 20:3 omega-6], arachidonic acid ["ARA", 20:4 omega-6], docosatetraenoic acid ["DTA", 22:4 omega-6], docosapentaenoic acid ["DPAn-6", 22:5 omega-6], alpha-linolenic acid ["ALA", 18:3 omega-3], stearidonic acid ["STA", 18:4 omega-3], eicosatrienoic acid ["ETA", 20:3 omega-3], eicosatetraenoic acid ["ETrA", 20:4 omega-3], eicosapentaenoic acid ["EPA", 20:5 omega-3], docosapentaenoic acid ["DPAn-3", 22:5 omega-3] and docosahexaenoic acid ["DHA", 22:6 omega-3].

Much effort has been invested towards engineering strains of *Y. lipolytica* for PUFA production. For example, U.S. Pat. No. 7,238,482 demonstrated the feasibility of producing omega-6 and omega-3 fatty acids in the yeast. U.S. Pat. No. 7,932,077 demonstrated recombinant production of 28.1% EPA of total fatty acids; U.S. Pat. No. 7,588,931 demonstrated recombinant production of 14% ARA of total fatty acids; U.S. Pat. No. 7,550,286 demonstrated recombinant production of 5% DHA of total fatty acids; and, U.S. Pat. Appl. Pub. No. 2009-0093543-A1 describes optimized recombinant strains for EPA production and demonstrated production of up to 55.6% EPA of total fatty acids. U.S. Pat. Appl. Pub. No. 2010-0317072-A1 describes further optimized recombinant *Y. lipolytica* strains producing microbial oils comprising up to 50% EPA of TFAs and having a ratio of at least 3.1 of EPA, measured as a weight percent of TFAs, to linoleic acid, measured as a weight percent of TFAs. The transformant *Y. lipolytica* express various combinations of desaturase (i.e., delta-12 desaturase, delta-6 desaturase, delta-8 desaturase, delta-5 desaturase, delta-17 desaturase, delta-15 desaturase, delta-9 desaturase, delta-4 desaturase) and elongase (i.e., $C_{14/16}$ elongase, $C_{16/18}$ elongase, $C_{18/20}$ elongase, $C_{20/22}$ elongase and delta-9 elongase) genes for PUFA production.

Table 3 provides information about some of the specific *Y. lipolytica* strains described in the above cited references, wherein said strains possess various combinations of desaturases and elongases. It is to be recognized that these are exemplary strain which could be used as suitable host cells in the invention herein, although the specific strain and the specific strains and the specific PUFAs produced (or quantities thereof) are by no means limiting to the invention herein.

TABLE 3

Lipid Profile of Representative *Y. lipolytica* Strains Engineered to Produce Omega-3/Omega-6 PUFAs

| Strain | Reference | ATCC Deposit No. | Fatty Acid Content (As A Percent [%] of Total Fatty Acids) 16:0 | 16:1 | 18:0 | 18:1 | 18:2 | 18:3 (ALA) | GLA | 20:2 (EDA) |
|---|---|---|---|---|---|---|---|---|---|---|
| pDMW208 | U.S. Pat. No. | | 11.9 | 8.6 | 1.5 | 24.4 | 17.8 | 0 | 25.9 | — |
| pDMW208D62 | 7,465,564 | — | 16.2 | 1.5 | 0.1 | 17.8 | 22.2 | 0 | 34 | — |
| M4 | U.S. Pat. No. 7,932,077 | — | 15 | 4 | 2 | 5 | 27 | 0 | 35 | — |
| Y2034 | U.S. Pat. No. | — | 13.1 | 8.1 | 1.7 | 7.4 | 14.8 | 0 | 25.2 | — |
| Y2047 | 7,588,931 | PTA-7186 | 15.9 | 6.6 | 0.7 | 8.9 | 16.6 | 0 | 29.7 | — |
| Y2214 | | — | 7.9 | 15.3 | 0 | 13.7 | 37.5 | 0 | 0 | — |
| EU | U.S. Pat. No. | — | 19 | 10.3 | 2.3 | 15.8 | 12 | 0 | 18.7 | — |
| Y2072 | 7,932,077 | — | 7.6 | 4.1 | 2.2 | 16.8 | 13.9 | 0 | 27.8 | — |
| Y2102 | | — | 9 | 3 | 3.5 | 5.6 | 18.6 | 0 | 29.6 | — |
| Y2095 | | — | 13 | 0 | 2.6 | 5.1 | 16 | 0 | 29.1 | — |
| Y2090 | | — | 6 | 1 | 6.1 | 7.7 | 12.6 | 0 | 26.4 | — |
| Y2096 | | PTA-7184 | 8.1 | 1 | 6.3 | 8.5 | 11.5 | 0 | 25 | — |
| Y2201 | | PTA-7185 | 11 | 16.1 | 0.7 | 18.4 | 27 | 0 | — | 3.3 |
| Y3000 | U.S. Pat. No. 7,550,286 | PTA-7187 | 5.9 | 1.2 | 5.5 | 7.7 | 11.7 | 0 | 30.1 | — |
| Y4001 | U.S. Pat. | — | 4.3 | 4.4 | 3.9 | 35.9 | 23 | 0 | — | 23.8 |
| Y4036 | Appl. Pub. | — | 7.7 | 3.6 | 1.1 | 14.2 | 32.6 | 0 | — | 15.6 |
| Y4070 | No. 2009- | — | 8 | 5.3 | 3.5 | 14.6 | 42.1 | 0 | — | 6.7 |
| Y4086 | 0093543-A1 | — | 3.3 | 2.2 | 4.6 | 26.3 | 27.9 | 6.9 | — | 7.6 |
| Y4128 | | PTA-8614 | 6.6 | 4 | 2 | 8.8 | 19 | 2.1 | — | 4.1 |
| Y4158 | | — | 3.2 | 1.2 | 2.7 | 14.5 | 30.4 | 5.3 | — | 6.2 |
| Y4184 | | — | 3.1 | 1.5 | 1.8 | 8.7 | 31.5 | 4.9 | — | 5.6 |
| Y4259 | | — | 4.4 | 1.4 | 1.5 | 3.9 | 19.7 | 2.1 | — | 3.5 |
| Y4305 | | — | 2.8 | 0.7 | 1.3 | 4.9 | 17.6 | 2.3 | — | 3.4 |
| Y4127 | Int'l. App. Pub. No. WO | PTA-8802 | 4.1 | 2.3 | 2.9 | 15.4 | 30.7 | 8.8 | — | 4.5 |
| Y4184 | 2008/073367 | — | 2.2 | 1.1 | 2.6 | 11.6 | 29.8 | 6.6 | — | 6.4 |
| Y8404 | U.S. Pat. | — | 2.8 | 0.8 | 1.8 | 5.1 | 20.4 | 2.1 | | 2.9 |
| Y8406 | Appl. Pub. No. 2010- | PTA-10025 | 2.6 | 0.5 | 2.9 | 5.7 | 20.3 | 2.8 | | 2.8 |
| Y8412 | 0317072-A1 | PTA-10026 | 2.5 | 0.4 | 2.6 | 4.3 | 19.0 | 2.4 | | 2.2 |
| Y8647 | | — | 1.3 | 0.2 | 2.1 | 4.7 | 20.3 | 1.7 | | 3.3 |
| Y9028 | | — | 1.3 | 0.2 | 2.1 | 4.4 | 19.8 | 1.7 | | 3.2 |
| Y9477 | | — | 2.6 | 0.5 | 3.4 | 4.8 | 10.0 | 0.5 | | 2.5 |
| Y9497 | | — | 2.4 | 0.5 | 3.2 | 4.6 | 11.3 | 0.8 | | 3.1 |
| Y9502 | | — | 2.5 | 0.5 | 2.9 | 5.0 | 12.7 | 0.9 | | 3.5 |
| Y9508 | | — | 2.3 | 0.5 | 2.7 | 4.4 | 13.1 | 0.9 | | 2.9 |
| Y8145 | | — | 4.3 | 1.7 | 1.4 | 4.8 | 18.6 | 2.8 | | 2.2 |
| Y8259 | | PTA- | 3.5 | 1.3 | 1.3 | 4.8 | 16.9 | 2.3 | | 1.9 |

TABLE 3-continued

Lipid Profile of Representative *Y. lipolytica* Strains Engineered to Produce Omega-3/Omega-6 PUFAs

| | | | | | | | | | |
|---|---|---|---|---|---|---|---|---|---|
| | 10027 | | | | | | | | |
| Y8370 | — | 3.4 | 1.1 | 1.4 | 4.0 | 15.7 | 1.9 | | 1.7 |
| Y8672 | — | 2.3 | 0.4 | 2.0 | 4.0 | 16.1 | 1.4 | | 1.8 |

| Strain | Reference | ATCC Deposit No. | Fatty Acid Content (As A Percent [%] of Total Fatty Acids) DGLA | ARA | ETA | EPA | DPA | DHA | TFAs % DCW |
|---|---|---|---|---|---|---|---|---|---|
| pDMW208 | U.S. Pat. No. | | — | — | — | — | — | — | — |
| pDMW208D62 | 7,465,564 | — | — | — | — | — | — | — | — |
| M4 | U.S. Pat. No. 7,932,077 | — | 8 | 0 | 0 | 0 | — | — | — |
| Y2034 | U.S. Pat. No. | — | 8.3 | 11.2 | — | — | — | — | — |
| Y2047 | 7,588,931 | PTA-7186 | 0 | 10.9 | — | — | — | — | — |
| Y2214 | | — | 7.9 | 14 | — | — | — | — | — |
| EU | U.S. Pat. No. | — | 5.7 | 0.2 | 3 | 10.3 | — | — | 36 |
| Y2072 | 7,932,077 | — | 3.7 | 1.7 | 2.2 | 15 | — | — | — |
| Y2102 | | — | 3.8 | 2.8 | 2.3 | 18.4 | — | — | — |
| Y2095 | | — | 3.1 | 1.9 | 2.7 | 19.3 | — | — | — |
| Y2090 | | — | 6.7 | 2.4 | 3.6 | 26.6 | — | — | 22.9 |
| Y2096 | | PTA-7184 | 5.8 | 2.1 | 2.5 | 28.1 | — | — | 20.8 |
| Y2201 | | PTA-7185 | 3.3 | 1 | 3.8 | 9 | — | — | — |
| Y3000 | U.S. Pat. No. 7,550,286 | PTA-7187 | 2.6 | 1.2 | 1.2 | 4.7 | 18.3 | 5.6 | — |
| Y4001 | U.S. Pat. | — | 0 | 0 | 0 | — | — | — | — |
| Y4036 | Appl. Pub. | — | 18.2 | 0 | 0 | — | — | — | — |
| Y4070 | No. 2009- | — | 2.4 | 11.9 | — | — | — | — | — |
| Y4086 | 0093543-A1 | — | 1 | 0 | 2 | 9.8 | — | — | 28.6 |
| Y4128 | | PTA-8614 | 3.2 | 0 | 5.7 | 42.1 | — | — | 18.3 |
| Y4158 | | — | 3.1 | 0.3 | 3.4 | 20.5 | — | — | 27.3 |
| Y4184 | | — | 2.9 | 0.6 | 2.4 | 28.9 | — | — | 23.9 |
| Y4259 | | — | 1.9 | 0.6 | 1.8 | 46.1 | — | — | 23.7 |
| Y4305 | | — | 2 | 0.6 | 1.7 | 53.2 | — | — | 27.5 |
| Y4127 | Int'l. App. Pub. No. WO | PTA-8802 | 3.0 | 3.0 | 2.8 | 18.1 | — | — | — |
| Y4184 | 2008/073367 | — | 2.0 | 0.4 | 1.9 | 28.5 | — | — | 24.8 |
| Y8404 | U.S. Pat. | — | 2.5 | 0.6 | 2.4 | 51.1 | — | — | 27.3 |
| Y8406 | Appl. Pub. No. 2010- | PTA-10025 | 2.1 | 0.5 | 2.1 | 51.2 | — | — | 30.7 |
| Y8412 | 0317072-A1 | PTA-10026 | 2.0 | 0.5 | 1.9 | 55.8 | — | — | 27.0 |
| Y8647 | | — | 3.6 | 0.7 | 3.0 | 53.6 | — | — | 37.6 |
| Y9028 | | — | 2.5 | 0.8 | 1.9 | 54.5 | — | — | 39.6 |
| Y9477 | | — | 3.7 | 1.0 | 2.1 | 61.4 | — | — | 32.6 |
| Y9497 | | — | 3.6 | 0.9 | 2.3 | 58.7 | — | — | 33.7 |
| Y9502 | | — | 3.3 | 0.8 | 2.4 | 57.0 | — | — | 37.1 |
| Y9508 | | — | 3.3 | 0.9 | 2.3 | 58.7 | — | — | 34.9 |
| Y8145 | | — | 1.5 | 0.6 | 1.5 | 48.5 | — | — | 23.1 |
| Y8259 | | PTA-10027 | 1.7 | 0.6 | 1.6 | 53.9 | — | — | 20.5 |
| Y8370 | | — | 1.9 | 0.6 | 1.5 | 56.4 | — | — | 23.3 |
| Y8672 | | — | 1.6 | 0.7 | 1.1 | 61.8 | — | — | 26.5 |

Notes:

The terms "lipid profile" and "lipid composition" are interchangeable and refer to the amount of individual fatty acids contained in a particular lipid fraction, such as in the total lipid or the oil, wherein the amount is expressed as a wt % of TFAs. The sum of each individual fatty acid present in the mixture should be 100.

The term "total fatty acids" ("TFAs") refer to the sum of all cellular fatty acids that can be derivitized to fatty acid methyl esters ("FAMEs") by the base transesterification method (as known in the art) in a given sample, which may be the biomass or oil, for example. Thus, total fatty acids include fatty acids from neutral lipid fractions (including diacylglycerols, monoacylglycerols and triacylglycerols) and from polar lipid fractions but not free fatty acids. The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

Fatty acids are 16:0 (palmitate), 16:1 (palmitoleic acid), 18:0 (stearic acid), 18:1 (oleic acid), 18:2 (linoleic acid), 18:3 (ALA or alpha-linolenic acid), GLA (gamma-linolenic acid), 20:2 (EDA or eicosadienoic acid), DGLA (dihomo-gamma-linolenic acid), ARA (arachidonic acid), ETA (eicosatetraenoic acid), EPA (eicosapentaenoic acid), DPA (docosapentaenoic acid) and DHA (docosahexaenoic acid).

It will be obvious to one of ordinary skill in the art that means to reduce reactive oxygen species ["ROS"] in oleaginous yeast producing at least one PUFA will be particularly desirable. Thus, one embodiment of the present invention concerns a transgenic oleaginous yeast having increased oil content and producing at least one PUFA, wherein said transgenic oleaginous yeast comprises increased Yap1 transcription factor activity and wherein the increased oil content is compared to the oil content of a non-transgenic oleaginous yeast. Increased Yap1 transcription factor activity, via overexpression of the Yap1 transcription factor itself or by overexpression of a protein that is capable of activating the Yap1 transcription factor (e.g., Gpx3, Tsa1 Ybp1), may additionally result in increased content of a given PUFA(s) in a cell as its weight percent of the dry cell weight ["% DCW"].

For example, a measure of EPA productivity or EPA titer ["EPA % DCW"] is determined according to the following formula: (EPA % TFAs)*(TFAs % DCW)]/100. In any of the strains set forth above in Table 3, producing primarily EPA, it is expected that genetic manipulation that results in increased Yap1 transcription factor activity in the yeast will result in both increased oil content ["TFAs % DCW"] and increased EPA titer ["EPA % DCW"].

In preferred embodiments, a transgenic oleaginous yeast of the present invention that produces at least one PUFA will be capable of producing at least 10-25% greater content of a given PUFA(s) as its weight percent of the DCW than the content of the given PUFA(s) as its weight percent of the DCW in a non-transgenic oleaginous yeast (i.e., whose Yap1 transcription factor activity has not been increased). More preferably, the increase in the given PUFA(s) is at least 25-45%, and most preferably the increase in the given PUFA (s) is at least 45-65% greater. Thus, those skilled in the art will appreciate that the increase in the given PUFA(s) as its weight percent of the DCW can be any integer percentage (or fraction thereof) from 10% up to and including 100% or greater, i.e., specifically, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

A transformed host cell can be grown under conditions that optimize expression of chimeric genes (e.g., encoding a polypeptide whose expression results in increased Yap1 transcription factor activity [e.g., Yap1, Gpx3, Tsa1, Ybp1], etc.) and produce the greatest and the most economical yield of the microbial oils. In general, media conditions that may be optimized include: the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Oleaginous yeast are grown in a complex medium (e.g., yeast extract-peptone-dextrose broth (YPD)) or a defined minimal medium that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are taught in U.S. Pat. No. 7,238,482 and U.S. Pat. Pub. No. 2011-0059204-A1. Although it is contemplated that the source of carbon utilized in the present invention may encompass a wide variety of carbon-containing sources, preferred carbon sources are sugars, glycerol and/or fatty acids. Most preferred is glucose, sucrose, invert sucrose, fructose and/or fatty acids containing between 10-22 carbons.

Nitrogen may be supplied from an inorganic (e.g., $(NH_4)_2SO_4$) or organic (e.g., urea, glutamate, or yeast extract) source. In addition to sucrose and nitrogen sources, the fermentation medium also contains suitable minerals, salts, cofactors, buffers, vitamins and other components known to those skilled in the art suitable for the growth of the microorganism and promotion of the enzymatic pathways necessary for microbial oil production. Particular attention is given to several metal ions (e.g., $Fe^{+2}$, $Cu^{+2}$, $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage fermentation process, since the metabolic state must be "balanced" between growth and synthesis/storage of fats. Thus, most preferably, a two-stage fermentation process is employed for the production of PUFAs in oleaginous yeast. This process is described in U.S. Pat. No. 7,238,482, as are various suitable fermentation process designs (i.e., batch, fed-batch and continuous) and considerations during growth).

Example 10 of U.S. Pat. Appl. Pub. No. 2009-0093543-A1 also provides a detailed description of parameters required for a 2-L fermentation of the recombinant *Yarrowia lipolytica* strain Y4305 (whose maximum production was 12.1 EPA % DCW [i.e., 55.6 EPA % TFAs, with a ratio of EPA % TFAs to LA % TFAs of 3.03], over a period of 162 hours). This disclosure includes a description of means to prepare inocula from frozen cultures to generate a seed culture, initially culture the yeast under conditions that promoted rapid growth to a high cell density, and then culture the yeast to promote lipid and PUFA accumulation (via starving for nitrogen and continuously feeding glucose). Process variables including temperature (controlled between 30-32° C.), pH (controlled between 5-7), dissolved oxygen concentration and glucose concentration were monitored and controlled per standard operating conditions to ensure consistent process performance and final PUFA oil quality. In particular, the data of Example 10 of U.S. Pat. Appl. Pub. No. 2009-0093543-A1 are useful to demonstrate that the oil profile of the recombinant microbial host cell will depend on the fermentation run itself, media conditions, process parameters, scale-up, etc., as well as the particular time-point in which the culture is sampled. Thus, the particular engineered strain therein was capable of producing microbial oil having a variety of different lipid contents and compositions (i.e., based on EPA % TFAs, LA % TFAs and EPA:LA ratio).

These factors should be considered when culturing the transgenic oleaginous yeast described herein, to realize the full potential of the yeast in any particular fermentation run.

Transgenic oleaginous yeast and non-transgenic oleaginous yeast should be grown and sampled under similar conditions when oil content is to be compared.

In some aspects herein, the primary product is oleaginous yeast biomass. As such, isolation and purification of the microbial oils from the biomass may not be necessary (i.e., wherein the whole cell biomass is the product).

However, certain end uses and/or product forms may require partial and/or complete isolation/purification of the microbial oil from the biomass, to result in partially purified biomass, purified oil, and/or purified lipid fractions thereof. For example, PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also provided by A. Singh and O. Ward (*Adv. Appl. Microbiol.,* 45:271-312 (1997)).

In general, methods for the recovery and purification of microbial lipids and/or PUFAs from microbial biomass may include extraction (e.g., U.S. Pat. Nos. 6,797,303 and 5,648,564) with organic solvents, sonication, supercritical fluid extraction (e.g., using carbon dioxide), saponification and physical means such as presses, bead beaters, or combinations thereof. One is referred to the teachings of U.S. Pat. No. 7,238,482 for additional details.

There are a plethora of food and feed products incorporating omega-3 and/or omega-6 fatty acids, particularly e.g., ALA, GLA, ARA, EPA, DPA and DHA. It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils containing omega-3 and/or omega-6 fatty acids will be suitable for use in a variety of food and feed products including, but not limited to: food analogs, meat products, cereal products, baked foods, snack foods and dairy products (see U.S. Pat. Appl. Pub. No. 2006-0094092). Feed products also include those for animal uses.

The present compositions may be used in formulations to impart health benefit in medical foods including medical nutritionals, dietary supplements, infant formula and pharmaceuticals. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

The present compositions may be used in formulations to impart animal health benefit in medical foods including medical nutritionals, dietary supplements, and pharmaceuticals.

EXAMPLES

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes

The structure of an expression cassette is represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*

*Y. lipolytica* strain ATCC #20362 was purchased from the American Type Culture Collection (Rockville, Md.). *Y. lipolytica* strains were routinely grown at 28-30° C. in several media, according to the recipes shown below.

Synthetic Complete Media ["SC"] Media (per liter): 6.7 g Yeast Nitrogen base with ammonium sulfate and without amino acids; 20 g glucose; 1.9 g/L Yeast synthetic drop-out medium supplement without uracil High Glucose Media ["HGM"] (per liter): 80 glucose, 2.58 g $KH_2PO_4$ and 5.36 g $K_2HPO_4$, pH 7.5 (do not need to adjust).

Synthetic Dextrose Media ["SD"] (per liter): 6.7 g Yeast Nitrogen base with ammonium sulfate and without amino acids; 20 g glucose.

Fermentation Medium ["FM"] (per liter): 6.7 g/L YNB without amino acids; 6 g/L $KH_2PO_4$; 2 g/L $K_2HPO_4$; 1.5 g/L $MgSO_4$-heptahydrate; 5 g/L yeast extract; 2% carbon source (wherein the carbon source is either glucose or sucrose).

Transformation of *Y. lipolytica* was performed as described in U.S. Pat. Appl. Pub. No. 2009-0093543-A1, hereby incorporated herein by reference.

Fatty Acid Analysis of *Yarrowia lipolytica*

For fatty acid ["FA"] analysis, cells were collected by centrifugation and lipids were extracted as described in Bligh, E. G. & Dyer, W. J. (*Can. J. Biochem. Physiol.,* 37:911-917 (1959)). Fatty acid methyl esters ["FAMEs"] were prepared by transesterification of the lipid extract with sodium methoxide (Roughan, G., and Nishida I., *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 µl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 µl hexane, the sample was vortexed and spun. The upper layer was removed and analyzed by GC.

Alternately, a modification of the base-catalysed transesterification method described in *Lipid Analysis*, William W. Christie, 2003 was used for routine analysis of the broth samples from either fermentation or flask samples. Specifically, broth samples were rapidly thawed in room temperature water, then weighed (to 0.1 mg) into a tarred 2 mL microcentrifuge tube with a 0.22 µm Corning® Costar® Spin-X® centrifuge tube filter (Cat. No. 8161). Sample (75-800 µl) was used, depending on the previously determined DCW. Using an Eppendorf 5430 centrifuge, samples are centrifuged for 5-7 min at 14,000 rpm or as long as necessary to remove the broth. The filter was removed, liquid was drained, and ~500 µl of deionized water was added to the filter to wash the sample. After centrifugation to remove the water, the filter was again removed, the liquid drained and the filter re-inserted. The tube was then re-inserted into the centrifuge, this time with the top open, for ~3-5 min to dry. The filter was then cut approximately ½ way up the tube and inserted into a fresh 2 mL round bottom Eppendorf tube (Cat. No. 22 36 335-2).

The filter was pressed to the bottom of the tube with an appropriate tool that only touches the rim of the cut filter container and not the sample or filter material. A known amount of C15:0 TAG (above) in toluene was added and 500 μl of freshly made 1% sodium methoxide in methanol solution. The sample pellet was firmly broken up with the appropriate tool and the tubes were closed and placed in a 50° C. heat block (VWR Cat. No. 12621-088) for 30 min. The tubes were then allowed to cool for at least 5 min. Then, 400 μl of hexane and 500 μl of a 1 M NaCl in water solution were added, the tubes were vortexed for 2×6 sec and centrifuged for 1 min. Approximately 150 μl of the top (organic) layer was placed into a GC vial with an insert and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (μg) of any fatty acid FAME ["μg FAME"] is calculated according to the formula: (area of the FAME peak for the specified fatty acid/area of the standard FAME peak)*(μg of the standard C15:0 TAG), while the amount (μg) of any fatty acid ["μg FA"] is calculated according to the formula: (area of the FAME peak for the specified fatty acid/area of the standard FAME peak)*(μg of the standard C15:0 TAG)*0.9503, since 1 μg of C15:0 TAG is equal to 0.9503 μg fatty acids. Note that the 0.9503 conversion factor is an approximation of the value determined for most fatty acids, which range between 0.95 and 0.96.

The lipid profile, summarizing the amount of each individual fatty acid as a wt % of TFAs, was determined by dividing the individual FAME peak area by the sum of all FAME peak areas and multiplying by 100.

Analysis of Total Lipid Content and Composition in *Yarrowia lipolytica* by Flask Assay Flask assays were conducted as follows to analyze the total lipid content and composition in a particular strain of *Y. lipolytica*. Specifically, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaking incubator at 250 rpm and at 30° C., 6 mL of the culture was harvested by centrifugation and resuspended in 25 mL HGM in a 125 mL flask. After 5 days in a shaking incubator at 250 rpm and at 30° C., a 1 mL aliquot was used for fatty acid analysis (above) and 10 mL dried for dry cell weight ["DCW"] determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

Total lipid content of cells ["TFAs % DCW"] is calculated and considered in conjunction with data tabulating the concentration of each fatty acid as a weight percent of TFAs ["% TFAs"] and the EPA content as a percent of the dry cell weight ["EPA % DCW"].

Example 1

Identification of a *Yarrowia lipolytica* Gene Having Homology to the *Saccharomyces cerevisiae* YAP1

An ortholog to the *S. cerevisiae* Yap1 (GenBank Accession No. NM_001182362; SEQ ID NO:1) ["ScYap1"] was identified in *Yarrowia lipolytica* by conducting BLAST searches using ScYap1 as the query sequence against the public *Y. lipolytica* protein database of the "Yeast project *Genolevures*" (Center for Bioinformatics, LaBRI, Talence Cedex, France) (see also Dujon, B. et al., *Nature,* 430(6995):35-44 (2004)).

The protein sequence having the best homology (with an expectation value of 1.8e-18) to ScYap1 among all *Y. lipolytica* proteins, YALI0F03388p (GenBank Accession No. XP_504945; SEQ ID NO:4), was given the designation "YlYap". YALI0F03388p was annotated therein as "weakly similar to uniprot|Q9P5L6 *Neurospora crassa* NCU03905.1 related to AP-1-like transcription factor".

An alignment of ScYap1 and the putative YlYap1 is shown in FIG. 2A-B. Both proteins have a basic leucine zipper (bZIP) motif, corresponding to a N-terminal basic region enriched in basic amino acids that is adjacent to a leucine zipper that is characterized by several leucine residues regularly spaced at seven-amino acid intervals. With respect to the figure, arginine and lysine amino acid residues in bold font and underlined correspond to the basic region; a star highlights each of the leucine residues within the leucine zipper. Vertical boxes highlight cysteine residues within the N-terminal Cys-rich domain of ScYap1 (i.e., corresponding to Cys303, Cys310 and Cys315 of SEQ ID NO:2) and the C-terminal Cys-rich domain (i.e., corresponding to Cys598, Cys620 and Cys629 of SEQ ID NO:2). Five of these residues are conserved in YlYap1. As discussed in Toone and Jones (*Curr. Opin. Genet. Dev.,* 9: 55-61 (1999)), the bZIP domain and the cysteine rich domains are characteristics of AP-1 family proteins.

Using the protein sequence encoding YALI0F03388p (SEQ ID NO:4), National Center for Biotechnology Information ["NCBI"] BLASTP 2.2.26+ (Basic Local Alignment Search Tool; Altschul, S. F., et al., *Nucleic Acids Res.,* 25:3389-3402 (1997); Altschul, S. F., et al., *FEBS J.,* 272: 5101-5109 (2005)) searches were conducted to identify sequences having similarity within the BLAST "nr" database (comprising all non-redundant GenBank CDS translations, RefSeq protein sequences from NCBI's Reference Sequence Project, the Brookhaven Protein Data Bank ["PDB"] protein sequence database, the SWISS-PROT protein sequence database, the Protein Information Resource ["PIR"] protein sequence database and the Protein Research Foundation ["PRF"] protein sequence database).

The results of the BLASTP comparison summarizing the sequence to which SEQ ID NO:4 has the most similarity may be reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

A large number of proteins were identified as sharing similarity to YALI0F03388p (SEQ ID NO:4). Table 4 provides a partial summary of those hits having an Expectation value greater or equal to "2e-13" and annotation that specifically identified the protein (i.e., while hits to hypothetical proteins are excluded), although this should not be considered as limiting to the disclosure herein. The proteins in Table 4 shared between 13-87% query coverage with SEQ ID NO:4.

TABLE 4

| Genes Sharing Similarity To YlYap1 (SEQ ID NO: 4) | | | |
|---|---|---|---|
| Accession | Description | Query coverage | E value |
| XP_002847259.1 | Chap1 [*Arthroderma otae* CBS 113480] | 86% | 2e−39 |
| EGS19655.1 | putative Ap-1-like transcription factor [*Chaetomium thermophilum* var. *thermophilum* DSM 1495] | 87% | 1e−37 |
| AAS64313.1 | Chap1 [*Cochliobolus heterostrophus*] | 28% | 2e−27 |
| XP_002145733.1 | bZIP transcription factor AP-1/Yap1, putative [*Penicillium marneffei* ATCC 18224] | 39% | 4e−27 |
| EGR47222.1 | transcription factor [*Trichoderma reesei* QM6a] | 30% | 5e−27 |
| EFQ30244.1 | transcription factor PAP1 [*Glomerella graminicola* M1.001] | 50% | 6e−27 |
| XP_001394766.2 | bZIP transcription factor (AP-1) [*Aspergillus niger* CBS 513.88] | 26% | 1e−26 |
| XP_001258114.1 | bZIP transcription factor (AP-1), putative [*Neosartorya fischeri* NRRL 181] | 38% | 1e−26 |
| EEH47458.1 | bZIP transcription factor (AP-1) [*Paracoccidioides brasiliensis* Pb18] | 38% | 1e−26 |
| XP_002477983.1 | bZIP transcription factor AP-1/Yap1, putative [*Talaromyces stipitatus* ATCC 10500] | 41% | 2e−26 |
| EGE77501.1 | BZIP transcription factor AP-1/Yap1 [*Ajellomyces dermatitidis* ATCC 18188] | 41% | 3e−26 |
| XP_002627437.1 | bZIP transcription factor AP-1/Yap1 [*Ajellomyces dermatitidis*] | 41% | 3e−26 |
| EFY90531.1 | AP-1-like protein [*Metarhizium acridum* CQMa 102] | 29% | 8e−26 |
| EFW21644.1 | bZIP transcription factor [*Coccidioides posadasii* str. Silveira] | 37% | 1e−25 |
| XP_003065816.1 | bZIP family transcription factor [*Coccidioides posadasii* C735 delta SOWgp] | 37% | 2e−25 |
| CAX15423.1 | Ap1-like transcription factor [*Botryotinia fuckeliana*] | 22% | 2e−25 |
| XP_680782.1 | TPA: bZIP transcription factor AP-1/Yap1, putative (AFU_orthologue; AFUA_6G09930) [*Aspergillus nidulans* FGSC A4] | 27% | 2e−25 |
| XP_001268032.1 | bZIP transcription factor (AP-1), putative [*Aspergillus clavatus* NRRL 1] | 26% | 3e−25 |
| EER41522.1 | bZIP transcription factor [*Ajellomyces capsulatus* H143] | 40% | 4e−25 |
| EGC49388.1 | bZIP transcription factor [*Ajellomyces capsulatus* H88] | 40% | 4e−25 |
| XP_002145732.1 | bZIP transcription factor AP-1/Yap1, putative [*Penicillium marneffei* ATCC 18224] | 41% | 7e−25 |
| EGX87755.1 | bZIP transcription factor (AP-1), putative [*Cordyceps militaris* CM01] | 22% | 1e−24 |
| CBX91516.1 | similar to AP1-like transcription factor [*Leptosphaeria maculans* JN3] | 28% | 2e−24 |
| EFX02671.1 | AP-1-like, bzip transcription factor [*Grosmannia clavigera* kw1407] | 43% | 3e−24 |
| XP_003017058.1 | bZIP transcription factor AP-1/Yap1, putative [*Arthroderma benhamiae* CBS 112371] | 36% | 4e−24 |
| XP_003021545.1 | bZIP transcription factor AP-1/Yap1, putative [*Trichophyton verrucosum* HKI 0517] | 27% | 6e−24 |
| EGE03693.1 | bZIP transcription factor AP-1/Yap1 [*Trichophyton equinum* CBS 127.97] | 27% | 6e−24 |
| XP_001931984.1 | Chap1 [*Pyrenophora tritici-repentis* Pt-1C-BFP] | 15% | 8e−24 |

TABLE 4-continued

| Genes Sharing Similarity To YlYap1 (SEQ ID NO: 4) | | | |
|---|---|---|---|
| Accession | Description | Query coverage | E value |
| ACM50933.1 | AP-1-like protein [*Alternaria alternata*] | 57% | 1e−23 |
| EGO54582.1 | PAP1-domain-containing protein [*Neurospora tetrasperma* FGSC 2509] | 28% | 1e−23 |
| EGY17906.1 | Chap1 [*Verticillium dahliae* VdLs.17] | 24% | 6e−23 |
| EGP91344.1 | bZIP transcription factor [*Mycosphaerella graminicola* IPO323] | 40% | 1e−22 |
| EFZ02600.1 | AP-1-like protein [*Metarhizium anisopliae* ARSEF 23] | 38% | 5e−22 |
| ACN43306.1 | AP1-like transcription factor [*Alternaria alternata*] | 26% | 6e−22 |
| BAE48266.1 | AP-1-like transcription factor [*Pichia jadinii*] | 50% | 6e−20 |
| XP_001387049.2 | transcriptional activator involved in oxidative stress response [*Scheffersomyces stipitis* CBS 6054]; basic-leucine zipper transcription factor | 16% | 1e−17 |
| XP_002494040.1 | Basic leucine zipper (bZIP) transcription factor required for oxidative stress tolerance [*Komagataella pastoris*] | 13% | 3e−17 |
| CBX94954.1 | similar to bZIP transcription factor [*Leptosphaeria maculans* JN3] | 25% | 4e−16 |
| XP_451077.1 | AP-1-like transcription factor KlYAP1 [Kluyveromyces lactis] | 31% | 7e−16 |
| EGV63639.1 | PAP1-domain-containing protein [*Candida tenuis* ATCC 10573] | 13% | 1e−15 |
| EFW96135.1 | AP-1-like transcription factor [*Ogataea parapolymorpha* DL-1] | 22% | 2e−15 |
| BAA87082.1 | AP-1-like transcription factor [*Schizosaccharomyces pombe*] | 17% | 6e−14 |
| CAA40363.1 | AP-1-like transcription factor [*Schizosaccharomyces pombe*] | 72% | 8e−14 |
| EEU08396.1 | Yap1p [*Saccharomyces cerevisiae* JAY291] | 26% | 1e−13 |
| NP_593662.1 | transcription factor Pap1/Caf3 [*Schizosaccharomyces pombe* 972h-] | 74% | 1e−13 |
| GAA25439.1 | K7_Yap1p [*Saccharomyces cerevisiae* Kyokai no. 7] | 23% | 2e−13 |
| EDN64386.1 | jun-like transcription factor [*Saccharomyces cerevisiae* YJM789] | 23% | 2e−13 |
| CAA43195.1 | par1 [*Saccharomyces cerevisiae*] | 23% | 2e−13 |
| NP_013707.1 | Yap1p [*Saccharomyces cerevisiae* S288c] | 23% | 2e−13 |
| CAY81817.1 | Yap1p [*Saccharomyces cerevisiae* EC1118] | 23% | 2e−13 |
| CAA41536.1 | transcriptional activator protein [*Saccharomyces cerevisiae*] | 23% | 2e−13 |

Based on the BLASTP searches, YALI0F03388p (SEQ ID NO:4) shared the best similarity with hypothetical protein BC1G__14094 from *Botryotinia fuckeliana* (GenBank Accession No. XP__001547321), with 30% identity and 47% similarity, and an expectation value of 1e-41.

Among proteins with known function, the best hits were to: Chap1 from *Arthroderma otae* CBS 113480 (GenBank Accession No. XP__002847259.1), having 30% identity and 46% similarity, and an expectation value of 2e-39; the putative Ap-1-like transcription factor from *Chaetomium thermophilum* var. *thermophilum* DSM 1495, having 31% identity and 46% similarity, and an expectation value of 1 e-37; and, Chap1 from *Cochliobolus heterostrophus* (GenBank Accession No. AAS64313), having 48% identity and 64% similarity, and an expectation value of 2e-27. Chap1 is known as a functional homolog of *S. cerevisiae* Yap1 (S. Lev et al., *Eukaryotic Cell,* 4(2):443-454 (2005)).

Based on the above analyses, SEQ ID NO:3 was hypothesized to encode the Yap1 transcription factor of *Y. lipolytica* ("YIYap1"), wherein the protein sequence is set forth as SEQ ID NO:4.

It is not surprising that YIYap1 shares such relatively low percent identity and similarity with other bZIP transcription factors. For example, the *Candida glabrata* CgAP1p (Gen Bank Accession No. XP 446996) has been positively characterized as a functional ortholog of Yap1 (Chen, K.-H. et al., *Gene,* 386(1-2):63-72 (2007)). Despite shared functionality, Chen et al. reports that the *Candida glabrata* CgAP1p showed only 37% amino acid identity with *S. cerevisiae* Yap1p (GenBank Accession No. NP 013707), 30% identity with *Kluyveromyces lactis* KIAP1p (GenBank Accession No. P56095), 26% identity with *Candida albicans* CAP1p (GenBank Accession No. AAD00802), and 19% identity with *Schizosaccharomyces pombe* Pap1p (GenBank Accession No. CAB66170); notably, however, the identity between *Candida glabrata* CgAP1p and *S. cerevisiae* Yap1p was especially high in the bZip domain (73% identity), the N-terminal cysteine-rich domain (75% identity) and the C-terminal cysteine-rich domain (85% identity).

Thus, despite the sequence analyses described above, further functional analyses were necessary to confirm that YIYap1 functioned in a manner homologous to that of ScYap1.

Example 2

Increased Hydrogen Peroxide Sensitivity in *Yarrowia lipolytica* YAP1 Knockout Strain Y4184U (yaD1Δ)

The present Example describes the use of construct pYRH60 (FIG. 3A; SEQ ID NO:5) to down-regulate expression of chromosomal YAP1 gene from an EPA producing engineered strain of *Yarrowia lipolytica*, Y4184U (Example 7, infra). Transformation of *Y. lipolytica* strain Y4184U with the YAP1 knockout construct fragment resulted in strain Y4184U (yap1Δ). The effect of the Yap1 knockout on oxidative stress sensitivity and on accumulated lipid level and EPA production was determined and compared. Specifically, knockout of YAP1 resulted in hyper-sensitivity against $H_2O_2$, as compared to cells whose native Yap1 had not been knocked out.

Generation Of Strain Y4184U (yap1Δ)

Plasmid pYRH60 was derived from plasmid pYPS161, which was described in U.S. Patent App. No. 2010-0062502 (Example 2, FIG. 5A, SEQ ID NO:40 therein) and contained the following components:

TABLE 5

Description of Plasmid pYPS161 (SEQ ID NO: 6)

| RE Sites And Nucleotides Within SEQ ID NO: 6 | Description Of Fragment And Chimeric Gene Components |
|---|---|
| AscI/BsiWI (1521-157) | 1364 bp PEX10 knockout fragment #1 of *Yarrowia* PEX10 gene (GenBank Accession No. AB036770) |
| PacI/SphI (5519-4229) | 1290 bp PEX10 knockout fragment #2 of *Yarrowia* PEX10 gene (GenBank Accession No. AB036770) |
| SalI/EcoRI (7170-5551) | *Yarrowia* URA3 gene (GenBank Accession No. AJ306421) |
| 2451-1571 | ColE1 plasmid origin of replication |
| 3369-2509 | ampicillin-resistance gene ($Amp^R$) for selection in *E. coli* |
| 3977-3577 | *E. coli* f1 origin of replication |

A 940 by 5' promoter region (SEQ ID NO:7) of the *Y. lipolytica* YAP1 gene ("YIYAP1"; SEQ ID NO:3) replaced the AscI/BsiWI fragment of pYPS161 (SEQ ID NO:6) and a 1164 by 3' terminator region (SEQ ID NO:32) of the YIYAP1 gene replaced the PacI/SphI fragment of pYPS161 to produce pYRH60 (SEQ ID NO:5; FIG. 3A).

*Y. lipolytica* strain Y4184U was transformed with the purified 4.7 kB AscI/SphI fragment of YAP1 knockout construct pYRH60 (SEQ ID NO:5) (General Methods).

To screen for cells having the yap1 deletion, quantitative real time PCR on YIYap1 was conducted, with the *Yarrowia* translation elongation factor gene TEF1 (GenBank Accession No. AF054510) used as the control. Real time PCR primers and a TaqMan® probe targeting the YAP1 gene and the control TEF1 gene, respectively, were designed with Primer Express software version 2.0 (Applied Biosystems, Foster City, Calif.). Specifically, real time PCR primers YI-EF-1214F (SEQ ID NO:8), YI-EF-1270R (SEQ ID NO:9), YAP1-346F (SEQ ID NO:10) and YAP1-409R (SEQ ID NO:11) were designed, as well as YAP1-366T (i.e., 5' 6-FAM™-CGGGCTGCCCAAAGGGCC-TAMRA™, wherein the nucleotide sequence is set forth as SEQ ID NO:13). The TaqMan probe YL-EF-MGB-1235T (i.e., 5' 6-FAM™-CCTTCACTGAGTACCC-TAMRA™, wherein the nucleotide sequence is set forth as SEQ ID NO:12) was obtained from Applied Biosystems. The 5' end of the TaqMan fluorogenic probes have the 6-FAM™ fluorescent reporter dye bound, while the 3' end comprises the TAMRA™ quencher. PCR primers and the YAP1 probe were obtained from Sigma-Genosys (Woodlands, Tex.).

Knockout candidate DNA was prepared by suspending 1 colony in 50 μl of water. Reactions for TEF1 and YAP1 were run in the same Real Time PCR well, in triplicate, for each sample. Real time PCR reactions included 10 pmoles each of forward and reverse primers (i.e., YI-EF-1214F, YI-EF-1270R, YAP1-346F and YAP1-409R, supra), and 2.5 pmoles TaqMan® probe (i.e., YL-EF-MGB-1235T and YAP1-366T, supra), 10 μl TaqMan® Universal PCR Master Mix—No AmpErase® Uracil-N-Glycosylase (UNG) (Catalog No. PN 4326614, Applied Biosystems), 1 μl colony suspension and 8.5 μl RNase/DNase free water for a total volume of 20 μl per reaction. Reactions were run on the ABI PRISM® 7900 Sequence Detection System under the following conditions: initial denaturation at 95° C. for 10 min, followed by 40 cycles of denaturation at 95° C. for 15 sec and annealing at 60° C. for 1 min.

Real time data was collected automatically during each cycle by monitoring 6-FAM™ fluorescence. Data analysis was performed using TEF1 gene threshold cycle ($C_T$) values for data normalization as per ABI PRISM® 7900 Sequence Detection System instruction manual (see ABI User Bulletin #2 "Relative Quantitation of Gene Expression"). Knockout clones were identified as having no detectable signal for the YAP1 gene and a $C_T$ value for TEF1≤30.

The methodology set forth above identified one of the colonies screened as a yap1 knockout. The *Y. lipolytica* yap1Δ mutant of Y4184U was designated RHY240.

$H_2O_2$ Sensitivity Assays with Knockout Strain Y4184U (Yap1Δ)

In *S. cerevisiae*, strains lacking Yap1 are hypersensitive to killing by $H_2O_2$. This phenotype is related to Yap1's role in controlling the induction of oxidative stress defense genes, such as TRR1 (cytoplasmic thioredoxin reductase), TRX2 (thioredoxin), GLR1 (glutathione reductase), and GSH1 (γ-glutamylcystein synthetase). To test the function of the putative YIYap1 as an oxidative stress regulator, Y4184U (yap1Δ) was subjected to a $H_2O_2$ sensitivity assay.

Y4184U (yap1Δ) and Y4184 (control) cells were grown to an exponential phase ($OD_{600}$ of ~0.5) in SC medium and diluted to an $OD_{600}$ of 0.01 with fresh SC medium. Aliquots (100 μl) of the diluted cultures were incubated with fresh $H_2O_2$ at final concentrations from 0 to 50 mM at 30° C. for 1 hr, and 7 μl from each sample was spotted onto YPD plates. Cells were further grown at 30° C. for 2 days on the YPD plate.

Y4184U (yap1Δ) cells showed much higher sensitivity to $H_2O_2$ stress than the control strain Y4184 (FIG. 4A). This result supports the hypothesis that YIYap1, corresponding to YALI0F03388p, was important for oxidative stress defense in *Y. lipolytica* and was a functional homolog of ScYap1.

Example 3

Overexpression of *Yarrowia lipolytica* YAP1 in *Saccharomyces cerevisiae* YAP1 Knockout Strain BY4743 (yap1Δ)

The present Example describes the use of centromeric plasmid pYRH61 (FIG. 3B; SEQ ID NO:14) to overexpress the putative YIYap1 (SEQ ID NO:4) in a *S. cerevisiae* yap1Δ strain, to evaluate the effect on oxidative stress sensitivity. Specifically, overexpression of YIYAP1 resulted in functional complementation of hyper-sensitivity against $H_2O_2$ in the *S. cerevisiae* yap1Δ strain.

Construction of *S. Cerevisiae* Overexpression Plasmid pYRH61

Plasmid pYRH61 was derived from plasmid pRS316 (Sikorski and Hieter, *Genetics,* 122:19-27 (1989)), a centromeric plasmid with URA3 as a selective marker. The pYRH61 contained the following components:

TABLE 6

Description of Plasmid pYRH61 (SEQ ID NO: 14)

| RE Sites And Nucleotides Within SEQ ID NO: 14 | Description Of Fragment And Chimeric Gene Components |
|---|---|
| SalI/SpeI (7442-8042) | 601 bp FBA1 promoter region of *S. cerevisiae* (GenBank Accession No. X15003) |
| NotI/SacI (1613-2634) | 1022 bp FBA1 terminator region of *S. cerevisiae* (GenBank Accession No. X15003) |
| SpeI/NotI (1-1612) | YIYAP1 (YALI0F03388g; SEQ ID NO: 3) (GenBank Accession No. XP504945) |
| SalI/SacI (2635-7436) | pRS316 vector backbone |

Specifically, a 1.6 kB fragment of the YIYAP1 gene was amplified by PCR from the *Y. lipolytica* genome using primers YI.Yap1-F-SpeI (SEQ ID NO:15) and Yap1-R (SEQ ID NO:16). The reaction mixture contained 1 μl of the genomic DNA, 1 μl each of the primers (from 20 μM stocks), 2 μl water, and 45 μl AccuPrime Pfx SuperMix from Invitrogen. Amplification was carried out as follows: initial denaturation at 95° C. for 5 min, followed by 35 cycles of denaturation at 95° C. for 60 sec, annealing at 55° C. for 60 sec, and elongation at 68° C. for 180 sec. A final elongation cycle at 72° C. for 7 min was carried out, followed by reaction termination at 4° C. A 1.6 kb DNA fragment was obtained from the PCR reaction.

The amplified gene was digested with SpeI/NotI and cloned with a 601 by 5' promoter region (SEQ ID NO:17) of the *S. cerevisiae* FBA1 gene ["ScFBA1"] and a 1022 bp 3' terminator region of ScFBA1 (SEQ ID NO:18) into pRS316 (SEQ ID NO:19) to produce pYRH61 (SEQ ID NO:14; FIG. 3B). Thus, pYRH61 contained a chimeric ScFBA1:: YIYAP1::ScFBA1 gene.

$H_2O_2$ Sensitivity Assays with *S. cerevisiae* Strains Expressing pYRH61

*S. cerevisiae* strains BY4743 (MATa/α his3Δ1/his3Δ1 leu2Δ0/leu2Δ0 LYS2/lys2Δ0 met15Δ0/MET15 ura3Δ0/ura3Δ0) and its isogenic yap1Δ strain BY4743 (yap1Δ) (obtained from Invitrogen, Carlsbad, Calif.) were transformed with pRS316 (vector control) or pYRH61 to evaluate the effect of YIYap1 overexpression on oxidative stress sensitivity.

Cells were grown to an exponential phase ($OD_{600}$ of ~0.5) in SC medium lacking uracil and diluted to an $OD_{600}$ of 0.01 with fresh SC medium. Aliquots (100 μl) of the diluted cultures were incubated with fresh $H_2O_2$ at the final concentrations from 0 to 50 mM at 30° C. for 1 hr, and 7 μl from each sample was spotted onto YPD plates. Spotted cells were further grown at 30° C. for 2 days on the YPD plate.

FIG. 4B shows the results of the $H_2O_2$ sensitivity assay. Specifically, the top two rows are BY4743 transformants (i.e., with either the control vector or pYRH61, respectively), while the bottom two rows are BY4743 (yap1Δ) transformants (i.e., with either the control vector or pYRH61, respectively).

As shown in FIG. 4B, the BY4743 yap1Δ strain transformed with control plasmid pRS316 showed higher sensitivity to $H_2O_2$ stress than its isogenic BY4743 wild type strain with either the control or pYRH61. When YIYap1 was overexpressed in the BY4743 yap1Δ strain, cells become much more resistant to the oxidative stress than BY4743 yap1Δ transformants with the control plasmid, suggesting the YIYap1 (SEQ ID NO:4) conferred the resistance against oxidative stress.

The results herein support the hypothesis that YIYap1, corresponding to YALI0F03388p, was a functional homolog of ScYap1 and was associated with oxidative stress defense.

Example 4

Overexpression of *Yarrowia lipolytica* YAP1 in *Y. Lipolytica* Strains Y4184 and Y9502

The present Example describes synthesis of overexpression construct pYRH43 (FIG. 5A; SEQ ID NO:20) and its transformation into *Y. lipolytica* strains Y4184U (Example 7) and Y9502U (Example 8). The effect of YIYAP1 overexpression on accumulated lipid level was determined and compared. Specifically, YIYAP1 overexpression resulted in increased total lipid (measured as total fatty acids as a percent of the total dry cell weight ["TFAs % DCW"]) as compared to cells whose native Yap1 level had not been manipulated.

Construction of *Y. lipolytica* Overexpression Plasmid pYRH43

Plasmid pYRH43 was derived from plasmid pZuFmEaD5s (described in Example 6 of U.S. Pat. No. 7,943,365, hereby incorporated herein by reference). Plasmid pZuFmEaD5s contained a chimeric FBAINm::EaD5S::PEX20 gene, wherein: (i) FBAINm is a *Y. lipolytica* promoter upstream of the fba1 gene encoding a fructose-bisphosphate aldolase enzyme (E.C. 4.1.2.13) (U.S. Pat. No. 7,202,356); (ii) EaD5S is a synthetic delta-5 desaturase derived from *Euglena anabaena* and codon-optimized for expression in *Yarrowia*, flanked by NcoI/NotI restriction enzyme sites; and, (iii) PEX20 is a PEX20 terminator sequence from the *Yarrowia* PEX20 gene (GenBank Accession No. AF054613).

A 1.6 kB fragment of the YIYAP1 gene was amplified by PCR from the *Y. lipolytica* genome using primers Yap1-F (SEQ ID NO:21) and Yap1-R (SEQ ID NO:16). The reaction mixture contained 1 μl of the genomic DNA, 1 μl each of the primers (from 20 μM stocks), 2 μl water, and 45 μl AccuPrime Pfx Supermix from Invitrogen. Amplification was carried out as follows: initial denaturation at 95° C. for 5 min, followed by 35 cycles of denaturation at 95° C. for 1 sec, annealing at 55° C. for 1 sec, and elongation at 68° C. for 3 sec. A final elongation cycle at 72° C. for 7 min was carried out, followed by reaction termination at 4° C. A 1.6 kb DNA fragment was obtained from the PCR reaction.

The amplified gene was digested with PciI/NotI and used to replace the NcoI/NotI fragment of pZuFmEaD5s to produce pYRH43. Thus, pYRH43 contained a chimeric FBAINm::YlYAP1::PEX20 gene.

Identification of Transformant Strains Y4184U+YAP1 and Y9502U+Yap1 by Quantitative Real Time PCR Plasmid pYRH43 was cut with BsiWI/PacI and a 4.4 kB fragment was isolated and used for transformation (General Methods) into *Y. lipolytica* strains Y4184U (Example 7) and Y9502U (Example 8), thereby producing strains Y4184U+YAP1 and Y9502U+Yap1.

Overexpression of YlYAP1 was confirmed by performing quantitative real time RT-PCR, using the *Yarrowia* TEF1 gene as the control in a manner similar to that described in Example 2.

Primers were qualified for real time quantitation using a dilution series of genomic DNA and the PCR conditions detailed below. Linear regression analysis was performed using the obtained $C_T$ values versus log ng DNA for each primer and probe set and the efficiencies were confirmed to be within 90-110%.

cDNA from strains Y4184U+YAP1 and Y9502U+Yap1 was prepared by first isolating RNA using a Qiagen RNeasy™ kit (Valencia, Calif.). Residual genomic DNA was then eliminated by treating 2 μg of RNA with DNase (Catalog No. PN79254, Qiagen) for 15 min at room temperature, followed by inactivation for 5 min at 75° C. The cDNA was generated from 1 μg of treated RNA using the High Capacity cDNA Reverse Transcription Kit from Applied Biosystems (Catalog No. PN 4368813), according to the manufacturer's recommended protocol.

Real time PCR reactions for YlTEF1 and YlYAP1 were run separately in triplicate for each sample. Real time PCR reactions included 0.2 μl each of forward and reverse primers (100 μM) (i.e., ef-324F [SEQ ID NO:22], ef-392R [SEQ ID NO:23], YAP1-346F [SEQ ID NO:10] and YAP1-409R [SEQ ID NO:11]), 0.05 μl of each TaqMan® probe (100 μM) (i.e., ef-345T [i.e., 5' 6-FAM™-TGCTGGTGGTGTTGGTGAGTT-TAMRA™, wherein the nucleotide sequence is set forth as SEQ ID NO:24] and YAP1-366T [i.e., 5' 6-FAM™-CGGGCTGCCCAAAGGGCC-TAMRA™, wherein the nucleotide sequence is set forth as SEQ ID NO:13]), 10 μl TaqMan® Universal PCR Master Mix™ No AmpErase® Uracil-N-Glycosylase (UNG) (Catalog No. PN 4326614, Applied Biosystems), 1 μl diluted cDNA (1:10), and 8.55 μl RNase/DNase free water for a total volume of 20 μl per reaction. Reactions were run on the ABI PRISM 7900 Sequence Detection System under the following conditions: initial denaturation at 95° C. for 10 min, followed by 40 cycles of denaturation at 95° C. for 15 sec and annealing at 60° C. for 1 min. A negative reverse transcription RNA control of each sample was run with the TEF1 primer set to confirm the absence of genomic DNA. Real time data was collected as described in Example 2.

Based on this analysis, it was concluded that the Y4184U+Yap1 strain showed approximately 2.9-fold higher expression level of the YlYAP1 gene, as compared to that of the Y4184U (Ura+) control strain, thereby confirming functionality of plasmid pYRH43.

Lipid Content and Composition in Transformant Strain Y4184U+YAP1

*Y. lipolytica* strain Y4184U (Ura+) (control) and strain Y4184U+Yap1 were grown under comparable oleaginous conditions. More specifically, oleaginous conditions were achieved by first growing the cultures aerobically in 25 mL of SD medium (starting $OD_{600}$ of ~0.3) at 30° C. for 48 h, and then harvesting the cells by centrifugation. The pellets were then resuspended in 25 mL of HGM and further incubated for 5 days in a shaker incubator at 250 rpm and 30° C.

The DCW, total lipid content of cells ["TFAs % DCW"], the concentration of each fatty acid as a weight percent of TFAs ["% TFAs"] and the EPA productivity (i.e., EPA content as its percent of the dry cell weight ["EPA % DCW"]) for *Y. lipolytica* Y4184U (Ura+) control and Y4184U+Yap1 strains are shown below in Table 7, while averages are highlighted in gray and indicated as "Ave". Abbreviations for fatty acids are as follows: stearic acid (18:0), oleic acid (18:1), linoleic acid (18:2), and eicosapentaenoic acid ("EPA", 20:5).

TABLE 7

Lipid Content And Composition In *Y. lipolytica* Strains Y4184U (Ura+) And Y4184U + Yap1

| Strains | DCW (g/L) | TFAs % DCW | % TFAs 18:0 | 18:1 | 18:2 | 20:5 EPA | EPA % DCW |
|---|---|---|---|---|---|---|---|
| Y4184U | 5.48 | 14.1 | 2.0 | 8.1 | 31.9 | 24.3 | 3.4 |
| (Ura+) | 4.38 | 15.5 | 1.7 | 7.8 | 32.5 | 27.8 | 4.3 |
| AVE | 4.93 | 14.8 | 1.9 | 8.0 | 32.2 | 26.1 | 3.9 |
| Y4184U + | 3.68 | 16.5 | 2.1 | 7.3 | 33.5 | 24.6 | 4.1 |
| YaP1 | 4.62 | 14.7 | 2.0 | 8.6 | 32.1 | 27.0 | 4.0 |
| | 3.94 | 16.2 | 1.9 | 9.3 | 35.4 | 22.1 | 3.6 |
| | 4.60 | 16.0 | 1.7 | 7.4 | 32.7 | 27.9 | 4.5 |
| | 4.00 | 17.1 | 1.9 | 8.1 | 31.7 | 27.5 | 4.7 |
| | 3.66 | 17.1 | 1.9 | 8.2 | 31.8 | 27.3 | 4.7 |
| | 4.42 | 17.7 | 2.3 | 8.9 | 29.6 | 28.9 | 5.1 |
| | 4.12 | 18.1 | 1.8 | 8.0 | 31.2 | 28.4 | 5.1 |
| | 4.26 | 16.1 | 2.1 | 8.7 | 30.8 | 28.1 | 4.5 |
| AVE | 4.14 | 16.6 | 2.0 | 8.3 | 30.8 | 26.9 | 4.5 |

Overexpression of YlYAP1 (SEQ ID NO:4), corresponding to locus YALI0F03388p, in Y4184U increased lipid content ["TFAs % DCW"] by approximately 12% and increased average EPA titer ["EPA % DCW"] approximately 15%, as compared to that of strain Y4184U (Ura+).

Lipid Content and Composition in Transformant Strain Y9502U+YAP1

*Y. lipolytica strain* Y9502 (control) and strain Y9502U+Yap1 (three isolates) were grown in duplicate under comparable oleaginous conditions, supra. Table 8 summarizes the DCW, TFAs % DCW, the concentration of each fatty acid as % TFAs, and EPA % DCW, in a format similar to that used in Table 7.

TABLE 8

Lipid Content And Composition In *Y. lipolytica* Strains Y9502 And Y9502U + Yap1

| Strains | DCW (g/L) | TFAs (%) DCW | % TFAs | | | | EPA % DCW |
|---|---|---|---|---|---|---|---|
| | | | 18:0 | 18:1 | 18:2 | 20:5 EPA | |
| Y9502 | 3.7 | 31.3 | 2.3 | 4.7 | 13.5 | 60.5 | 18.9 |
| | 3.6 | 30.7 | 2.3 | 4.7 | 13.5 | 60.5 | 18.5 |
| AVE | 3.6 | 31.0 | 2.3 | 4.7 | 13.5 | 60.5 | 18.7 |
| Y9502U + Yap1 | 4.2 | 37.0 | 2.2 | 5.3 | 14.3 | 59.8 | 22.1 |
| | 4.2 | 35.8 | 2.2 | 5.3 | 14.4 | 59.7 | 21.4 |
| | 4.1 | 35.5 | 2.2 | 5.3 | 14.4 | 59.6 | 21.1 |
| | 4.2 | 35.7 | 2.2 | 5.3 | 14.4 | 59.4 | 21.2 |
| | 4.2 | 36.1 | 2.2 | 5.2 | 14.3 | 59.8 | 21.6 |
| | 4.2 | 36.1 | 2.2 | 5.3 | 14.4 | 59.7 | 21.6 |
| AVE | 4.2 | 36.0 | 2.2 | 5.3 | 14.4 | 59.7 | 21.5 |

Overexpression of YlYAP1 (SEQ ID NO:4), corresponding to locus YALI0F03388p, in Y9502U increased lipid content ["TFAs % DCW"] by approximately 16% and increased average EPA titer ["EPA % DCW"] approximately 15%, as compared to that of Y9502.

Thus, it appears that overexpression of YlYAP1 in a PUFA-producing strain of *Yarrowia lipolytica* provided increased resistance to oxidative stresses. One beneficial outcome of this increased resistance to oxidative stresses is increased protection against lipid peroxidation, which thereby resulted in increased lipid and PUFA content.

Example 5

Identification of a *Yarrowia lipolytica* Gene Having Homology to the *Saccharomyces cerevisiae* GPX3

An ortholog to the *S. cerevisiae* Gpx3 (GenBank® Accession No. NM_001179559; SEQ ID NO:26) ["ScGpx3"] was identified in *Yarrowia lipolytica* by conducting BLAST searches using ScGpx3 as the query sequence against the public *Y. lipolytica* protein database of the "Yeast project *Genolevures*" (Center for Bioinformatics, LaBRI, Talence Cedex, France) (see also Dujon, B. et al., *Nature,* 430 (6995): 35-44 (2004)).

The protein sequence having the best homology (with an expectation value of 4e-68) to ScGpx3 among all *Y. lipolytica* proteins, YALI0E02310p (GenBank Accession No. XP_503454; SEQ ID NO:28), was given the designation "YlGpx3". YALI0E02310p was annotated therein as "highly similar to uniprot|P40581 *Saccharomyces cerevisiae* YIR037w HYR1 (ohnolog of YKL026C) Thiol peroxidase that functions as a hydroperoxide receptor to sense intracellular hydroperoxide levels and transduce a redox signal to the Yap1p transcription factor".

An alignment of ScGpx3 and the putative YlGpx3 is shown in FIG. 6. Vertical boxes highlight Cys36 and Cys82 of ScGpx3, important for inter- and intra-molecular interactions (Delaunay, A., et al., *Cell,* 111:471-481 (2002)). These residues are conserved in YlGpx3.

Using the protein sequence encoding YALI0E02310p (SEQ ID NO:28), NCBI BLASTP 2.2.26+ searches were conducted to identify sequences having similarity within the BLAST "nr" database, according to the methodology set forth in Example 1.

A large number of proteins were identified as sharing significant similarity to YALI0E02310p (SEQ ID NO:28). Table 9 provides a partial summary of those hits having an Expectation value greater or equal to "8e-72" and annotation that specifically identified the protein (i.e., while hits to hypothetical proteins and proteins from *Saccharomyces cerevisiae* are excluded), although this should not be considered as limiting to the disclosure herein. The proteins in Table 9 shared between 93-95% query coverage with SEQ ID NO:28.

TABLE 9

Genes Sharing Similarity To YlGpx3 (SEQ ID NO: 28)

| Accession | Description | Query coverage | E value |
|---|---|---|---|
| NP_985509.1 | AFL039Cp [*Ashbya gossypii* ATCC 10895] | 95% | 1e−85 |
| XP_002491803.1 | Thiol peroxidase that functions as a hydroperoxide receptor [*Komagataella pastoris* GS115] | 94% | 8e−85 |
| XP_002548683.1 | peroxiredoxin HYR1 [*Candida tropicalis* MYA-3404] | 94% | 2e−79 |
| XP_002548650.1 | peroxiredoxin HYR1 [*Candida tropicalis* MYA-3404] | 94% | 1e−77 |
| EGV62163.1 | glutathione peroxidase [*Candida tenuis* ATCC 10573] | 94% | 3e−76 |
| XP_714295.1 | potential glutathione peroxidase/redox transducer [*Candida albicans* SC5314 | 94% | 3e−76 |
| XP_002420878.1 | hydrogen peroxide resistance protein, putative; peroxiredoxin, putative; thiol peroxidase, putative [*Candida dubliniensis* CD36] | 94% | 8e−76 |
| NP_596146.1 | glutathione peroxidase Gpx1 [*Schizosaccharomyces pombe* 972h-] | 93% | 3e−75 |
| EFW96327.1 | Glutathione-Dependent Phospholipid Peroxidase Hyr1 [*Ogataea parapolymorpha* DL-1] | 95% | 2e−73 |
| XP_002172470.1 | glutathione peroxidase Gpx1 [*Schizosaccharomyces japonicus* yFS275] | 93% | 2e−73 |
| XP_001384693.1 | glutathione peroxidase [*Scheffersomyces stipitis* CBS 6054] | 94% | 7e−72 |
| XP_001698575.1 | glutathione peroxidase [*Chlamydomonas reinhardtii*] | 94% | 8e−72 |

Based on the BLASTP searches, YALI0E02310p (SEQ ID NO:28) shared the best similarity with a hypothetical protein from *Ashbya gossypii* (Gen Bank® Accession No. NP_985509), with 73% identity and 86% similarity, and an expectation value of 1e-85. Among proteins with known function, the best hit was the thiol peroxidase from *Pichia pastoris* (Gen Bank® Accession No. XP_002491803, renamed as *Komagataella pastoris*), with 71% identity and 89% similarity with an expectation value of 8e-85, followed by ScGPX3 with 72% identity and 86% similarity, and an expectation value of 7e-84.

Based on the above analyses, SEQ ID NO:27 was hypothesized to encode the Gpx3 thiol peroxidase of *Y. lipolytica* ("YlGpx3"), wherein the protein sequence is set forth as SEQ ID NO:28.

Example 6

Overexpression of *Yarrowia lipolytica* GPX3 in *Y. Lipolytica* Strain Y4184

The present Example describes synthesis of overexpression construct pYRH65 (FIG. 5B; SEQ ID NO:29) and its transformation into *Y. lipolytica* strain Y4184U (Example 7). The effect of YIGPX3 overexpression on accumulated lipid level was determined and compared. Specifically, YIGPX3 overexpression resulted in increased total lipid (measured as total fatty acids as a percent of the total dry cell weight ["TFAs % DCW"]) as compared to cells whose native Gpx3 level had not been manipulated.

Construction of *Y. lipolytica* Overexpression Plasmid pYRH65

A 510 by fragment encoding the YALI0E02310g was amplified from genomic DNA of *Yarrowia lipolytica* ATCC #20362 using primers GPX3-F (SEQ ID NO:30) and GPX3-R (SEQ ID NO:31). The reaction mixture contained 1 μl of the genomic DNA, 1 μl each of the primers (from 20 μM stocks), 2 μl water, and 45 μl AccuPrime Pfx SuperMix from Invitrogen. Amplification was carried out as follows: initial denaturation at 95° C. for 5 min, followed by 35 cycles of denaturation at 95° C. for 60 sec, annealing at 55° C. for 60 sec, and elongation at 68° C. for 60 sec. A final elongation cycle at 72° C. for 7 min was carried out, followed by reaction termination at 4° C. A 0.51 kb DNA fragment was obtained from the PCR reaction.

The amplified gene was then cut with NcoI/NotI and used to produce pYRH65 (FIG. 5B; SEQ ID NO:29), containing the following components:

TABLE 10

Description of Plasmid pYRH65

| RE Sites And Nucleotides Within SEQ ID NO: 29 | Description Of Fragment And Chimeric Gene Components |
|---|---|
| PmeI/BsiWI (6183--317) | FBAINm::YIGPX3::PEX20, comprising: FBAINm: *Yarrowia lipolytica* FBAINm promoter PmeI/NcoI (U.S. Pat. No. 7,202,356); YIGPX: *Yarrowia lipolytica* GPX3 (NcoI/NotI) PEX20: Pex20 terminator sequence from *Yarrowia* PEX20 gene NotI/BsiWI (GenBank Accession No. AF054613) |
| BsiWI/AscI (318-1211) | 894 bp 5' portion of *Yarrowia* Lip7 gene (labeled as "LipY-5'" in Figure; GenBank Accession No. AJ549519) |
| PacI/SphI (3920/4681) | 762 bp 3' portion of *Yarrowia* Lip7 gene (labeled as "LipY-3'" in Figure; GenBank Accession No. AJ549519) |
| PacI/PmeI (4682-6182) | *Yarrowia* URA3 gene (GenBank Accession No. AJ306421) |
| 2200-3060 | Ampicillin-resistance gene ($Amp^R$) for selection in *E. coli* |

Lipid Content and Composition in Transformant Strain Y4184U+Gpx3

Plasmid pYRH65 was cut with BsiWI/PacI and a 3.3 kB fragment was isolated and used for transformation of *Y. lipolytica* strain Y4184U, thereby producing strain Y4184U+Gpx3.

*Y. lipolytica* strain Y4184U (Ura+) (control) and strain Y4184U+Gpx3 were grown under comparable oleaginous conditions (as described in Example 4). Table 11 summarizes the DCW, TFAs % DCW, the concentration of each fatty acid as % TFAs, and EPA % DCW, in a format similar to that used in Table 7.

TABLE 11

Lipid Content And Composition In *Y. lipolytica* Strains Y4184U (Ura+) And Y4184U + Gpx3

| Strains | DCW (g/L) | TFAs % DCW | % TFAs 18:1 | 18:2 | 20:5 EPA | EPA (% DCW) |
|---|---|---|---|---|---|---|
| Y4184U (Ura+) | 6.40 | 11.2 | 10.1 | 28.2 | 24.8 | 2.8 |
| | 5.34 | 15.5 | 8.8 | 28.7 | 27.5 | 4.3 |
| | 6.20 | 13.3 | 9.8 | 28.3 | 25.5 | 3.4 |
| AVE | 5.98 | 13.3 | 9.6 | 28.4 | 25.9 | 3.5 |
| Y4184U + Gpx3 | 4.92 | 16.6 | 10.7 | 27.1 | 25.5 | 4.2 |
| | 4.28 | 20.0 | 11.2 | 26.2 | 25.7 | 5.1 |
| | 4.34 | 21.8 | 10.9 | 26.6 | 25.7 | 5.6 |
| AVE | 4.51 | 19.5 | 11.0 | 26.6 | 25.6 | 5.0 |

Overexpression of YIGPX3 (SEQ ID NO:27), corresponding to locus YALI0E02310g, in Y4184U increased lipid content ["TFAs % DCW"] by approximately 47% and increased average EPA titer ["EPA % DCW"] approximately 40%, as compared to that of strain Y4184U (Ura+).

Thus, it appears that overexpression of YIGpx3 in a PUFA-producing strain of *Yarrowia lipolytica* provided increased resistance to oxidative stresses. One beneficial outcome of this increased resistance to oxidative stresses was increased protection against lipid peroxidation, which thereby resulted in increased lipid and PUFA content.

Example 7

Generation of *Yarrowia lipolytica* Strains Y4184 and Y4184U for High EPA Production

*Y. lipolytica* strain Y4184U was used as a host in Examples 4 and 6. Strain Y4184U was derived from *Y. lipolytica* ATCC #20362 and is capable of producing high EPA relative to the total lipids via expression of a delta-9 elongase/delta-8 desaturase pathway. The strain has a Ura-phenotype and its construction is described in Example 7 of PCT Publication No. WO 2008/073367, hereby incorporated herein by reference.

The development of strain Y4184U required the construction of strains Y2224, Y4001, Y4001U, Y4036, Y4036U, Y4069, Y4084, Y4084U1, Y4127 (deposited with the American Type Culture Collection on Nov. 29, 2007, under accession number ATCC PTA-8802), Y4127U2, Y4158, Y4158U1 and Y4184.

The final genotype of strain Y4184 (producing 30.7% EPA of total lipids) with respect to wildtype *Yarrowia lipolytica* ATCC #20362 was unknown 1-, unknown 2-, unknown 4-, unknown 5-, unknown 6-, unknown 7-, YAT1::ME3S::Pex16, EXP1::ME3S::Pex20 (2 copies), GPAT::EgD9e::Lip2, FBAINm::EgD9eS::Lip2, EXP1::EgD9eS::Lip1, FBA::EgD9eS::Pex20, YAT1::EgD9eS::Lip2, GPD::EgD9eS::Lip2, GPDIN::EgD8M::Lip1, YAT1::EgD8M::Aco, EXP1::EgD8M::Pex16, FBAINm::EgD8M::Pex20, FBAIN::EgD8M::Lip1 (2 copies), GPM/FBAIN::FmD12S::Oct, EXP1::FmD12S::Aco, YAT1::FmD12::Oct, GPD::FmD12::Pex20, EXP1::EgD5S::Pex20, YAT1::EgD5S::Aco, YAT1::Rd5S::Oct, FBAIN::EgD5::Aco, FBAINm::PaD17::Aco, EXP1::PaD17::Pex16, YAT1::PaD17S::Lip1, YAT1::YICPT1::Aco, GPD::YICPT1::Aco.

Abbreviations above are as follows: ME3S is a codon-optimized $C_{16/18}$ elongase gene, derived from *Mortierella*

*alpina* [U.S. Pat. No. 7,470,532]; EgD9e is a *Euglena gracilis* delta-9 elongase gene [U.S. Pat. No. 7,645,604]; EgD9eS is a codon-optimized delta-9 elongase gene, derived from *Euglena gracilis* [U.S. Pat. No. 7,645,604]; EgD8M is a synthetic mutant delta-8 desaturase [U.S. Pat. No. 7,709, 239], derived from *Euglena gracilis* [U.S. Pat. No. 7,256, 033]; FmD12 is a *Fusarium moniliforme* delta-12 desaturase gene [U.S. Pat. No. 7,504,259]; FmD12S is a codon-optimized delta-12 desaturase gene, derived from *Fusarium moniliforme* [U.S. Pat. No. 7,504,259]; EgD5 is a *Euglena gracilis* delta-5 desaturase [U.S. Pat. No. 7,678,560]; EgD5S is a codon-optimized delta-5 desaturase gene, derived from *Euglena gracilis* [U.S. Pat. No. 7,678,560]; RD5S is a codon-optimized delta-5 desaturase, derived from *Peridinium* sp. CCMP626 [U.S. Pat. No. 7,695,950]; PaD17 is a *Pythium aphanidermatum* delta-17 desaturase [U.S. Pat. No. 7,556, 949]; PaD17S is a codon-optimized delta-17 desaturase, derived from *Pythium aphanidermatum* [U.S. Pat. No. 7,556, 949]; and, YlCPT1 is a *Yarrowia lipolytica* diacylglycerol cholinephosphotransferase gene [U.S. Pat. No. 7,932,077].

Finally, in order to disrupt the Ura3 gene in strain Y4184, construct pZKUE3S (PCT Publication No. WO 2008/ 073367, SEQ ID NO:78 therein) was used to integrate a EXP1::ME3S::Pex20 chimeric gene into the Ura3 gene of strain Y4184 to result in strains Y4184U1 (11.2% EPA of total lipids), Y4184U2 (10.6% EPA of total lipids) and Y4184U4 (15.5% EPA of total lipids), respectively (collectively, Y4184U).

It is noted that PCT Publication No. WO 2008/073367 describes a discrepancy in the EPA % TFAs quantified in Y4184 (30.7%) versus Y4184U (average 12.4%) due to differing growth conditions.

Example 8

Generation of *Yarrowia lipolytica* Strains Y9502 and Y9502U for High EPA Production

*Y. lipolytica* strain Y9502U was used as a host in Example 4. Strain Y9502U was derived from *Y. lipolytica* ATCC #20362 and is capable of producing high EPA relative to the total lipids via expression of a delta-9 elongase/delta-8 desaturase pathway. The strain has a Ura-phenotype.

Genotype of *Yarrowia lipolytica* Strain Y9502

The generation of strain Y9502 is described in U.S. Pat. Appl. Pub. No. 2010-0317072-A1. Strain Y9502, derived from *Y. lipolytica* ATCC #20362, was capable of producing about 57.0% EPA relative to the total lipids via expression of a delta-9 elongase/delta-8 desaturase pathway.

The final genotype of strain Y9502 with respect to wildtype *Yarrowia lipolytica* ATCC #20362 was Ura+, Pex3-, unknown 1-, unknown 2-, unknown 3-, unknown 4-, unknown 5-, unknown6-, unknown 7-, unknown 8-, unknown9-, unknown 10-, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, GPDIN::EgD5SM::Aco, GPM::EgD5SM::Oct, EXP1::EgD5SM::Lip1, YAT1::EaD5SM::Oct, FBAINm::PaD17::Aco, EXP1::PaD17::Pex16, YAT1::PaD17S::Lip1, YAT1::YlCPT1::Aco, YAT1::MCS::Lip1, FBA::MCS::Lip1, YAT1::MaLPAAT1S::Pex16.

Abbreviations used above and not set forth in Example 7 are as follows: EaD8S is a codon-optimized delta-8 desaturase gene, derived from *Euglena anabaena* [U.S. Pat. No. 7,790,156]; E389D9eS/EgD8M is a DGLA synthase created by linking a codon-optimized delta-9 elongase gene ("E389D9eS"), derived from *Eutreptiella* sp. CCMP389 (U.S. Pat. No. 7,645,604), to the delta-8 desaturase "EgD8M" (supra) [U.S. Pat. Appl. Pub. No. 2008-0254191-A1]; EgD9eS/EgD8M is a DGLA synthase created by linking the delta-9 elongase "EgD9eS" (supra) to the delta-8 desaturase "EgD8M" (supra) [U.S. Pat. Appl. Pub. No. 2008-0254191-A1]; EaD9eS/EgD8M is a DGLA synthase created by linking a codon-optimized delta-9 elongase gene ("EaD9eS"), derived from *Euglena anabaena* [U.S. Pat. No. 7,794,701], to the delta-8 desaturase "EgD8M" (supra) [U.S. Pat. Appl. Pub. No. 2008-0254191-A1]; EgD5M and EgD5SM are synthetic mutant delta-5 desaturase genes comprising a mutant HPGs (SEQ ID NO:41) motif [U.S. Pat. App. Pub. 2010-0075386-A1], derived from *Euglena gracilis* [U.S. Pat. No. 7,678,560]; EaD5SM is a synthetic mutant delta-5 desaturase gene comprising a mutant HaGG (SEQ ID NO:42) motif [U.S. Pat. App. Pub. 2010-0075386-A1], derived from *Euglena anabaena* [U.S. Pat. No. 7,943,365]; MCS is a codon-optimized malonyl-CoA synthetase gene, derived from *Rhizobium leguminosarum* bv. viciae 3841 [U.S. Pat. App. Pub. 2010-0159558-A1], and, MaLPAAT1S is a codon-optimized lysophosphatidic acid acyltransferase gene, derived from *Mortierella alpina* [U.S. Pat. No. 7,879,591].

For a detailed analysis of the total lipid content and composition in strain Y9502, a flask assay was conducted wherein cells were grown in 2 stages for a total of 7 days. Based on analyses, strain Y9502 produced 3.8 g/L DCW, 37.1 TFAs % DCW, 21.3 EPA % DCW, and the lipid profile was as follows, wherein the concentration of each fatty acid is as a weight percent of TFAs ["% TFAs"]: 16:0 (palmitate)—2.5, 16:1 (palmitoleic acid)—0.5, 18:0 (stearic acid)—2.9, 18:1 (oleic acid)—5.0, 18:2 (LA)—12.7, ALA-0.9, EDA-3.5, DGLA-3.3, ARA—0.8, ETrA—0.7, ETA-2.4, EPA-57.0, other-7.5.

Genotype of *Yarrowia lipolytica* Strain Y9502U

To disrupt the Ura3 gene in strain Y9502, SalI/PacI-digested construct pZKUM (see U.S. Pat. Appl. Pub. No. 2009-0093543-A1, Table 15, SEQ ID NO:133 and FIG. 8A therein) was used to integrate an Ura3 mutant gene into the Ura3 gene of strain Y9502, according to the General Methods. A total of 27 transformants (selected from a first group comprising 8 transformants, a second group comprising 8 transformants, and a third group comprising 11 transformants) were grown on Minimal Media+5-fluoroorotic acid ["MM+5-FOA"] selection plates and maintained at 30° C. for 2 to 5 days. MM+5-FOA comprises (per liter): 20 g glucose, 6.7 g Yeast Nitrogen base, 75 mg uracil, 75 mg uridine and an appropriate amount of FOA (Zymo Research Corp., Orange, Calif.), based on FOA activity testing against a range of concentrations from 100 mg/L to 1000 mg/L (since variation occurs within each batch received from the supplier).

Further experiments determined that only the third group of transformants possessed a real Ura-phenotype.

The Ura-cells were scraped from the MM+5-FOA plates and subjected to fatty acid analysis, according to the General Methods. In this way, GC analyses showed that there were 28.5%, 28.5%, 27.4%, 28.6%, 29.2%, 30.3% and 29.6% EPA of TFAs in pZKUM-transformants #1, #3, #6, #7, #8, #10 and #11 grown on MM+5-FOA plates of group 3, respectively. These seven strains were designated as strains Y9502U12, Y9502U14, Y9502U17, Y9502U18, Y9502U19, Y9502U21 and Y9502U22, respectively (collectively, Y9502U).

Example 9

Identification of a *Yarrowia lipolytica* Gene Having Homology to the *Saccharomyces cerevisiae* Tsa1 Gene An ortholog to the *S. cerevisiae* Tsa1 (GenBank® Accession No. NP_013684; SEQ ID NO:34) ["ScTsa1"] was identified in *Yarrowia lipolytica* by conducting BLAST searches using ScTsa1 as the query sequence against the public *Y. lipolytica* protein database of the "Yeast project *Genolevures*" (Center for Bioinformatics, LaBRI, Talence Cedex, France) (see also Dujon, B. et al., *Nature,* 430 (6995):35-44 (2004)).

The protein sequence having the best homology (with an expectation value of 1e-82) to ScTsa1 among all *Y. lipolytica* proteins, YALI0B15125g (GenBank Accession No. XP_500915.1; SEQ ID NO:36), was given the designation "YlTsa1". YALI0B15125g was annotated therein as "highly similar to uniprot|P34760 *Saccharomyces cerevisiae* YML028w TSA1 (ohnolog of YDR453C) *Thioredoxin peroxidase*, acts as both a ribosome-associated and free cytoplasmic antioxidant".

An alignment of ScTsa1 and the putative YlTsa1 is shown in FIG. 7. There are only two Cys residues both in ScTsa1 and YlTsa1. Vertical boxes highlight Cys48 and Cys171 of ScTsa1, important for inter- and intra-molecular interactions (Tachibana, T. et al., *J. Biol. Chem.,* 284:4464-4472 (2009)). The former Cys residue is conserved in YlTsa1, while the latter is shifted two amino acids upstream in YlTsa1 when compared to ScTsa1.

Using the protein sequence encoding YALI0B15125g (SEQ ID NO:36), NCBI BLASTP 2.2.26+ searches were conducted to identify sequences having similarity within the BLAST "nr" database, according to the methodology set forth in Example 1.

A large number of proteins were identified as sharing significant similarity to YALI0B15125 g (SEQ ID NO:36). Table 12 provides a partial summary of those hits having an Expectation value greater or equal to "2e-102" and annotation that specifically identified the protein (i.e., while hits to hypothetical proteins are excluded), although this should not be considered as limiting to the disclosure herein. The proteins in Table 12 shared between 95-100% query coverage with SEQ ID NO:36.

TABLE 12

Genes Sharing Similarity To YlTsa1 (SEQ ID NO: 36)

| Accession | Description | Query coverage | E value |
|---|---|---|---|
| XP_500915.1 | YALI0B15125p [*Yarrowia lipolytica*] >emb\|CAG83166.1\|YALI0B15125p [*Yarrowia lipolytica*] | 100% | 5e−143 |
| XP_002616355.1 | peroxiredoxin TSA1 [*Clavispora lusitaniae* ATCC 42720] | 100% | 4e−117 |
| XP_001485052.1 | peroxiredoxin TSA1 [*Meyerozyma guilliermondii* ATCC 6260] | 100% | 3e−115 |
| EGW31724.1 | peroxiredoxin TSA1 [*Spathaspora passalidarum* NRRL Y-27907] | 100% | 1e−114 |
| XP_001382622.1 | Peroxiredoxin TSA1 [*Scheffersomyces stipitis* CBS 6054] | 100% | 2e−114 |
| XP_002491977.1 | Thioredoxin peroxidase, acts as both a ribosome-associated and free cytoplasmic antioxidant [*Komagataella pastoris* GS115] | 99% | 4e−113 |
| XP_001526168.1 | peroxiredoxin TSA1 [*Lodderomyces elongisporus* NRRL YB-4239] | 100% | 4e−112 |
| EFW97887.1 | putative peroxiredoxin [*Ogataea parapolymorpha* DL-1] | 98% | 5e−111 |
| ACV49765.1 | putative peroxiredoxin [*Ogataea angusta*] | 98% | 1e−110 |
| BAH80187.1 | thioredoxin peroxidase 1 [*Komagataella pastoris*] | 95% | 2e−110 |
| XP_002547929.1 | peroxiredoxin TSA1 [*Candida tropicalis* MYA-3404] | 100% | 2e−110 |
| XP_716082.1 | likely thioredoxin peroxidase [*Candida albicans*] | 100% | 2e−109 |
| XP_002419517.1 | thioredoxin peroxiredoxin, putative; [*Candida dubliniensis* CD36] | 100% | 8e−109 |
| EEU06015.1 | Tsa1p [*Saccharomyces cerevisiae* JAY291] | 100% | 1e−104 |
| NP_013684.1 | Peroxiredoxin TSA1 (also Cytoplasmic thiol peroxidase 1) [*Saccharomyces cerevisiae*] | 100% | 3e−104 |
| EGA57449.1 | Tsa1p [*Saccharomyces cerevisiae* FostersB] | 100% | 2e−102 |

Based on the BLASTP searches, YALI0B15125g (SEQ ID NO:36) shared the best similarity with the Tsa1 peroxiredoxin from *Clavispora lusitaniae* ATCC 42720 (GenBank® Accession No. XP_002616355.1), with 81% identity and 92% similarity with an expectation value of 4e-117, followed by the TSA1 peroxiredoxin from *Meyerozyma guilliermondii* ATCC 6260 with 80% identity and 91% similarity, and an expectation value of 3e-115.

Based on the above analyses, SEQ ID NO:35 was hypothesized to encode the TSA1 peroxiredoxin of *Y. lipolytica* ("YlTsa1"), wherein the protein sequence is set forth as SEQ ID NO:36.

It is hypothesized herein that overexpression of YlTsa1 in a PUFA-producing strain of *Yarrowia lipolytica* will provide increased resistance to oxidative stresses. One beneficial outcome of this increased resistance to oxidative stresses will be increased protection against lipid peroxidation, which will thereby result in increased lipid and PUFA content.

Example 10

Identification of a *Yarrowia lipolytica* Gene Having Homology to the *Saccharomyces cerevisiae* Ybp1 Gene An ortholog to the *S. cerevisiae* Ybp1 (GenBank® Accession No. NP_009775.1; SEQ ID NO:38) ["ScYbp1"] was identified in *Yarrowia lipolytica* by conducting BLAST searches using ScYbp1 as the query sequence against the public *Y. lipolytica* protein database of the "Yeast project *Genolevures*" (Center for Bioinformatics, LaBRI, Talence Cedex, France) (see also Dujon, B. et al., *Nature,* 430 (6995): 35-44 (2004)).

The protein sequence having the best homology (with an expectation value of 5e-22) to ScYbp1 among all *Y. lipolytica* proteins, YALI0B03762g (GenBank Accession No. XP_500469.1; SEQ ID NO:40), was given the designation "YlYbp1". YALI0B03762 g was annotated therein as "weakly similar to uniprot|P53169 *Saccharomyces cerevisiae* YGL060w YBP2 (ohnolog of YBR216C) Central kinetochore associated protein that mediates mitotic progression".

An alignment of ScYbp1 and the putative YlYbp1 is shown in FIG. 8A-B, although little sequence conservation between the proteins is noted.

Using the protein sequence encoding YALI0B03762g (SEQ ID NO:40), NCBI BLASTP 2.2.26+ searches were conducted to identify sequences having similarity within the BLAST "nr" database, according to the methodology set forth in Example 1.

Several proteins were identified as sharing similarity to YALI0B03762g (SEQ ID NO:40). Table 13 provides a partial summary of those hits having an Expectation value greater or equal to "2e-37" and annotation that specifically identified the protein (i.e., while hits to hypothetical proteins and proteins from *Saccharomyces cerevisiae* are excluded), although this should not be considered as limiting to the disclosure herein. The proteins in Table 13 shared between 74-93% query coverage with SEQ ID NO:40.

TABLE 13

Genes Sharing Similarity To YlYbp1 (SEQ ID NO: 40)

| Accession | Description | Query coverage | E value |
|---|---|---|---|
| XP_001386941.2 | YAP1 binding protein 2 (YBP2) [*Scheffersomyces stipitis* CBS 6054] | 75% | 6e−53 |
| EGV63342.1 | YAP1 binding protein 2 [*Candida tenuis* ATCC 10573] | 74% | 3e−48 |
| EGW32572.1 | YAP1 binding protein 2 [*Spathaspora passalidarum* NRRL Y-27907] | 79% | 3e−46 |
| XP_002492586.1 | YAP1-binding protein 1 [*Komagataella pastoris* CBS 7435] | 93% | 5e−46 |
| XP_002417933.1 | redox regulator, putative [*Candida dubliniensis* CD36] | 88% | 9e−38 |
| XP_722350.1 | potential redox regulator [*Candida albicans* SC5314] | 88% | 2e−37 |

Based on the BLASTP searches, YALI0B03762g (SEQ ID NO:40) shared the best similarity with hypothetical protein CLUG_00080 from *Clavispora lusitaniae* ATCC 42720 (GenBank® Accession No. XP_002618921.1), with 28% identity and 48% similarity, and an expectation value of 1 e-54.

Among proteins with known function, the best hit was the YAP1 binding protein 2 from *Scheffersomyces stipitis* CBS 6054 (GenBank® Accession No. XP 001386941.2), with 30% identity and 49% similarity with an expectation value of 6e-53, followed by YAP1 binding protein 2 from *Candida tenuis* ATCC 10573 (GenBank® Accession No. EGV63342.1) with 28% identity and 47% similarity, and an expectation value of 3e-48.

Based on the above analyses, SEQ ID NO:39 was hypothesized to encode the YAP1 binding protein of *Y. lipolytica* ("YlYbp1"), wherein the protein sequence is set forth as SEQ ID NO:40.

The protein sequence set forth in SEQ ID NO:40 was aligned with the following proteins set forth in Table 14, using a CLUSTAL W (1.81) multiple sequence alignment (FIG. 9A-E; Thompson J. D., et al., *Nucleic Acids Res.* 22:4673-4680 (1994)) to further evaluate YlYbp1. It is hypothesized that each of these proteins encode a homolog of Ybp1.

TABLE 14

Proteins Aligned With YlYbp1 (SEQ ID NO: 40)

| Protein | Annotation | GenBank Accession No. | SEQ ID NO |
|---|---|---|---|
| *Saccharomyces cerevisiae* S288c Ybp1 | Protein required for oxidation of specific cysteine residues of the transcription factor Yap1p, resulting in the nuclear localization of Yap1p in response to stress | NP_009775.1 | 38 |
| *Candida glabrata* unnamed protein product CAGL0K06743g | similar to uniprot\|P38315 *S. cerevisiae* YBR216c | CAG61477.1 | 43 |
| *Kluyveromyces lactis* NRRL Y-1140 hypothetical protein KLLA-ORF8035 | similar to uniprot\|P38315 *S. cerevisiae* YBR216C YBP1 and to uniprot\|P53169 *S. cerevisiae* YGL060W YBP2 | XP_452453.1 | 44 |
| *Scheffersomyces stipitis* CBS 6054 (*Pichia stipitis* CBS 6054) YAP1 binding protein 2 (YBP2) | required for the oxidative stress response to peroxides via the Yap1p transcription factor | XP_001386941.2 | 45 |
| *Zygosaccharomyces rouxii* CBS 732 Hypothetical protein ZYRO-ORF6798 | — | XP_002495870.1 | 46 |
| *Candida albicans* SC5314 YBP1 (CaO19.5034) | similar to *S. cerevisiae* YBP1 (YBR216C) redox regulator of thioredoxin transcriptional regulatory factor YAP1 | XP_722236.1 | 47 |

Relatively few regions of sequence conservation were observed between the proteins upon visual inspection of the alignment. However, each of the seven proteins was included within the kinetochor_Ybp2 super family (Pfam08568; described as a family of proteins integrally involved in the central kinetochore) upon analysis using the "Identify Conserved Domains" tool of National Center for Biotechnology Information ["NCBI"] to view conserved domains detected within the protein sequence using a CD-search (Marchler-Bauer, A. and S. H. Bryant, *Nucleic Acids Res.,* 32(W)327-331 (2004); Marchler-Bauer, A. et al., *Nucleic Acids Res.,* 37(D)205-210 (2009); and Marchler-Bauer, A. et al., *Nucleic Acids Res.,* 39(D)225-229 (2011)). Thus, this distinctive feature may be useful as a means to identify other Ybp1 proteins from other organisms.

It is hypothesized herein that overexpression of YlYbp1 in a PUFA-producing strain of *Yarrowia lipolytica* will provide increased resistance to oxidative stresses. One beneficial outcome of this increased resistance to oxidative stresses will be increased protection against lipid peroxidation, which will thereby result in increased lipid and PUFA content.

What is claimed is:

1. A transgenic oleaginous yeast having increased oil content and increased Yap1 transcription factor activity, wherein the increased oil content is compared to the oil content of a non-transgenic oleaginous yeast, and wherein the increased Yap1 transcription factor activity results from:

(i) overexpressing the Yap1 transcription factor, wherein the Yap1 transcription factor comprises an amino acid sequence that is at least 90% identical to SEQ ID NO:4;

(ii) overexpressing a Gpx3 protein, wherein the Gpx3 protein comprises an amino acid sequence that is at least 90% identical to SEQ ID NO:28; or (iii) a combination of (i) and (ii).

2. The transgenic oleaginous yeast of claim 1, wherein the Yap1 transcription factor comprises the amino acid sequence.

3. The transgenic oleaginous yeast of claim 1, wherein the Gpx3 protein comprises the amino acid sequence of SEQ ID NO:28.

4. The transgenic oleaginous yeast of claim 1, wherein the transgenic oleaginous yeast is from a genus selected from the group consisting of: *Yarrowia, Candida, Rhodotorula, Rhodosporidium, Cryptococcus, Trichosporon*, and *Lipomyces.*

5. The transgenic oleaginous yeast of claim 4, wherein the transgenic oleaginous yeast is *Yarrowia lipolytica.*

6. The transgenic oleaginous yeast of claim 1, wherein the transgenic oleaginous yeast produces at least one polyunsaturated fatty acid.

7. A method of increasing oil content in an oleaginous yeast comprising:

a) engineering the oleaginous yeast to overexpress a protein selected from the group consisting of:

(i) a Yap1 transcription factor, wherein the Yap1 transcription factor comprises an amino acid sequence that is at least 90% identical to SEQ ID NO:4;

(ii) a Gpx3 protein, wherein the Gpx3 protein comprises an amino acid sequence that is at least 90% identical to SEQ ID NO:28; and (iii) a combination of (a) and (b); and b) growing the oleaginous yeast of (a) under suitable conditions to result in increased oil content when compared to the oil content of a non-transgenic oleaginous yeast.

8. The transgenic oleaginous yeast of claim 6, wherein the transgenic oleaginous yeast produces eicosapentaenoic acid.

9. The transgenic oleaginous yeast of claim 5, wherein the *Yarrowia lipolytica* produces eicosapentaenoic acid.

10. The transgenic oleaginous yeast of claim 1, wherein the increased Yap1 transcription factor activity results from overexpressing the Yap1 transcription factor.

* * * * *

SEQUENCE LISTING

```
<160> NUMBER OF SEQ ID NOS: 47

<210> SEQ ID NO 1
<211> LENGTH: 1953
<212> TYPE: DNA
<213> ORGANISM: Saccharomyces cerevisiae
<220> FEATURE:
<221> NAME/KEY: CDS
<222> LOCATION: (1)..(1953)
<223> OTHER INFORMATION: GenBank Accession No. NM_001182362

<400> SEQUENCE: 1

atg agt gtg tct acc gcc aag agg tcg ctg gat gtc gtt tct ccg ggt      48
Met Ser Val Ser Thr Ala Lys Arg Ser Leu Asp Val Val Ser Pro Gly
1               5                   10                  15

tca tta gcg gag ttt gag ggt tca aaa tct cgt cac gat gaa ata gaa      96
Ser Leu Ala Glu Phe Glu Gly Ser Lys Ser Arg His Asp Glu Ile Glu
            20                  25                  30

aat gaa cat aga cgt act ggt aca cgt gat ggc gag gat agc gag caa     144
Asn Glu His Arg Arg Thr Gly Thr Arg Asp Gly Glu Asp Ser Glu Gln
        35                  40                  45

ccg aag aag aag ggt agc aaa act agc aaa aag caa gat ttg gat cct     192
Pro Lys Lys Lys Gly Ser Lys Thr Ser Lys Lys Gln Asp Leu Asp Pro
    50                  55                  60

gaa act aag cag aag agg act gcc caa aat cgg gcc gct caa aga gct     240
Glu Thr Lys Gln Lys Arg Thr Ala Gln Asn Arg Ala Ala Gln Arg Ala
65                  70                  75                  80

ttt agg gaa cgt aag gag agg aag atg aag gaa ttg gag aag aag gta     288
Phe Arg Glu Arg Lys Glu Arg Lys Met Lys Glu Leu Glu Lys Lys Val
                85                  90                  95

caa agt tta gag agt att cag cag caa aat gaa gtg gaa gct act ttt     336
Gln Ser Leu Glu Ser Ile Gln Gln Gln Asn Glu Val Glu Ala Thr Phe
            100                 105                 110

ttg agg gac cag tta atc act ctg gtg aat gag tta aaa aaa tat aga     384
Leu Arg Asp Gln Leu Ile Thr Leu Val Asn Glu Leu Lys Lys Tyr Arg
        115                 120                 125

cca gag aca aga aat gac tca aaa gtg ctg gaa tat tta gca agg cga     432
Pro Glu Thr Arg Asn Asp Ser Lys Val Leu Glu Tyr Leu Ala Arg Arg
    130                 135                 140

gat cct aat ttg cat ttt tca aaa aat aac gtt aac cac agc aat agc     480
Asp Pro Asn Leu His Phe Ser Lys Asn Asn Val Asn His Ser Asn Ser
145                 150                 155                 160

gag cca att gac aca ccc aat gat gac ata caa gaa aat gtt aaa caa     528
Glu Pro Ile Asp Thr Pro Asn Asp Asp Ile Gln Glu Asn Val Lys Gln
                165                 170                 175

aag atg aat ttc acg ttt caa tat ccg ctt gat aac gac aac gac aac     576
Lys Met Asn Phe Thr Phe Gln Tyr Pro Leu Asp Asn Asp Asn Asp Asn
            180                 185                 190

gac aac agt aaa aat gtg ggg aaa caa tta cct tca cca aat gat cca     624
Asp Asn Ser Lys Asn Val Gly Lys Gln Leu Pro Ser Pro Asn Asp Pro
        195                 200                 205
```

-continued

```
agt cat tcg gct cct atg cct ata aat cag aca caa aag aaa tta agt      672
Ser His Ser Ala Pro Met Pro Ile Asn Gln Thr Gln Lys Lys Leu Ser
    210                 215                 220

gac gct aca gat tcc tcc agc gct act ttg gat tcc ctt tca aat agt      720
Asp Ala Thr Asp Ser Ser Ser Ala Thr Leu Asp Ser Leu Ser Asn Ser
225                 230                 235                 240

aac gat gtt ctt aat aac aca cca aac tcc tcc act tcg atg gat tgg      768
Asn Asp Val Leu Asn Asn Thr Pro Asn Ser Ser Thr Ser Met Asp Trp
                245                 250                 255

tta gat aat gta ata tat act aac agg ttt gtg tca ggt gat gat ggc      816
Leu Asp Asn Val Ile Tyr Thr Asn Arg Phe Val Ser Gly Asp Asp Gly
            260                 265                 270

agc aat agt aaa act aag aat tta gac agt aat atg ttt tct aat gac      864
Ser Asn Ser Lys Thr Lys Asn Leu Asp Ser Asn Met Phe Ser Asn Asp
        275                 280                 285

ttt aat ttt gaa aac caa ttt gat gaa caa gtt tcg gag ttt tgt tcg      912
Phe Asn Phe Glu Asn Gln Phe Asp Glu Gln Val Ser Glu Phe Cys Ser
    290                 295                 300

aaa atg aac cag gta tgt gga aca agg caa tgt ccc att ccc aag aaa      960
Lys Met Asn Gln Val Cys Gly Thr Arg Gln Cys Pro Ile Pro Lys Lys
305                 310                 315                 320

ccc atc tcg gct ctt gat aaa gaa gtt ttc gcg tca tct tct ata cta     1008
Pro Ile Ser Ala Leu Asp Lys Glu Val Phe Ala Ser Ser Ser Ile Leu
                325                 330                 335

agt tca aat tct cct gct tta aca aat act tgg gaa tca cat tct aat     1056
Ser Ser Asn Ser Pro Ala Leu Thr Asn Thr Trp Glu Ser His Ser Asn
            340                 345                 350

att aca gat aat act cct gct aat gtc att gct act gat gct act aaa     1104
Ile Thr Asp Asn Thr Pro Ala Asn Val Ile Ala Thr Asp Ala Thr Lys
        355                 360                 365

tat gaa aat tcc ttc tcc ggt ttt ggc cga ctt ggt ttc gat atg agt     1152
Tyr Glu Asn Ser Phe Ser Gly Phe Gly Arg Leu Gly Phe Asp Met Ser
    370                 375                 380

gcc aat cat tac gtc gtg aat gat aat agc act ggt agc act gat agc     1200
Ala Asn His Tyr Val Val Asn Asp Asn Ser Thr Gly Ser Thr Asp Ser
385                 390                 395                 400

act ggt agc act ggc aat aag aac aaa aag aac aat aat aat agc gat     1248
Thr Gly Ser Thr Gly Asn Lys Asn Lys Lys Asn Asn Asn Asn Ser Asp
                405                 410                 415

gat gta ctc cca ttc ata tcc gag tca ccg ttt gat atg aac caa gtt     1296
Asp Val Leu Pro Phe Ile Ser Glu Ser Pro Phe Asp Met Asn Gln Val
            420                 425                 430

act aat ttt ttt agt ccg gga tct acc ggc atc ggc aat aat gct gcc     1344
Thr Asn Phe Phe Ser Pro Gly Ser Thr Gly Ile Gly Asn Asn Ala Ala
        435                 440                 445

tct aac acc aat ccc agc cta ctg caa agc agc aaa gag gat ata cct     1392
Ser Asn Thr Asn Pro Ser Leu Leu Gln Ser Ser Lys Glu Asp Ile Pro
    450                 455                 460

ttt atc aac gca aat ctg gct ttc cca gac gac aat tca act aat att     1440
Phe Ile Asn Ala Asn Leu Ala Phe Pro Asp Asp Asn Ser Thr Asn Ile
465                 470                 475                 480

caa tta caa cct ttc tct gaa tct caa tct caa aat aag ttt gac tac     1488
Gln Leu Gln Pro Phe Ser Glu Ser Gln Ser Gln Asn Lys Phe Asp Tyr
                485                 490                 495

gac atg ttt ttt aga gat tca tcg aag gaa ggt aac aat tta ttt gga     1536
Asp Met Phe Phe Arg Asp Ser Ser Lys Glu Gly Asn Asn Leu Phe Gly
            500                 505                 510
```

```
gag ttt tta gag gat gac gat gat gac aaa aaa gcc gct aat atg tca      1584
Glu Phe Leu Glu Asp Asp Asp Asp Asp Lys Lys Ala Ala Asn Met Ser
        515                 520                 525

gac gat gag tca agt tta atc aag aac cag tta att aac gaa gaa cca      1632
Asp Asp Glu Ser Ser Leu Ile Lys Asn Gln Leu Ile Asn Glu Glu Pro
    530                 535                 540

gag ctt ccg aaa caa tat cta caa tcg gta cca gga aat gaa agc gaa      1680
Glu Leu Pro Lys Gln Tyr Leu Gln Ser Val Pro Gly Asn Glu Ser Glu
545                 550                 555                 560

atc tca caa aaa aat ggc agt agt tta cag aat gct gac aaa atc aat      1728
Ile Ser Gln Lys Asn Gly Ser Ser Leu Gln Asn Ala Asp Lys Ile Asn
                565                 570                 575

aat ggc aat gat aac gat aat gat aat gat gtc gtt cca tct aag gaa      1776
Asn Gly Asn Asp Asn Asp Asn Asp Asn Asp Val Val Pro Ser Lys Glu
            580                 585                 590

ggc tct tta cta agg tgt tcg gaa att tgg gat aga ata aca aca cat      1824
Gly Ser Leu Leu Arg Cys Ser Glu Ile Trp Asp Arg Ile Thr Thr His
        595                 600                 605

ccg aaa tac tca gat att gat gtc gat ggt tta tgt tcc gag cta atg      1872
Pro Lys Tyr Ser Asp Ile Asp Val Asp Gly Leu Cys Ser Glu Leu Met
    610                 615                 620

gca aag gca aaa tgt tca gaa aga ggg gtt gtc atc aat gca gaa gac      1920
Ala Lys Ala Lys Cys Ser Glu Arg Gly Val Val Ile Asn Ala Glu Asp
625                 630                 635                 640

gtt caa tta gct ttg aat aag cat atg aac taa                          1953
Val Gln Leu Ala Leu Asn Lys His Met Asn
                645                 650


<210> SEQ ID NO 2
<211> LENGTH: 650
<212> TYPE: PRT
<213> ORGANISM: Saccharomyces cerevisiae

<400> SEQUENCE: 2

Met Ser Val Ser Thr Ala Lys Arg Ser Leu Asp Val Val Ser Pro Gly
1               5                   10                  15

Ser Leu Ala Glu Phe Glu Gly Ser Lys Ser Arg His Asp Glu Ile Glu
            20                  25                  30

Asn Glu His Arg Arg Thr Gly Thr Arg Asp Gly Glu Asp Ser Glu Gln
        35                  40                  45

Pro Lys Lys Lys Gly Ser Lys Thr Ser Lys Lys Gln Asp Leu Asp Pro
    50                  55                  60

Glu Thr Lys Gln Lys Arg Thr Ala Gln Asn Arg Ala Ala Gln Arg Ala
65                  70                  75                  80

Phe Arg Glu Arg Lys Glu Arg Lys Met Lys Glu Leu Glu Lys Lys Val
                85                  90                  95

Gln Ser Leu Glu Ser Ile Gln Gln Gln Asn Glu Val Glu Ala Thr Phe
            100                 105                 110

Leu Arg Asp Gln Leu Ile Thr Leu Val Asn Glu Leu Lys Lys Tyr Arg
        115                 120                 125

Pro Glu Thr Arg Asn Asp Ser Lys Val Leu Glu Tyr Leu Ala Arg Arg
    130                 135                 140

Asp Pro Asn Leu His Phe Ser Lys Asn Asn Val Asn His Ser Asn Ser
145                 150                 155                 160

Glu Pro Ile Asp Thr Pro Asn Asp Asp Ile Gln Glu Asn Val Lys Gln
                165                 170                 175

Lys Met Asn Phe Thr Phe Gln Tyr Pro Leu Asp Asn Asp Asn Asp Asn
            180                 185                 190
```

```
Asp Asn Ser Lys Asn Val Gly Lys Gln Leu Pro Ser Pro Asn Asp Pro
        195                 200                 205

Ser His Ser Ala Pro Met Pro Ile Asn Gln Thr Gln Lys Lys Leu Ser
    210                 215                 220

Asp Ala Thr Asp Ser Ser Ser Ala Thr Leu Asp Ser Leu Ser Asn Ser
225                 230                 235                 240

Asn Asp Val Leu Asn Asn Thr Pro Asn Ser Ser Thr Ser Met Asp Trp
                245                 250                 255

Leu Asp Asn Val Ile Tyr Thr Asn Arg Phe Val Ser Gly Asp Asp Gly
            260                 265                 270

Ser Asn Ser Lys Thr Lys Asn Leu Asp Ser Asn Met Phe Ser Asn Asp
        275                 280                 285

Phe Asn Phe Glu Asn Gln Phe Asp Glu Gln Val Ser Glu Phe Cys Ser
    290                 295                 300

Lys Met Asn Gln Val Cys Gly Thr Arg Gln Cys Pro Ile Pro Lys Lys
305                 310                 315                 320

Pro Ile Ser Ala Leu Asp Lys Glu Val Phe Ala Ser Ser Ser Ile Leu
                325                 330                 335

Ser Ser Asn Ser Pro Ala Leu Thr Asn Thr Trp Glu Ser His Ser Asn
            340                 345                 350

Ile Thr Asp Asn Thr Pro Ala Asn Val Ile Ala Thr Asp Ala Thr Lys
        355                 360                 365

Tyr Glu Asn Ser Phe Ser Gly Phe Gly Arg Leu Gly Phe Asp Met Ser
    370                 375                 380

Ala Asn His Tyr Val Val Asn Asp Asn Ser Thr Gly Ser Thr Asp Ser
385                 390                 395                 400

Thr Gly Ser Thr Gly Asn Lys Asn Lys Lys Asn Asn Asn Asn Ser Asp
                405                 410                 415

Asp Val Leu Pro Phe Ile Ser Glu Ser Pro Phe Asp Met Asn Gln Val
            420                 425                 430

Thr Asn Phe Phe Ser Pro Gly Ser Thr Gly Ile Gly Asn Asn Ala Ala
        435                 440                 445

Ser Asn Thr Asn Pro Ser Leu Leu Gln Ser Ser Lys Glu Asp Ile Pro
    450                 455                 460

Phe Ile Asn Ala Asn Leu Ala Phe Pro Asp Asp Asn Ser Thr Asn Ile
465                 470                 475                 480

Gln Leu Gln Pro Phe Ser Glu Ser Gln Ser Gln Asn Lys Phe Asp Tyr
                485                 490                 495

Asp Met Phe Phe Arg Asp Ser Ser Lys Glu Gly Asn Asn Leu Phe Gly
            500                 505                 510

Glu Phe Leu Glu Asp Asp Asp Asp Asp Lys Lys Ala Ala Asn Met Ser
        515                 520                 525

Asp Asp Glu Ser Ser Leu Ile Lys Asn Gln Leu Ile Asn Glu Glu Pro
    530                 535                 540

Glu Leu Pro Lys Gln Tyr Leu Gln Ser Val Pro Gly Asn Glu Ser Glu
545                 550                 555                 560

Ile Ser Gln Lys Asn Gly Ser Ser Leu Gln Asn Ala Asp Lys Ile Asn
                565                 570                 575

Asn Gly Asn Asp Asn Asp Asn Asp Asn Asp Val Val Pro Ser Lys Glu
            580                 585                 590

Gly Ser Leu Leu Arg Cys Ser Glu Ile Trp Asp Arg Ile Thr Thr His
        595                 600                 605
```

```
Pro Lys Tyr Ser Asp Ile Asp Val Asp Gly Leu Cys Ser Glu Leu Met
    610                 615                 620

Ala Lys Ala Lys Cys Ser Glu Arg Gly Val Val Ile Asn Ala Glu Asp
625                 630                 635                 640

Val Gln Leu Ala Leu Asn Lys His Met Asn
                645                 650


<210> SEQ ID NO 3
<211> LENGTH: 1605
<212> TYPE: DNA
<213> ORGANISM: Yarrowia lipolytica
<220> FEATURE:
<221> NAME/KEY: CDS
<222> LOCATION: (1)..(1605)
<223> OTHER INFORMATION: YALI0F03388; GenBank Accession No. XM_504945

<400> SEQUENCE: 3

atg tac tca gac tac aac att cct ggt gcc atg ccg gcg tcc atg gcc       48
Met Tyr Ser Asp Tyr Asn Ile Pro Gly Ala Met Pro Ala Ser Met Ala
1               5                   10                  15

atg cct ccg ttc aaa cag gag ttt gac tac gcc caa tac gac ctt aac       96
Met Pro Pro Phe Lys Gln Glu Phe Asp Tyr Ala Gln Tyr Asp Leu Asn
            20                  25                  30

cag ccc ctg ccc ccg cag cag caa caa cag cct atc gac ctg acc cct      144
Gln Pro Leu Pro Pro Gln Gln Gln Gln Gln Pro Ile Asp Leu Thr Pro
        35                  40                  45

gga ggg ccc ctc ccc gtc tcg gat tac tcg acg tcg tca tac acc ctg      192
Gly Gly Pro Leu Pro Val Ser Asp Tyr Ser Thr Ser Ser Tyr Thr Leu
    50                  55                  60

gac aac gac tca cag aag cga aaa atg tcc ccg gga gag tcc acc agt      240
Asp Asn Asp Ser Gln Lys Arg Lys Met Ser Pro Gly Glu Ser Thr Ser
65                  70                  75                  80

gac gga ggc gcc gac gac gag tct cca gaa gga gat gac ggt gag gcc      288
Asp Gly Gly Ala Asp Asp Glu Ser Pro Glu Gly Asp Asp Gly Glu Ala
                85                  90                  95

gac ccc aag aag ccc cga aag ccc ggc cga aag ccc gaa acc acc atc      336
Asp Pro Lys Lys Pro Arg Lys Pro Gly Arg Lys Pro Glu Thr Thr Ile
            100                 105                 110

ccc gcg tcc aaa cgc aag gct cag aac cgg gct gcc caa agg gcc ttc      384
Pro Ala Ser Lys Arg Lys Ala Gln Asn Arg Ala Ala Gln Arg Ala Phe
        115                 120                 125

aga gag cga aag gaa aag cat ctg cgc gac ctg gaa acc aaa ata tct      432
Arg Glu Arg Lys Glu Lys His Leu Arg Asp Leu Glu Thr Lys Ile Ser
    130                 135                 140

cag ctc gag ggc gag acg gca gcc aaa aac tcg gaa aac gag ttc ctg      480
Gln Leu Glu Gly Glu Thr Ala Ala Lys Asn Ser Glu Asn Glu Phe Leu
145                 150                 155                 160

cgc ttc cag gtc cag cgg ctt cag aac gag ctc aag ctt tac cgt gag      528
Arg Phe Gln Val Gln Arg Leu Gln Asn Glu Leu Lys Leu Tyr Arg Glu
                165                 170                 175

aag cct gcc ggc act tcg gga gcc tct gga gtc tct gga gcc gga gca      576
Lys Pro Ala Gly Thr Ser Gly Ala Ser Gly Val Ser Gly Ala Gly Ala
            180                 185                 190

ccc gct tca aac gtg cat tcg gct ccc atc ccg gag atg tcg tcc aaa      624
Pro Ala Ser Asn Val His Ser Ala Pro Ile Pro Glu Met Ser Ser Lys
        195                 200                 205

ccg ttc acg ttc gag ttc ccc tcg tac aac gtg ccc aag ccg acc gat      672
Pro Phe Thr Phe Glu Phe Pro Ser Tyr Asn Val Pro Lys Pro Thr Asp
    210                 215                 220
```

```
gtg gag cga gag gca cgc gag caa ctg caa cga gag cag atc cga ggc      720
Val Glu Arg Glu Ala Arg Glu Gln Leu Gln Arg Glu Gln Ile Arg Gly
225                 230                 235                 240

tac ttg cag cgc aag ccc tca tct gtg gcc tcc gac acc act tct cct      768
Tyr Leu Gln Arg Lys Pro Ser Ser Val Ala Ser Asp Thr Thr Ser Pro
                245                 250                 255

gca tct caa acc tcg tgc aac cag tct ccc tgc acc aac ccc tcg gca      816
Ala Ser Gln Thr Ser Cys Asn Gln Ser Pro Cys Thr Asn Pro Ser Ala
            260                 265                 270

tac act tcg ccc cag agc cag agt gga agt gtg agc cag cag aag ccc      864
Tyr Thr Ser Pro Gln Ser Gln Ser Gly Ser Val Ser Gln Gln Lys Pro
        275                 280                 285

ctg ttg ggt gct acc atc gct gcc atg aac ggc aag ccc gac ccc cat      912
Leu Leu Gly Ala Thr Ile Ala Ala Met Asn Gly Lys Pro Asp Pro His
    290                 295                 300

gct gtt gac ttt tgt gct gag ctc tcc aag gcc tgt gta aac aag gcc      960
Ala Val Asp Phe Cys Ala Glu Leu Ser Lys Ala Cys Val Asn Lys Ala
305                 310                 315                 320

gag ctg ctg cag cga tcc gcc aca gcc agt gca tct ccc aca acc tcc     1008
Glu Leu Leu Gln Arg Ser Ala Thr Ala Ser Ala Ser Pro Thr Thr Ser
                325                 330                 335

aac acg gtg gta ccg tcc gca gct gca ccg ggt agc act cag cag tcg     1056
Asn Thr Val Val Pro Ser Ala Ala Ala Pro Gly Ser Thr Gln Gln Ser
            340                 345                 350

gca ggc cag ccc tct gta tcc act cct acc tcc tcc aca act gcc cct     1104
Ala Gly Gln Pro Ser Val Ser Thr Pro Thr Ser Ser Thr Thr Ala Pro
        355                 360                 365

cct caa ttg tct gca tct gtc gct aca gcc ggc tct gat ctt ccc gga     1152
Pro Gln Leu Ser Ala Ser Val Ala Thr Ala Gly Ser Asp Leu Pro Gly
    370                 375                 380

tcg gac ttc ctg ttt gac atg ccc ttc gac atg gac ttt atg tcg tac     1200
Ser Asp Phe Leu Phe Asp Met Pro Phe Asp Met Asp Phe Met Ser Tyr
385                 390                 395                 400

cga gac ccc gtt tcc gag acg gca cat ctg gac gac ttt tcg ctg ccc     1248
Arg Asp Pro Val Ser Glu Thr Ala His Leu Asp Asp Phe Ser Leu Pro
                405                 410                 415

gag ctc acg aca gaa aca tcc atg ttt gat cct ctg gac ccc cat tcc     1296
Glu Leu Thr Thr Glu Thr Ser Met Phe Asp Pro Leu Asp Pro His Ser
            420                 425                 430

agc agc gac gtt att tct ggc aag cct ctg tct acc atg ggc gct aca     1344
Ser Ser Asp Val Ile Ser Gly Lys Pro Leu Ser Thr Met Gly Ala Thr
        435                 440                 445

cac agt ggt gtc aac aac gga cag gga agt ggt gct ccc gaa gtc aag     1392
His Ser Gly Val Asn Asn Gly Gln Gly Ser Gly Ala Pro Glu Val Lys
    450                 455                 460

aag gag gag gat gag gac ctg ctc atg ttc tcc aag ccc aag acg ctc     1440
Lys Glu Glu Asp Glu Asp Leu Leu Met Phe Ser Lys Pro Lys Thr Leu
465                 470                 475                 480

atg aac tgc acc gct gtg tgg gac cgt atc acg tcg cat ccc aag ttt     1488
Met Asn Cys Thr Ala Val Trp Asp Arg Ile Thr Ser His Pro Lys Phe
                485                 490                 495

ggc gat atc gac atc gag ggc ctg tgt tcg gag ctg cga aac aag gca     1536
Gly Asp Ile Asp Ile Glu Gly Leu Cys Ser Glu Leu Arg Asn Lys Ala
            500                 505                 510

aag tgc agt gag agt ggc gtc gtg ttg acg gag ttg gac gtg gat ggt     1584
Lys Cys Ser Glu Ser Gly Val Val Leu Thr Glu Leu Asp Val Asp Gly
        515                 520                 525

gtc ctg tca acg ttc cag taa                                         1605
Val Leu Ser Thr Phe Gln
    530
```

<210> SEQ ID NO 4
<211> LENGTH: 534
<212> TYPE: PRT
<213> ORGANISM: Yarrowia lipolytica

<400> SEQUENCE: 4

```
Met Tyr Ser Asp Tyr Asn Ile Pro Gly Ala Met Pro Ala Ser Met Ala
1               5                   10                  15

Met Pro Pro Phe Lys Gln Glu Phe Asp Tyr Ala Gln Tyr Asp Leu Asn
            20                  25                  30

Gln Pro Leu Pro Pro Gln Gln Gln Gln Gln Pro Ile Asp Leu Thr Pro
        35                  40                  45

Gly Gly Pro Leu Pro Val Ser Asp Tyr Ser Thr Ser Ser Tyr Thr Leu
    50                  55                  60

Asp Asn Asp Ser Gln Lys Arg Lys Met Ser Pro Gly Glu Ser Thr Ser
65                  70                  75                  80

Asp Gly Gly Ala Asp Asp Glu Ser Pro Glu Gly Asp Asp Gly Glu Ala
                85                  90                  95

Asp Pro Lys Lys Pro Arg Lys Pro Gly Arg Lys Pro Glu Thr Thr Ile
            100                 105                 110

Pro Ala Ser Lys Arg Lys Ala Gln Asn Arg Ala Ala Gln Arg Ala Phe
        115                 120                 125

Arg Glu Arg Lys Glu Lys His Leu Arg Asp Leu Glu Thr Lys Ile Ser
    130                 135                 140

Gln Leu Glu Gly Glu Thr Ala Ala Lys Asn Ser Glu Asn Glu Phe Leu
145                 150                 155                 160

Arg Phe Gln Val Gln Arg Leu Gln Asn Glu Leu Lys Leu Tyr Arg Glu
                165                 170                 175

Lys Pro Ala Gly Thr Ser Gly Ala Ser Gly Val Ser Gly Ala Gly Ala
            180                 185                 190

Pro Ala Ser Asn Val His Ser Ala Pro Ile Pro Glu Met Ser Ser Lys
        195                 200                 205

Pro Phe Thr Phe Glu Phe Pro Ser Tyr Asn Val Pro Lys Pro Thr Asp
    210                 215                 220

Val Glu Arg Glu Ala Arg Glu Gln Leu Gln Arg Glu Gln Ile Arg Gly
225                 230                 235                 240

Tyr Leu Gln Arg Lys Pro Ser Ser Val Ala Ser Asp Thr Thr Ser Pro
                245                 250                 255

Ala Ser Gln Thr Ser Cys Asn Gln Ser Pro Cys Thr Asn Pro Ser Ala
            260                 265                 270

Tyr Thr Ser Pro Gln Ser Gln Ser Gly Ser Val Ser Gln Gln Lys Pro
        275                 280                 285

Leu Leu Gly Ala Thr Ile Ala Ala Met Asn Gly Lys Pro Asp Pro His
    290                 295                 300

Ala Val Asp Phe Cys Ala Glu Leu Ser Lys Ala Cys Val Asn Lys Ala
305                 310                 315                 320

Glu Leu Leu Gln Arg Ser Ala Thr Ala Ser Ala Ser Pro Thr Thr Ser
                325                 330                 335

Asn Thr Val Val Pro Ser Ala Ala Ala Pro Gly Ser Thr Gln Gln Ser
            340                 345                 350

Ala Gly Gln Pro Ser Val Ser Thr Pro Thr Ser Ser Thr Thr Ala Pro
        355                 360                 365

Pro Gln Leu Ser Ala Ser Val Ala Thr Ala Gly Ser Asp Leu Pro Gly
    370                 375                 380
```

```
Ser Asp Phe Leu Phe Asp Met Pro Phe Asp Met Asp Phe Met Ser Tyr
385                 390                 395                 400

Arg Asp Pro Val Ser Glu Thr Ala His Leu Asp Asp Phe Ser Leu Pro
                405                 410                 415

Glu Leu Thr Thr Glu Thr Ser Met Phe Asp Pro Leu Asp Pro His Ser
            420                 425                 430

Ser Ser Asp Val Ile Ser Gly Lys Pro Leu Ser Thr Met Gly Ala Thr
        435                 440                 445

His Ser Gly Val Asn Asn Gly Gln Gly Ser Gly Ala Pro Glu Val Lys
    450                 455                 460

Lys Glu Glu Asp Glu Asp Leu Leu Met Phe Ser Lys Pro Lys Thr Leu
465                 470                 475                 480

Met Asn Cys Thr Ala Val Trp Asp Arg Ile Thr Ser His Pro Lys Phe
                485                 490                 495

Gly Asp Ile Asp Ile Glu Gly Leu Cys Ser Glu Leu Arg Asn Lys Ala
            500                 505                 510

Lys Cys Ser Glu Ser Gly Val Val Leu Thr Glu Leu Asp Val Asp Gly
        515                 520                 525

Val Leu Ser Thr Phe Gln
    530
```

<210> SEQ ID NO 5
<211> LENGTH: 7412
<212> TYPE: DNA
<213> ORGANISM: Artificial Sequence
<220> FEATURE:
<223> OTHER INFORMATION: Plasmid pYRH60

<400> SEQUENCE: 5

```
cgacgtcggg cccaattcgc cctatagtga gtcgtattac aattcactgg ccgtcgtttt     60

acaacgtcgt gactgggaaa accctggcgt tacccaactt aatcgccttg cagcacatcc    120

ccctttcgcc agctggcgta atagcgaaga ggcccgcacc gatcgccctt cccaacagtt    180

gcgcagcctg aatggcgaat ggacgcgccc tgtagcggcg cattaagcgc ggcgggtgtg    240

gtggttacgc gcagcgtgac cgctacactt gccagcgccc tagcgcccgc tcctttcgct    300

ttcttccctt cctttctcgc cacgttcgcc ggctttcccc gtcaagctct aaatcggggg    360

ctccctttag ggttccgatt tagtgcttta cggcacctcg accccaaaaa acttgattag    420

ggtgatggtt cacgtagtgg gccatcgccc tgatagacgg tttttcgccc tttgacgttg    480

gagtccacgt tctttaatag tggactcttg ttccaaactg gaacaacact caaccctatc    540

tcggtctatt cttttgattt ataagggatt ttgccgattt cggcctattg gttaaaaaat    600

gagctgattt aacaaaaatt taacgcgaat tttaacaaaa tattaacgct tacaatttcc    660

tgatgcggta ttttctcctt acgcatctgt gcggtatttc acaccgcatc aggtggcact    720

tttcggggaa atgtgcgcgg aacccctatt tgtttatttt tctaaataca ttcaaatatg    780

tatccgctca tgagacaata accctgataa atgcttcaat aatattgaaa aaggaagagt    840

atgagtattc aacatttccg tgtcgccctt attccctttt ttgcggcatt ttgccttcct    900

gtttttgctc acccagaaac gctggtgaaa gtaaaagatg ctgaagatca gttgggtgca    960

cgagtgggtt acatcgaact ggatctcaac agcggtaaga tccttgagag ttttcgcccc   1020

gaagaacgtt ttccaatgat gagcactttt aaagttctgc tatgtggcgc ggtattatcc   1080

cgtattgacg ccgggcaaga gcaactcggt cgccgcatac actattctca gaatgacttg   1140
```

-continued

```
gttgagtact caccagtcac agaaaagcat cttacggatg gcatgacagt aagagaatta   1200
tgcagtgctg ccataaccat gagtgataac actgcggcca acttacttct gacaacgatc   1260
ggaggaccga aggagctaac cgcttttttg cacaacatgg gggatcatgt aactcgcctt   1320
gatcgttggg aaccggagct gaatgaagcc ataccaaacg acgagcgtga caccacgatg   1380
cctgtagcaa tggcaacaac gttgcgcaaa ctattaactg gcgaactact tactctagct   1440
tcccggcaac aattaataga ctggatggag gcggataaag ttgcaggacc acttctgcgc   1500
tcggcccttc cggctggctg gtttattgct gataaatctg gagccggtga gcgtgggtct   1560
cgcggtatca ttgcagcact ggggccagat ggtaagccct cccgtatcgt agttatctac   1620
acgacgggga gtcaggcaac tatggatgaa cgaaatagac agatcgctga gataggtgcc   1680
tcactgatta agcattggta actgtcagac caagtttact catatatact ttagattgat   1740
ttaaaacttc atttttaatt taaaaggatc taggtgaaga tcctttttga taatctcatg   1800
accaaaatcc cttaacgtga gttttcgttc cactgagcgt cagaccccgt agaaaagatc   1860
aaaggatctt cttgagatcc tttttttctg cgcgtaatct gctgcttgca aacaaaaaaa   1920
ccaccgctac cagcggtggt ttgtttgccg gatcaagagc taccaactct ttttccgaag   1980
gtaactggct tcagcagagc gcagatacca aatactgttc ttctagtgta gccgtagtta   2040
ggccaccact tcaagaactc tgtagcaccg cctacatacc tcgctctgct aatcctgtta   2100
ccagtggctg ctgccagtgg cgataagtcg tgtcttaccg ggttggactc aagacgatag   2160
ttaccggata aggcgcagcg gtcgggctga acggggggtt cgtgcacaca gcccagcttg   2220
gagcgaacga cctacaccga actgagatac ctacagcgtg agctatgaga aagcgccacg   2280
cttcccgaag ggagaaaggc ggacaggtat ccggtaagcg gcagggtcgg aacaggagag   2340
cgcacgaggg agcttccagg gggaaacgcc tggtatcttt atagtcctgt cgggtttcgc   2400
cacctctgac ttgagcgtcg atttttgtga tgctcgtcag gggggcggag cctatggaaa   2460
aacgccagca acgcggcctt tttacggttc ctggcctttt gctggccttt tgctcacatg   2520
ttctttcctg cgttatcccc tgattctgtg gataaccgta ttaccgcctt tgagtgagct   2580
gataccgctc gccgcagccg aacgaccgag cgcagcgagt cagtgagcga ggaagcggaa   2640
gagcgcccaa tacgcaaacc gcctctcccc gcgcgttggc cgattcatta atgcagctgg   2700
cgcgcccttg tttcgttagt gtagtgtgtg tgggaggaga gtgtgtgtgc gggagtgcaa   2760
gtggaggtga aatgttgtga aaggttgtga aatgatgtgt aaagggagga taggacgggc   2820
ggaaaagacc gcaagctgta tcattttgaa gctctcgggc ccgcgaagct gtttgcggca   2880
ttaatgtctc cattcgagct cttttggcgg actccaggtg tcgtttctct ccaactacaa   2940
gtactcatac agtagccgca gccgtaaaga cctcagccac tgactcaaca ccgcggttgc   3000
ttctggaacg gtttgaaagc taaaacatct ttaggtgtca gattttggga gggtttcaga   3060
tggtgcggat tgtgcaaagt ggcagaaaag agggcgcagg aggcggattt ttgcgctttt   3120
gaagacacat atgggtttc cgagccctcg aaaccatctc tggccgtttt ccccgtcaaa   3180
aacccccgca tttcacctcc atcgtcgctt ctgctgaagt caccaggtac tcccgcaaat   3240
aagcttcatt cgccactcaa accgtcctgc cttgagataa aagtgcaacg ttgtccacca   3300
acgaaccctg acaagccgct aatcactgta cgacgaactt gaacgaccca gtcgacgatt   3360
tcaacgtaca aagttcctcc gagagtgaca cagaccgacg aacgatcgca cacagaccga   3420
cagcgaccac tcagacagtc cagacatcag acatcagact gaacacaacc aacaagcatt   3480
gaacactgcc cttccaccaa gttcgacacg cagacacaga accgctccaa ccgacacaga   3540
```

```
accgctccaa ccgacacaga accactccaa ccgacacaga acctttccaa ccgacacaga   3600

accgttccaa ccgacgcact actgtttctt gtgtctacac gtacgttgat caagcttgtg   3660

agcggataac aatttcacac aggaaacagc tatgaccatg attacgccaa gctcgaaatt   3720

aaccctcact aaagggaaca aaagctggag ctccaccgcg gacacaatat ctggtcaaat   3780

ttcagtttcg ttacatttaa acggtaggtt agtgcttggt atatgagttg taggcatgac   3840

aatttggaaa ggggtggact ttgggaatat tgtgggattt caataccta gtttgtacag   3900

ggtaattgtt acaaatgata caaagaactg tatttctttt catttgtttt aattggttgt   3960

atatcaagtc cgttagacga gctcagtgcc ttggcttttg gcactgtatt tcatttttag   4020

aggtacacta cattcagtga ggtatggtaa ggttgagggc ataatgaagg caccttgtac   4080

tgacagtcac agacctctca ccgagaattt tatgagatat actcgggttc attttaggct   4140

catcgatacg ctctcatcaa gaatacttct tgagaaccgt ggagaccggg gttcgattcc   4200

ccgtatcgga gtgtttattt tttgctcaac cataccctgg ggtgtgttct gtggagcatt   4260

ctcacttttg gtaaacgaca ttgcttcaag tgcagcggaa tcaaaaagta taaagtgggc   4320

agcgagtata cctgtacaga ctgtaggcga taactcaatc caattacccc ccacaacatg   4380

actggccaaa ctgatctcaa gactttattg aaatcagcaa caccgattct caatgaaggc   4440

acatacttct tctgcaacat tcacttgacg cctaaagttg gtgagaaatg gaccgacaag   4500

acatattctg ctatccacgg actgttgcct gtgtcggtgg ctacaatacg tgagtcagaa   4560

gggctgacgg tggtggttcc caaggaaaag gtcgacgagt atctgtctga ctcgtcattg   4620

ccgcctttgg agtacgactc caactatgag tgtgcttgga tcactttgac gatacattct   4680

tcgttggagg ctgtgggtct gacagctgcg ttttcggcgc ggttggccga caacaatatc   4740

agctgcaacg tcattgctgg ctttcatcat gatcacattt ttgtcggcaa aggcgacgcc   4800

cagagagcca ttgacgttct ttctaatttg gaccgatagc cgtatagtcc agtctatcta   4860

taagttcaac taactcgtaa ctattaccat aacatatact tcactgcccc agataaggtt   4920

ccgataaaaa gttctgcaga ctaaatttat ttcagtctcc tcttcaccac caaaatgccc   4980

tcctacgaag ctcgagctaa cgtccacaag tccgcctttg ccgctcgagt gctcaagctc   5040

gtggcagcca agaaaaccaa cctgtgtgct tctctggatg ttaccaccac caaggagctc   5100

attgagcttg ccgataaggt cggaccttat gtgtgcatga tcaaaaccca tatcgacatc   5160

attgacgact tcacctacgc cggcactgtg ctcccctca aggaacttgc tcttaagcac    5220

ggtttcttcc tgttcgagga cagaaagttc gcagatattg gcaacactgt caagcaccag   5280

taccggtgtc accgaatcgc cgagtggtcc gatatcacca acgcccacgg tgtacccgga   5340

accggaatca ttgctggcct gcgagctggt gccgaggaaa ctgtctctga acagaagaag   5400

gaggacgtct ctgactacga gaactcccag tacaaggagt tcctagtccc ctctcccaac   5460

gagaagctgg ccagaggtct gctcatgctg gccgagctgt cttgcaaggg ctctctggcc   5520

actggcgagt actccaagca gaccattgag cttgcccgat ccgaccccga gtttgtggtt   5580

ggcttcattg cccagaaccg acctaagggc gactctgagg actggcttat tctgaccccc   5640

ggggtgggtc ttgacgacaa gggagacgct ctcggacagc agtaccgaac tgttgaggat   5700

gtcatgtcta ccggaacgga tatcataatt gtcggccgag gtctgtacgg ccagaaccga   5760

gatcctattg aggaggccaa gcgataccag aaggctggct gggaggctta ccagaagatt   5820

aactgttaga ggttagacta tggatatgta atttaactgt gtatatagag agcgtgcaag   5880
```

```
tatggagcgc ttgttcagct tgtatgatgg tcagacgacc tgtctgatcg agtatgtatg   5940

atactgcaca acctgtgtat ccgcatgatc tgtccaatgg ggcatgttgt tgtgtttctc   6000

gatacggaga tgctgggtac agtgctaata cgttgaacta cttatactta tatgaggctc   6060

gaagaaagct gacttgtgta tgacttattc tcaactacat ccccagtcac aataccacca   6120

ctgcactacc actacaccaa aaccatgatc aaaccaccca tggacttcct ggaggcagaa   6180

gaacttgtta tggaaaagct caagagagag aattcaagat actatcaaga catgtgtcgc   6240

aacttaatta aagtagagag catcccaaac aagcagtcgc agtcgcactc atcgatatgc   6300

atatgtgcta cttaactgta cgagtactgt acagtacata cagtacctgt agtgattcac   6360

attcagtcat acagtgcagg agtacttccg cttgtctcac aggctttgtc catgtgccaa   6420

tgagtcagac agacacttgt gcatgaggca gagcacacac atggcttcgt tcaatctgct   6480

gataggtcga cattctggga tctgctcagg ttgttcagat gaccaccttc tttttcaccc   6540

cctctccctg taccaccagg accgtttccg agacccacgt gaccctcaaa ccgtcgctct   6600

tgactttccc caggctctcc acctttgccg gctcaaagct cggcgtctgt ttatccctgt   6660

atccaatttt gcccacgctg gcatagagca gaatctccac ctgtctctcc acgacgtttc   6720

ttgacttgcc aaacttgact gattcagagt agaccccctg ggaggaatgg gaagagtttg   6780

cggagttacc gaacagcgaa gagaaggtgc ctccatgggt ttccatctgc caaacgacga   6840

cacgtgtttc tccgtcgaaa tcgggcccag ggacgctatt agaccctatt cccgtgagtc   6900

cagcaaccat ttttccatcc ggagaaaaga ccaggcccca caccggagca gcatgattgg   6960

aattgaattc ctgggggtca agataggcat actctgagcc gattctcaag tcgtagacaa   7020

tcagagaaca ggtgtcggtg accttaatat ccaggtctct gttgagttca gacagagaag   7080

atcttcgtcg agacacattc ttttcaatca tcacagcagt ggcagtagga taaatagcca   7140

cagccagacg ttgactgggc ttatggaacg tgacaatgta cggaaatgtc tgtgtgattt   7200

gagacagtag agctgtgacc ttggactgca gagaaacgcc tctctggagg gtcgagtgac   7260

gcagcaagtc cggattcagc attttgcaag cagtgtgcat cacaaacggc acaaacatgt   7320

ccatggagga ggattttcgg gtgtggctga agaagctgga aagcacatcg atagctgtga   7380

ttcgcacaac taacggcttg tcgaggtgca tg                                 7412
```

<210> SEQ ID NO 6
<211> LENGTH: 7966
<212> TYPE: DNA
<213> ORGANISM: Artificial Sequence
<220> FEATURE:
<223> OTHER INFORMATION: Plasmid pYPS161

<400> SEQUENCE: 6

```
aaatgtaacg aaactgaaat ttgaccagat attgtgtccg cggtggagct ccagcttttg     60

ttccctttag tgagggttaa tttcgagctt ggcgtaatca tggtcatagc tgtttcctgt    120

gtgaaattgt tatccgctca caagcttcca cacaacgtac gttctggttg gctcggatga    180

tttctgcggc cccagcgtaa ggcaggcgtt ccgtccggat cggtttgggt cggatcggct    240

ttttgattgt cgtattgtcg ctcatgttgg acctggtgtg tagttgtagt gtcagatcag    300

attcaccagc gaatgcatgt gaacttcccc acattttgag ccgaggcaga tttgggttgc    360

ttagtaagca gacgtggcgt tgcaagtaga tgtggcaaat ggggacgaag attccgaggg    420

gatatcatag ttccaagggg atgtcatcat ttgccagctt tcgccgccac ttttgacgag    480

tttttgtggg tcaaataagt ttagttgaac ttttcaaatt tcagttggca ttttgttaat    540
```

```
agaaagggtg ccggtgctgg ggggttcatt cctcgggttg cagatatcct atctgtctta    600
ggggtatctc tttcaatcga caagatgtag ttgggtaaca attatttatt aatattctct    660
ccatccagta cagtactaac atcttgacat ctcagcacaa gtgcatcttc ccaagtgttt    720
gttggagagg ttgttgggta ttacttagga aacagaacac agtacgtgga gatcttggat    780
acatcgtaca tggaggttat ccataaaaaa gaccctccag gactagttac aatgccgtta    840
gatgaggaaa tccacaaccc tgattcacta tgaacatatt atcttccccc aaacttgcga    900
tatatggccc ttgatgatag ccttgatttt acccttgatg gtacctccac gaccaaccga    960
tctgctgttt gaagagatat tttcaaattt gaagtgctca gatctactaa acatgagtcc   1020
agtaattctt tccgtctttc cgatttccga tattcccttt tttagcccga cttttcactg   1080
ctcccatgtc aaacgattag gacttgggag acaatcccac tgtcaaaatc accccgatat   1140
tctctgtaaa acaagtactt cttccacgtg atcttcaaat acctcttcca cgtgaccttc   1200
aaatacctct tcaagtacct cttccacgcg accttcaaag tcccttcaaa tacccttctc   1260
aattctcccc ttctcctcca tagtccttct ctctgactaa gcttgagaat acatgacgct   1320
aagacgaaaa cacactagag accctgagag cctgaacatg catccactct gcagttgcgc   1380
acgtgcctac agcaactatc gggtccagtg ctggatctga cactgcgtct ccctatgaag   1440
aaactgataa acagatctgc actcataaca atgatctgag cgatgaaaac gtgacctcca   1500
cagccacaag tcataatcgg cgcgccagct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgtttttcca taggctccgc ccccctgacg agcatcacaa   1800
aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcat agctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaagaacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgag attatcaaaa aggatcttca cctagatcct   2460
tttaaattaa aaatgaagtt ttaaatcaat ctaaagtata tatgagtaaa cttggtctga   2520
cagttaccaa tgcttaatca gtgaggcacc tatctcagcg atctgtctat ttcgttcatc   2580
catagttgcc tgactccccg tcgtgtagat aactacgata cgggagggct taccatctgg   2640
ccccagtgct gcaatgatac cgcgagaccc acgctcaccg gctccagatt tatcagcaat   2700
aaaccagcca gccggaaggg ccgagcgcag aagtggtcct gcaactttat ccgcctccat   2760
ccagtctatt aattgttgcc gggaagctag agtaagtagt tcgccagtta atagtttgcg   2820
caacgttgtt gccattgcta caggcatcgt ggtgtcacgc tcgtcgtttg gtatggcttc   2880
```

```
attcagctcc ggttcccaac gatcaaggcg agttacatga tcccccatgt tgtgcaaaaa   2940
agcggttagc tccttcggtc ctccgatcgt tgtcagaagt aagttggccg cagtgttatc   3000
actcatggtt atggcagcac tgcataattc tcttactgtc atgccatccg taagatgctt   3060
ttctgtgact ggtgagtact caaccaagtc attctgagaa tagtgtatgc ggcgaccgag   3120
ttgctcttgc ccggcgtcaa tacgggataa taccgcgcca catagcagaa ctttaaaagt   3180
gctcatcatt ggaaaacgtt cttcggggcg aaaactctca aggatcttac cgctgttgag   3240
atccagttcg atgtaaccca ctcgtgcacc caactgatct tcagcatctt ttactttcac   3300
cagcgtttct gggtgagcaa aaacaggaag gcaaaatgcc gcaaaaaagg gaataagggc   3360
gacacggaaa tgttgaatac tcatactctt cctttttcaa tattattgaa gcatttatca   3420
gggttattgt ctcatgagcg gatacatatt tgaatgtatt tagaaaaata aacaaatagg   3480
ggttccgcgc acatttcccc gaaaagtgcc acctgatgcg gtgtgaaata ccgcacagat   3540
gcgtaaggag aaaataccgc atcaggaaat tgtaagcgtt aatattttgt taaaattcgc   3600
gttaaatttt tgttaaatca gctcattttt taaccaatag gccgaaatcg gcaaaatccc   3660
ttataaatca aaagaataga ccgagatagg gttgagtgtt gttccagttt ggaacaagag   3720
tccactatta aagaacgtgg actccaacgt caaagggcga aaaaccgtct atcagggcga   3780
tggcccacta cgtgaaccat caccctaatc aagttttttg gggtcgaggt gccgtaaagc   3840
actaaatcgg aaccctaaag ggagcccccg atttagagct tgacggggaa agccggcgaa   3900
cgtggcgaga aaggaaggga agaaagcgaa aggagcgggc gctagggcgc tggcaagtgt   3960
agcggtcacg ctgcgcgtaa ccaccacacc cgccgcgctt aatgcgccgc tacagggcgc   4020
gtccattcgc cattcaggct gcgcaactgt tgggaagggc gatcggtgcg ggcctcttcg   4080
ctattacgcc agctggcgaa aggggggatgt gctgcaaggc gattaagttg ggtaacgcca   4140
gggttttccc agtcacgacg ttgtaaaacg acggccagtg aattgtaata cgactcacta   4200
tagggcgaat tgggcccgac gtcgcatgca actattagtg aggcttcggg agtggttgtc   4260
tcggttgtct cattcagact cgttgtgttg tatctatatc tatataaaca ctcttgtccc   4320
tcaatcccac tgccatcttt tgctaaactt gccgccaata tgaaactcat ctccctcatc   4380
accgtcgcta ccaccgctct ggcggctgtc ggagacaagt acaagctgac ctataccaga   4440
tcagacgccc aatcggtcga atctctgccc gtcacctacc aagatgacct gatcaccgcc   4500
tccaccgacg gcgaacccat caccatcacc gagggcgagg gcaacacctt ctctgttaac   4560
gacatgccca tcgcctatct ggagctgcag gctttgttct ggaccggcga ctacggctac   4620
aagctccagg gctcggtctt tgacattgcc gccgatggaa cctttgagct gagagacggc   4680
cccaaggagt actactattg cactcctcac cctgagcgaa acgtcatcta cgtcatcaac   4740
agccccgact actccaagtg tcggttcaag cgtaccatca agttccacgc tgaaaagatc   4800
taagtggtaa tcgaccgact aaccattttt agctgacaaa cacttgctaa ctcctataac   4860
gaatgaatga ctaacttggc atattgttac caagtattac ttgggatata gttgagtgta   4920
accattgcta agaatccaaa ctggagcttc taaaggtctg ggagtcgccg tatgtgttca   4980
tatcgaaatc aaagaaatca taatcgcaac agaattcaaa atcaagcaga ttaatatcca   5040
ttattgtact cggatcgtga catatctgat atgatctcgg atatgatctc tgactgttta   5100
ctgggagatt tgttgaagat ttgttgaggt tatctgaaaa gtagacaata gagacaaaat   5160
gacgatatca agaactgaat cgggccgaaa tactcggtat cattcccttc agcagtaact   5220
gtattgctct atcaatgcga cgagatacct ccacaattaa tactgtatac gctctaccac   5280
```

```
tcatatctcc aatgctaaaa tatattcatg cccaggacct ctgtgcactg ctatgcagca   5340
cagtgttgtc gattgaattg gtcgtgtctg gtccctgatg ctctgtgtct cgctgactag   5400
tccttccatc cagacctcgt cattatctga taggcaacaa gttctgctct ctcacaccct   5460
gccgacacaa gggacactcg ggcttctctc tcacccattc ggaaatacag tccttaatta   5520
agttgcgaca catgtcttga tagtatcttg aattctctct cttgagcttt tccataacaa   5580
gttcttctgc ctccaggaag tccatgggtg gtttgatcat ggttttggtg tagtggtagt   5640
gcagtggtgg tattgtgact ggggatgtag ttgagaataa gtcatacaca agtcagcttt   5700
cttcgagcct catataagta taagtagttc aacgtattag cactgtaccc agcatctccg   5760
tatcgagaaa cacaacaaca tgccccattg gacagatcat gcggatacac aggttgtgca   5820
gtatcataca tactcgatca gacaggtcgt ctgaccatca tacaagctga acaagcgctc   5880
catacttgca cgctctctat atacacagtt aaattacata tccatagtct aacctctaac   5940
agttaatctt ctggtaagcc tcccagccag ccttctggta tcgcttggcc tcctcaatag   6000
gatctcggtt ctggccgtac agacctcggc cgacaattat gatatccgtt ccggtagaca   6060
tgacatcctc aacagttcgg tactgctgtc cgagagcgtc tcccttgtcg tcaagaccca   6120
ccccgggggt cagaataagc cagtcctcag agtcgccctt aggtcggttc tgggcaatga   6180
agccaaccac aaactcgggg tcggatcggg caagctcaat ggtctgcttg gagtactcgc   6240
cagtggccag agagcccttg caagacagct cggccagcat gagcagacct ctggccagct   6300
tctcgttggg agaggggact aggaactcct tgtactggga gttctcgtag tcagagacgt   6360
cctccttctt ctgttcagag acagtttcct cggcaccagc tcgcaggcca gcaatgattc   6420
cggttccggg tacaccgtgg gcgttggtga tatcggacca ctcggcgatt cggtgacacc   6480
ggtactggtg cttgacagtg ttgccaatat ctgcgaactt tctgtcctcg aacaggaaga   6540
aaccgtgctt aagagcaagt tccttgaggg ggagcacagt gccggcgtag gtgaagtcgt   6600
caatgatgtc gatatgggtt ttgatcatgc acacataagg tccgacctta tcggcaagct   6660
caatgagctc cttggtggtg gtaacatcca gagaagcaca caggttggtt ttcttggctg   6720
ccacgagctt gagcactcga gcggcaaagg cggacttgtg gacgttagct cgagcttcgt   6780
aggagggcat tttggtggtg aagaggagac tgaaataaat ttagtctgca gaacttttta   6840
tcggaacctt atctggggca gtgaagtata tgttatggta atagttacga gttagttgaa   6900
cttatagata gactggacta tacggctatc ggtccaaatt agaaagaacg tcaatggctc   6960
tctgggcgtc gcctttgccg acaaaaatgt gatcatgatg aaagccagca atgacgttgc   7020
agctgatatt gttgtcggcc aaccgcgccg aaaacgcagc tgtcagaccc acagcctcca   7080
acgaagaatg tatcgtcaaa gtgatccaag cacactcata gttggagtcg tactccaaag   7140
gcggcaatga cgagtcagac agatactcgt cgaccttttc cttgggaacc accaccgtca   7200
gcccttctga ctcacgtatt gtagccaccg acacaggcaa cagtccgtgg atagcagaat   7260
atgtcttgtc ggtccatttc tcaccaactt taggcgtcaa gtgaatgttg cagaagaagt   7320
atgtgccttc attgagaatc ggtgttgctg atttcaataa agtcttgaga tcagtttggc   7380
cagtcatgtt gtgggggta attggattga gttatcgcct acagtctgta caggtatact   7440
cgctgcccac tttatacttt ttgattccgc tgcacttgaa gcaatgtcgt ttaccaaaag   7500
tgagaatgct ccacagaaca caccccaggg tatggttgag caaaaaataa acactccgat   7560
acggggaatc gaaccccggt ctccacggtt ctcaagaagt attcttgatg agagcgtatc   7620
```

```
gatgagccta aaatgaaccc gagtatatct cataaaattc tcggtgagag gtctgtgact   7680

gtcagtacaa ggtgccttca ttatgccctc aaccttacca tacctcactg aatgtagtgt   7740

acctctaaaa atgaaataca gtgccaaaag ccaaggcact gagctcgtct aacggacttg   7800

atatacaacc aattaaaaca aatgaaaaga aatacagttc tttgtatcat ttgtaacaat   7860

taccctgtac aaactaaggt attgaaatcc cacaatattc ccaaagtcca ccccttttcca   7920

aattgtcatg cctacaactc atataccaag cactaaccta ccgttt                 7966


<210> SEQ ID NO 7
<211> LENGTH: 940
<212> TYPE: DNA
<213> ORGANISM: Yarrowia lipolytica

<400> SEQUENCE: 7

cgcgcccttg tttcgttagt gtagtgtgtg tgggaggaga gtgtgtgtgc gggagtgcaa     60

gtggaggtga aatgttgtga aaggttgtga aatgatgtgt aaagggagga taggacgggc    120

ggaaaagacc gcaagctgta tcattttgaa gctctcgggc ccgcgaagct gtttgcggca    180

ttaatgtctc cattcgagct cttttggcgg actccaggtg tcgtttctct ccaactacaa    240

gtactcatac agtagccgca gccgtaaaga cctcagccac tgactcaaca ccgcggttgc    300

ttctggaacg gtttgaaagc taaaacatct ttaggtgtca gattttggga gggtttcaga    360

tggtgcggat tgtgcaaagt ggcagaaaag agggcgcagg aggcggattt ttgcgctttt    420

gaagacacat atgggttttc cgagccctcg aaaccatctc tggccgtttt ccccgtcaaa    480

aacccccgca tttcacctcc atcgtcgctt ctgctgaagt caccaggtac tcccgcaaat    540

aagcttcatt cgccactcaa accgtcctgc cttgagataa aagtgcaacg ttgtccacca    600

acgaaccctg acaagccgct aatcactgta cgacgaactt gaacgaccca gtcgacgatt    660

tcaacgtaca aagttcctcc gagagtgaca cagaccgacg aacgatcgca cacagaccga    720

cagcgaccac tcagacagtc cagacatcag acatcagact gaacacaacc aacaagcatt    780

gaacactgcc cttccaccaa gttcgacacg cagacacaga accgctccaa ccgacacaga    840

accgctccaa ccgacacaga accactccaa ccgacacaga acctttccaa ccgacacaga    900

accgttccaa ccgacgcact actgtttctt gtgtctacac                          940


<210> SEQ ID NO 8
<211> LENGTH: 20
<212> TYPE: DNA
<213> ORGANISM: Artificial Sequence
<220> FEATURE:
<223> OTHER INFORMATION: primer Yl-EF-1214F

<400> SEQUENCE: 8

ccaagcccat gtgtgttgag                                                 20


<210> SEQ ID NO 9
<211> LENGTH: 18
<212> TYPE: DNA
<213> ORGANISM: Artificial Sequence
<220> FEATURE:
<223> OTHER INFORMATION: primer Yl-EF-1270R

<400> SEQUENCE: 9

cggcgaatcg accaagag                                                   18


<210> SEQ ID NO 10
<211> LENGTH: 19
```

<212> TYPE: DNA
<213> ORGANISM: Artificial Sequence
<220> FEATURE:
<223> OTHER INFORMATION: primer YAP1-346F

<400> SEQUENCE: 10
ccaaacgcaa ggctcagaa 19

<210> SEQ ID NO 11
<211> LENGTH: 23
<212> TYPE: DNA
<213> ORGANISM: Artificial Sequence
<220> FEATURE:
<223> OTHER INFORMATION: primer YAP1-409R

<400> SEQUENCE: 11
agatgctttt cctttcgctc tct 23

<210> SEQ ID NO 12
<211> LENGTH: 16
<212> TYPE: DNA
<213> ORGANISM: Artificial Sequence
<220> FEATURE:
<223> OTHER INFORMATION: primer YL-EF-MGB-1235T

<400> SEQUENCE: 12
ccttcactga gtaccc 16

<210> SEQ ID NO 13
<211> LENGTH: 18
<212> TYPE: DNA
<213> ORGANISM: Artificial Sequence
<220> FEATURE:
<223> OTHER INFORMATION: primer YAP1-366T

<400> SEQUENCE: 13
cgggctgccc aaagggcc 18

<210> SEQ ID NO 14
<211> LENGTH: 8043
<212> TYPE: DNA
<213> ORGANISM: Artificial Sequence
<220> FEATURE:
<223> OTHER INFORMATION: Plasmid pYRH61

<400> SEQUENCE: 14
ctagtatgta ctcagactac aacattcctg gtgccatgcc ggcgtccatg gccatgcctc 60
cgttcaaaca ggagtttgac tacgcccaat acgaccttaa ccagcccctg cccccgcagc 120
agcaacaaca gcctatcgac ctgacccctg gagggcccct ccccgtctcg gattactcga 180
cgtcgtcata caccctggac aacgactcac agaagcgaaa aatgtccccg ggagagtcca 240
ccagtgacgg aggcgccgac gacgagtctc cagaaggaga tgacggtgag gccgacccca 300
agaagccccg aaagcccggc cgaaagcccg aaaccaccat ccccgcgtcc aaacgcaagg 360
ctcagaaccg ggctgcccaa agggccttca gagagcgaaa ggaaaagcat ctgcgcgacc 420
tggaaaccaa aatatctcag ctcgagggcg agacggcagc caaaaactcg gaaaacgagt 480
tcctgcgctt ccaggtccag cggcttcaga acgagctcaa gctttaccgt gagaagcctg 540
ccggcacttc gggagcctct ggagtctctg gagccggagc acccgcttca aacgtgcatt 600
cggctcccat cccggagatg tcgtccaaac cgttcacgtt cgagttcccc tcgtacaacg 660
tgcccaagcc gaccgatgtg gagcgagagg cacgcgagca actgcaacga gagcagatcc 720

-continued

```
gaggctactt gcagcgcaag ccctcatctg tggcctccga caccacttct cctgcatctc    780
aaacctcgtg caaccagtct ccctgcacca acccctcggc atacacttcg ccccagagcc    840
agagtggaag tgtgagccag cagaagcccc tgttgggtgc taccatcgct gccatgaacg    900
gcaagcccga cccccatgct gttgactttt gtgctgagct ctccaaggcc tgtgtaaaca    960
aggccgagct gctgcagcga tccgccacag ccagtgcatc tcccacaacc tccaacacgg   1020
tggtaccgtc cgcagctgca ccgggtagca ctcagcagtc ggcaggccag ccctctgtat   1080
ccactcctac ctcctccaca actgcccctc ctcaattgtc tgcatctgtc gctacagccg   1140
gctctgatct tcccggatcg gacttcctgt ttgacatgcc cttcgacatg gactttatgt   1200
cgtaccgaga ccccgtttcc gagacggcac atctggacga cttttcgctg cccgagctca   1260
cgacagaaac atccatgttt gatcctctgg acccccattc cagcagcgac gttatttctg   1320
gcaagcctct gtctaccatg ggcgctacac acagtggtgt caacaacgga cagggaagtg   1380
gtgctcccga agtcaagaag gaggaggatg aggacctgct catgttctcc aagcccaaga   1440
cgctcatgaa ctgcaccgct gtgtgggacc gtatcacgtc gcatcccaag tttggcgata   1500
tcgacatcga gggcctgtgt tcggagctgc gaaacaaggc aaagtgcagt gagagtggcg   1560
tcgtgttgac ggagttggac gtggatggtg tcctgtcaac gttccagtaa gcggccgcgt   1620
taattcaaat taattgatat agtttttttaa tgagtattga atctgtttag aaataatgga   1680
atattatttt tatttattta tttatattat tggtcggctc ttttcttctg aaggtcaatg   1740
acaaaatgat atgaaggaaa taatgatttc taaaatttta caacgtaaga tatttttaca   1800
aaagcctagc tcatcttttg tcatgcacta ttttactcac gcttgaaatt aacggccagt   1860
ccactgcgga gtcatttcaa agtcatccta atcgatctat cgtttttgat agctcatttt   1920
ggagttcgcg attgtcttct gttattcaca actgttttaa tttttatttc attctggaac   1980
tcttcgagtt ctttgtaaag tctttcatag tagcttactt tatcctccaa catatttaac   2040
ttcatgtcaa tttcggctct taaattttcc acatcatcaa gttcaacatc atcttttaac   2100
ttgaatttat tctctagctc ttccaaccaa gcctcattgc tccttgattt actggtgaaa   2160
agtgatacac tttgcgcgca atccaggtca aaactttcct gcaaagaatt caccaatttc   2220
tcgacatcat agtacaattt gttttgttct cccatcacaa tttaatatac ctgatggatt   2280
cttatgaagc gctgggtaat ggacgtgtca ctctacttcg ccttttttccc tactcctttt   2340
agtacggaag acaatgctaa taaataagag ggtaataata atattattaa tcggcaaaaa   2400
agattaaacg ccaagcgttt aattatcaga aagcaaacgt cgtaccaatc cttgaatgct   2460
tcccaattgt atattaagag tcatcacagc aacatattct tgttattaaa ttaattatta   2520
ttgatttttg atattgtata aaaaaaccaa atatgtataa aaaaagtgaa taaaaaatac   2580
caagtatgga gaaatatatt agaagtctat acgttaaacc accgcggtgg agctccaatt   2640
cgccctatag tgagtcgtat tacaattcac tggccgtcgt tttacaacgt cgtgactggg   2700
aaaaccctgg cgttacccaa cttaatcgcc ttgcagcaca tccccccttc gccagctggc   2760
gtaatagcga agaggcccgc accgatcgcc cttcccaaca gttgcgcagc ctgaatggcg   2820
aatggcgcga cgcgccctgt agcggcgcat taagcgcggc gggtgtggtg gttacgcgca   2880
gcgtgaccgc tacacttgcc agcgccctag cgcccgctcc tttcgctttc ttcccttcct   2940
ttctcgccac gttcgccggc tttccccgtc aagctctaaa tcgggggctc cctttagggt   3000
tccgatttag tgctttacgg cacctcgacc ccaaaaaact tgattagggt gatggttcac   3060
gtagtgggcc atcgccctga tagacggttt ttcgcccttt gacgttggag tccacgttct   3120
```

```
ttaatagtgg actcttgttc caaactggaa caacactcaa ccctatctcg gtctattctt   3180
ttgatttata agggattttg ccgatttcgg cctattggtt aaaaaatgag ctgatttaac   3240
aaaaatttaa cgcgaatttt aacaaaatat taacgtttac aatttcctga tgcggtattt   3300
tctccttacg catctgtgcg gtatttcaca ccgcagggta ataactgata taattaaatt   3360
gaagctctaa tttgtgagtt tagtatacat gcatttactt ataatacagt tttttagttt   3420
tgctggccgc atcttctcaa atatgcttcc cagcctgctt ttctgtaacg ttcaccctct   3480
accttagcat cccttccctt tgcaaatagt cctcttccaa caataataat gtcagatcct   3540
gtagagacca catcatccac ggttctatac tgttgaccca atgcgtctcc cttgtcatct   3600
aaacccacac cgggtgtcat aatcaaccaa tcgtaacctt catctcttcc acccatgtct   3660
ctttgagcaa taaagccgat aacaaaatct ttgtcgctct tcgcaatgtc aacagtaccc   3720
ttagtatatt ctccagtaga tagggagccc ttgcatgaca attctgctaa catcaaaagg   3780
cctctaggtt cctttgttac ttcttctgcc gcctgcttca aaccgctaac aatacctggg   3840
cccaccacac cgtgtgcatt cgtaatgtct gcccattctg ctattctgta tacacccgca   3900
gagtactgca atttgactgt attaccaatg tcagcaaatt ttctgtcttc gaagagtaaa   3960
aaattgtact tggcggataa tgcctttagc ggcttaactg tgccctccat ggaaaaatca   4020
gtcaagatat ccacatgtgt ttttagtaaa caaattttgg gacctaatgc ttcaactaac   4080
tccagtaatt ccttggtggt acgaacatcc aatgaagcac acaagtttgt ttgcttttcg   4140
tgcatgatat taaatagctt ggcagcaaca ggactaggat gagtagcagc acgttcctta   4200
tatgtagctt tcgacatgat ttatcttcgt ttcctgcagg tttttgttct gtgcagttgg   4260
gttaagaata ctgggcaatt tcatgtttct tcaacactac atatgcgtat atataccaat   4320
ctaagtctgt gctccttcct tcgttcttcc ttctgttcgg agattaccga atcaaaaaaa   4380
tttcaaagaa accgaaatca aaaaaaagaa taaaaaaaaa atgatgaatt gaattgaaaa   4440
gcgtggtgca ctctcagtac aatctgctct gatgccgcat agttaagcca gccccgacac   4500
ccgccaacac ccgctgacgc gccctgacgg gcttgtctgc tcccggcatc cgcttacaga   4560
caagctgtga ccgtctccgg gagctgcatg tgtcagaggt tttcaccgtc atcaccgaaa   4620
cgcgcgagac gaaagggcct cgtgatacgc ctatttttat aggttaatgt catgataata   4680
atggtttctt aggacggatc gcttgcctgt aacttacacg cgcctcgtat cttttaatga   4740
tggaataatt tgggaattta ctctgtgttt atttattttt atgttttgta tttggatttt   4800
agaaagtaaa taaagaaggt agaagagtta cggaatgaag aaaaaaaaat aaacaaaggt   4860
ttaaaaaatt tcaacaaaaa gcgtacttta catatatatt tattagacaa gaaaagcaga   4920
ttaaatagat atacattcga ttaacgataa gtaaaatgta aaatcacagg attttcgtgt   4980
gtggtcttct acacagacaa gatgaaacaa ttcggcatta atacctgaga gcaggaagag   5040
caagataaaa ggtagtattt gttggcgatc cccctagagt cttttacatc ttcggaaaac   5100
aaaaactatt ttttctttaa tttctttttt tactttctat ttttaattta tatatttata   5160
ttaaaaaatt taaattataa ttatttttat agcacgtgat gaaaaggacc caggtggcac   5220
ttttcgggga aatgtgcgcg gaacccctat ttgtttattt ttctaaatac attcaaatat   5280
gtatccgctc atgagacaat aaccctgata aatgcttcaa taatattgaa aaaggaagag   5340
tatgagtatt caacatttcc gtgtcgccct tattcccttt tttgcggcat tttgccttcc   5400
tgtttttgct cacccagaaa cgctggtgaa agtaaaagat gctgaagatc agttgggtgc   5460
```

```
acgagtgggt tacatcgaac tggatctcaa cagcggtaag atccttgaga gttttcgccc   5520

cgaagaacgt tttccaatga tgagcacttt taaagttctg ctatgtggcg cggtattatc   5580

ccgtattgac gccgggcaag agcaactcgg tcgccgcata cactattctc agaatgactt   5640

ggttgagtac tcaccagtca cagaaaagca tcttacggat ggcatgacag taagagaatt   5700

atgcagtgct gccataacca tgagtgataa cactgcggcc aacttacttc tgacaacgat   5760

cggaggaccg aaggagctaa ccgctttttt tcacaacatg ggggatcatg taactcgcct   5820

tgatcgttgg gaaccggagc tgaatgaagc cataccaaac gacgagcgtg acaccacgat   5880

gcctgtagca atggcaacaa cgttgcgcaa actattaact ggcgaactac ttactctagc   5940

ttcccggcaa caattaatag actggatgga ggcggataaa gttgcaggac cacttctgcg   6000

ctcggccctt ccggctggct ggtttattgc tgataaatct ggagccggtg agcgtgggtc   6060

tcgcggtatc attgcagcac tggggccaga tggtaagccc tcccgtatcg tagttatcta   6120

cacgacgggc agtcaggcaa ctatggatga acgaaataga cagatcgctg agataggtgc   6180

ctcactgatt aagcattggt aactgtcaga ccaagtttac tcatatatac tttagattga   6240

tttaaaactt catttttaat ttaaaaggat ctaggtgaag atcctttttg ataatctcat   6300

gaccaaaatc ccttaacgtg agttttcgtt ccactgagcg tcagaccccg tagaaaagat   6360

caaaggatct tcttgagatc cttttttct gcgcgtaatc tgctgcttgc aaacaaaaaa   6420

accaccgcta ccagcggtgg tttgtttgcc ggatcaagag ctaccaactc tttttccgaa   6480

ggtaactggc ttcagcagag cgcagatacc aaatactgtc cttctagtgt agccgtagtt   6540

aggccaccac ttcaagaact ctgtagcacc gcctacatac ctcgctctgc taatcctgtt   6600

accagtggct gctgccagtg gcgataagtc gtgtcttacc gggttggact caagacgata   6660

gttaccggat aaggcgcagc ggtcgggctg aacggggggt tcgtgcacac agcccagctt   6720

ggagcgaacg acctacaccg aactgagata cctacagcgt gagcattgag aaagcgccac   6780

gcttcccgaa gggagaaagg cggacaggta tccggtaagc ggcagggtcg gaacaggaga   6840

gcgcacgagg gagcttccag ggggaaacgc ctggtatctt tatagtcctg tcgggtttcg   6900

ccacctctga cttgagcgtc gatttttgtg atgctcgtca ggggggccga gcctatggaa   6960

aaacgccagc aacgcggcct ttttacggtt cctggccttt tgctggcctt ttgctcacat   7020

gttctttcct gcgttatccc ctgattctgt ggataaccgt attaccgcct ttgagtgagc   7080

tgataccgct cgccgcagcc gaacgaccga gcgcagcgag tcagtgagcg aggaagcgga   7140

agagcgccca atacgcaaac cgcctctccc cgcgcgttgg ccgattcatt aatgcagctg   7200

gcacgacagg tttcccgact ggaaagcggg cagtgagcgc aacgcaatta atgtgagtta   7260

cctcactcat taggcacccc aggctttaca ctttatgctt ccggctccta tgttgtgtgg   7320

aattgtgagc ggataacaat ttcacacagg aaacagctat gaccatgatt acgccaagct   7380

cggaattaac cctcactaaa gggaacaaaa gctgggtacc gggccccccc tcgaggtcga   7440

cgcctacttg gcttcacata cgttgcatac gtcgatatag ataataatga taatgacagc   7500

aggattatcg taatacgtaa tagttgaaaa tctcaaaaat gtgtgggtca ttacgtaaat   7560

aatgatagga atgggattct tctatttttc ctttttccat tctagcagcc gtcgggaaaa   7620

cgtggcatcc tctctttcgg gctcaattgg agtcacgctg ccgtgagcat cctctctttc   7680

catatctaac aactgagcac gtaaccaatg gaaaagcatg agcttagcgt tgctccaaaa   7740

aagtattgga tggttaatac catttgtctg ttctcttctg actttgactc ctcaaaaaaa   7800

aaaaatctac aatcaacaga tcgcttcaat tacgccctca caaaaacttt tttccttctt   7860
```

```
cttcgcccac gttaaatttt atccctcatg ttgtctaacg gatttctgca cttgatttat   7920

tataaaaaga caaagacata atacttctct atcaatttca gttattgttc ttccttgcgt   7980

tattcttctg ttcttctttt tcttttgtca tatataacca taaccaagta atacatattc   8040

aaa                                                                 8043


<210> SEQ ID NO 15
<211> LENGTH: 48
<212> TYPE: DNA
<213> ORGANISM: Artificial Sequence
<220> FEATURE:
<223> OTHER INFORMATION: primer Yl.Yap1-F-SpeI

<400> SEQUENCE: 15

atattcaaac tagtatgtac tcagactaca acattcctgg tgccatgc                  48


<210> SEQ ID NO 16
<211> LENGTH: 44
<212> TYPE: DNA
<213> ORGANISM: Artificial Sequence
<220> FEATURE:
<223> OTHER INFORMATION: primer Yap1-R

<400> SEQUENCE: 16

gatcaagcgg ccgcttactg gaacgttgac aggacaccat ccac                      44


<210> SEQ ID NO 17
<211> LENGTH: 601
<212> TYPE: DNA
<213> ORGANISM: Saccharomyces cerevisiae

<400> SEQUENCE: 17

gcctacttgg cttcacatac gttgcatacg tcgatataga taataatgat aatgacagca     60

ggattatcgt aatacgtaat agttgaaaat ctcaaaaatg tgtgggtcat tacgtaaata    120

atgataggaa tgggattctt ctatttttcc tttttccatt ctagcagccg tcgggaaaac    180

gtggcatcct ctctttcggg ctcaattgga gtcacgctgc cgtgagcatc ctctctttcc    240

atatctaaca actgagcacg taaccaatgg aaaagcatga gcttagcgtt gctccaaaaa    300

agtattggat ggttaatacc atttgtctgt tctcttctga ctttgactcc tcaaaaaaaa    360

aaaatctaca atcaacagat cgcttcaatt acgccctcac aaaaactttt ttccttcttc    420

ttcgcccacg ttaaatttta tccctcatgt tgtctaacgg atttctgcac ttgatttatt    480

ataaaaagac aaagacataa tacttctcta tcaatttcag ttattgttct tccttgcgtt    540

attcttctgt tcttcttttt cttttgtcat atataaccat aaccaagtaa tacatattca    600

a                                                                    601


<210> SEQ ID NO 18
<211> LENGTH: 1022
<212> TYPE: DNA
<213> ORGANISM: Saccharomyces cerevisiae

<400> SEQUENCE: 18

ggccgcgtta attcaaatta attgatatag ttttttaatg agtattgaat ctgtttagaa     60

ataatggaat attatttta tttatttatt tatattattg gtcggctctt ttcttctgaa    120

ggtcaatgac aaaatgatat gaaggaaata atgatttcta aaattttaca acgtaagata    180

tttttacaaa agcctagctc atcttttgtc atgcactatt ttactcacgc ttgaaattaa    240
```

```
cggccagtcc actgcggagt catttcaaag tcatcctaat cgatctatcg tttttgatag    300

ctcattttgg agttcgcgat tgtcttctgt tattcacaac tgttttaatt tttatttcat    360

tctggaactc ttcgagttct ttgtaaagtc tttcatagta gcttacttta tcctccaaca    420

tatttaactt catgtcaatt tcggctctta aattttccac atcatcaagt tcaacatcat    480

cttttaactt gaatttattc tctagctctt ccaaccaagc ctcattgctc cttgatttac    540

tggtgaaaag tgatacactt tgcgcgcaat ccaggtcaaa actttcctgc aaagaattca    600

ccaatttctc gacatcatag tacaatttgt tttgttctcc catcacaatt taatatacct    660

gatggattct tatgaagcgc tgggtaatgg acgtgtcact ctacttcgcc tttttcccta    720

ctccttttag tacggaagac aatgctaata aataagaggg taataataat attattaatc    780

ggcaaaaaag attaaacgcc aagcgtttaa ttatcagaaa gcaaacgtcg taccaatcct    840

tgaatgcttc ccaattgtat attaagagtc atcacagcaa catattcttg ttattaaatt    900

aattattatt gatttttgat attgtataaa aaaaccaaat atgtataaaa aaagtgaata    960

aaaaatacca agtatggaga aatatattag aagtctatac gttaaaccac cgcggtggag   1020

ct                                                                  1022
```

<210> SEQ ID NO 19
<211> LENGTH: 4887
<212> TYPE: DNA
<213> ORGANISM: Artificial Sequence
<220> FEATURE:
<223> OTHER INFORMATION: Plasmid pRS316

<400> SEQUENCE: 19

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc tttttttga tttcggtttc      240

tttgaaattt ttttgattcg gtaatctccg aacagaagga agaacgaagg aaggagcaca    300

gacttagatt ggtatatata cgcatatgta gtgttgaaga aacatgaaat tgcccagtat    360

tcttaaccca actgcacaga acaaaaacct gcaggaaacg aagataaatc atgtcgaaag    420

ctacatataa ggaacgtgct gctactcatc ctagtcctgt tgctgccaag ctatttaata    480

tcatgcacga aaagcaaaca aacttgtgtg cttcattgga tgttcgtacc accaaggaat    540

tactggagtt agttgaagca ttaggtccca aaatttgttt actaaaaaca catgtggata    600

tcttgactga tttttccatg gagggcacag ttaagccgct aaaggcatta tccgccaagt    660

acaatttttt actcttcgaa gacagaaaat ttgctgacat tggtaataca gtcaaattgc    720

agtactctgc gggtgtatac agaatagcag aatgggcaga cattacgaat gcacacggtg    780

tggtgggccc aggtattgtt agcggtttga agcaggcggc agaagaagta acaaaggaac    840

ctagaggcct tttgatgtta gcagaattgt catgcaaggg ctccctatct actggagaat    900

atactaaggg tactgttgac attgcgaaga gcgacaaaga ttttgttatc ggctttattg    960

ctcaaagaga catgggtgga agagatgaag gttacgattg gttgattatg acacccggtg   1020

tgggtttaga tgacaaggga gacgcattgg gtcaacagta tagaaccgtg gatgatgtgg   1080

tctctacagg atctgacatt attattgttg gaagaggact atttgcaaag ggaagggatg   1140

ctaaggtaga gggtgaacgt tacagaaaag caggctggga agcatatttg agaagatgcg   1200

gccagcaaaa ctaaaaaact gtattataag taaatgcatg tatactaaac tcacaaatta   1260
```

```
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc atttttaac caataggccg aaatcggcaa aatcccttat    1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcca ccgcggtggc ggccgctcta gaactagtgg atcccccggg   2040
ctgcaggaat tcgatatcaa gcttatcgat accgtcgacc tcgagggggg gcccggtacc   2100
cagcttttgt tccctttagt gagggttaat tccgagcttg gcgtaatcat ggtcatagct   2160
gtttcctgtg tgaaattgtt atccgctcac aattccacac aacataggag ccggaagcat   2220
aaagtgtaaa gcctggggtg cctaatgagt gaggtaactc acattaattg cgttgcgctc   2280
actgcccgct ttccagtcgg gaaacctgtc gtgccagctg cattaatgaa tcggccaacg   2340
cgcggggaga ggcggtttgc gtattgggcg ctcttccgct tcctcgctca ctgactcgct   2400
gcgctcggtc gttcggctgc ggcgagcggt atcagctcac tcaaaggcgg taatacggtt   2460
atccacagaa tcaggggata acgcaggaaa gaacatgtga gcaaaaggcc agcaaaaggc   2520
caggaaccgt aaaaaggccg cgttgctggc gtttttccat aggctcggcc cccctgacga   2580
gcatcacaaa aatcgacgct caagtcagag gtggcgaaac ccgacaggac tataaagata   2640
ccaggcgttc ccccctggaa gctccctcgt gcgctctcct gttccgaccc tgccgcttac   2700
cggatacctg tccgcctttc tcccttcggg aagcgtggcg ctttctcaat gctcacgctg   2760
taggtatctc agttcggtgt aggtcgttcg ctccaagctg ggctgtgtgc acgaaccccc   2820
cgttcagccc gaccgctgcg ccttatccgg taactatcgt cttgagtcca acccggtaag   2880
acacgactta tcgccactgg cagcagccac tggtaacagg attagcagag cgaggtatgt   2940
aggcggtgct acagagttct tgaagtggtg gcctaactac ggctacacta gaaggacagt   3000
atttggtatc tgcgctctgc tgaagccagt taccttcgga aaaagagttg gtagctcttg   3060
atccggcaaa caaaccaccg ctggtagcgg tggttttttt gtttgcaagc agcagattac   3120
gcgcagaaaa aaaggatctc aagaagatcc tttgatcttt tctacggggt ctgacgctca   3180
gtggaacgaa aactcacgtt aagggatttt ggtcatgaga ttatcaaaaa ggatcttcac   3240
ctagatcctt ttaaattaaa aatgaagttt taaatcaatc taaagtatat atgagtaaac   3300
ttggtctgac agttaccaat gcttaatcag tgaggcacct atctcagcga tctgtctatt   3360
tcgttcatcc atagttgcct gactgcccgt cgtgtagata actacgatac gggagggctt   3420
accatctggc cccagtgctg caatgatacc gcgagaccca cgctcaccgg ctccagattt   3480
atcagcaata aaccagccag ccggaagggc cgagcgcaga agtggtcctg caactttatc   3540
cgcctccatc cagtctatta attgttgccg ggaagctaga gtaagtagtt cgccagttaa   3600
```

```
tagtttgcgc aacgttgttg ccattgctac aggcatcgtg gtgtcacgct cgtcgtttgg   3660
tatggcttca ttcagctccg gttcccaacg atcaaggcga gttacatgat cccccatgtt   3720
gtgaaaaaaa gcggttagct ccttcggtcc tccgatcgtt gtcagaagta agttggccgc   3780
agtgttatca ctcatggtta tggcagcact gcataattct cttactgtca tgccatccgt   3840
aagatgcttt tctgtgactg gtgagtactc aaccaagtca ttctgagaat agtgtatgcg   3900
gcgaccgagt tgctcttgcc cggcgtcaat acgggataat accgcgccac atagcagaac   3960
tttaaaagtg ctcatcattg gaaaacgttc ttcggggcga aaactctcaa ggatcttacc   4020
gctgttgaga tccagttcga tgtaacccac tcgtgcaccc aactgatctt cagcatcttt   4080
tactttcacc agcgtttctg ggtgagcaaa aacaggaagg caaaatgccg caaaaaaggg   4140
aataagggcg acacggaaat gttgaatact catactcttc ctttttcaat attattgaag   4200
catttatcag ggttattgtc tcatgagcgg atacatattt gaatgtattt agaaaaataa   4260
acaaataggg gttccgcgca catttccccg aaaagtgcca cctgggtcct tttcatcacg   4320
tgctataaaa ataattataa tttaaatttt ttaatataaa tatataaatt aaaaatagaa   4380
agtaaaaaaa gaaattaaag aaaaaatagt ttttgttttc cgaagatgta aaagactcta   4440
gggggatcgc caacaaatac taccttttat cttgctcttc ctgctctcag gtattaatgc   4500
cgaattgttt catcttgtct gtgtagaaga ccacacacga aaatcctgtg attttacatt   4560
ttacttatcg ttaatcgaat gtatatctat ttaatctgct ttcttgtct aataaatata   4620
tatgtaaagt acgctttttg ttgaaatttt ttaaaccttt gtttattttt ttttcttcat   4680
tccgtaactc ttctaccttc tttatttact ttctaaaatc caaatacaaa acataaaaat   4740
aaataaacac agagtaaatt cccaaattat tccatcatta aaagatacga ggcgcgtgta   4800
agttacaggc aagcgatccg tcctaagaaa ccattattat catgacatta acctataaaa   4860
ataggcgtat cacgaggccc tttcgtc                                       4887
```

<210> SEQ ID NO 20
<211> LENGTH: 8597
<212> TYPE: DNA
<213> ORGANISM: Artificial Sequence
<220> FEATURE:
<223> OTHER INFORMATION: Plasmid pYRH43

<400> SEQUENCE: 20

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
```

```
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
```

```
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
```

-continued

```
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc ggggggcttg tctagggtat   6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atgtactcag actacaacat tcctggtgcc   7020
atgccggcgt ccatggccat gcctccgttc aaacaggagt ttgactacgc ccaatacgac   7080
cttaaccagc ccctgccccc gcagcagcaa caacagccta tcgacctgac ccctggaggg   7140
cccctccccg tctcggatta ctcgacgtcg tcatacaccc tggacaacga ctcacagaag   7200
cgaaaaatgt ccccgggaga gtccaccagt gacggaggcg ccgacgacga gtctccagaa   7260
ggagatgacg gtgaggccga ccccaagaag ccccgaaagc ccggccgaaa gcccgaaacc   7320
accatccccg cgtccaaacg caaggctcag aaccgggctg cccaaagggc cttcagagag   7380
cgaaaggaaa agcatctgcg cgacctggaa accaaaatat ctcagctcga gggcgagacg   7440
gcagccaaaa actcggaaaa cgagttcctg cgcttccagg tccagcggct tcagaacgag   7500
ctcaagcttt accgtgagaa gcctgccggc acttcgggag cctctggagt ctctggagcc   7560
ggagcacccg cttcaaacgt gcattcggct cccatcccgg agatgtcgtc caaaccgttc   7620
acgttcgagt tcccctcgta caacgtgccc aagccgaccg atgtggagcg agaggcacgc   7680
gagcaactgc aacgagagca gatccgaggc tacttgcagc gcaagccctc atctgtggcc   7740
tccgacacca cttctcctgc atctcaaacc tcgtgcaacc agtctccctg caccaacccc   7800
tcggcataca cttcgcccca gagccagagt ggaagtgtga gccagcagaa gcccctgttg   7860
```

```
ggtgctacca tcgctgccat gaacggcaag cccgaccccc atgctgttga cttttgtgct   7920

gagctctcca aggcctgtgt aaacaaggcc gagctgctgc agcgatccgc cacagccagt   7980

gcatctccca caacctccaa cacggtggta ccgtccgcag ctgcaccggg tagcactcag   8040

cagtcggcag gccagccctc tgtatccact cctacctcct ccacaactgc ccctcctcaa   8100

ttgtctgcat ctgtcgctac agccggctct gatcttcccg gatcggactt cctgtttgac   8160

atgcccttcg acatggactt tatgtcgtac cgagaccccg tttccgagac ggcacatctg   8220

gacgactttt cgctgcccga gctcacgaca gaaacatcca tgtttgatcc tctggacccc   8280

cattccagca gcgacgttat ttctggcaag cctctgtcta ccatgggcgc tacacacagt   8340

ggtgtcaaca acggacaggg aagtggtgct cccgaagtca agaaggagga ggatgaggac   8400

ctgctcatgt tctccaagcc caagacgctc atgaactgca ccgctgtgtg ggaccgtatc   8460

acgtcgcatc ccaagtttgg cgatatcgac atcgagggcc tgtgttcgga gctgcgaaac   8520

aaggcaaagt gcagtgagag tggcgtcgtg ttgacggagt tggacgtgga tggtgtcctg   8580

tcaacgttcc agtaagc                                                  8597
```

```
<210> SEQ ID NO 21
<211> LENGTH: 42
<212> TYPE: DNA
<213> ORGANISM: Artificial Sequence
<220> FEATURE:
<223> OTHER INFORMATION: primer Yap1-F

<400> SEQUENCE: 21

gatcaaacat gtactcagac tacaacattc ctggtgccat gc                        42


<210> SEQ ID NO 22
<211> LENGTH: 20
<212> TYPE: DNA
<213> ORGANISM: Artificial Sequence
<220> FEATURE:
<223> OTHER INFORMATION: Primer ef-324F

<400> SEQUENCE: 22

cgactgtgcc atcctcatca                                                 20


<210> SEQ ID NO 23
<211> LENGTH: 21
<212> TYPE: DNA
<213> ORGANISM: Artificial Sequence
<220> FEATURE:
<223> OTHER INFORMATION: Primer ef-392R

<400> SEQUENCE: 23

tgaccgtcct tggagatacc a                                               21


<210> SEQ ID NO 24
<211> LENGTH: 21
<212> TYPE: DNA
<213> ORGANISM: Artificial Sequence
<220> FEATURE:
<223> OTHER INFORMATION: Primer ef-345T

<400> SEQUENCE: 24

tgctggtggt gttggtgagt t                                               21


<210> SEQ ID NO 25
<211> LENGTH: 492
<212> TYPE: DNA
<213> ORGANISM: Saccharomyces cerevisiae
```

```
<220> FEATURE:
<221> NAME/KEY: CDS
<222> LOCATION: (1)..(492)
<223> OTHER INFORMATION: GenBank Accession No. NM_001179559

<400> SEQUENCE: 25

atg tca gaa ttc tat aag cta gca cct gtt gac aag aaa ggc caa cca       48
Met Ser Glu Phe Tyr Lys Leu Ala Pro Val Asp Lys Lys Gly Gln Pro
1               5                   10                  15

ttc ccc ttc gac caa tta aag gga aaa gtg gtg ctt atc gtt aat gtt       96
Phe Pro Phe Asp Gln Leu Lys Gly Lys Val Val Leu Ile Val Asn Val
            20                  25                  30

gcc tcc aaa tgt gga ttc act cct caa tac aaa gaa cta gag gcc ttg      144
Ala Ser Lys Cys Gly Phe Thr Pro Gln Tyr Lys Glu Leu Glu Ala Leu
        35                  40                  45

tac aaa cgt tat aag gac gaa gga ttt acc atc atc ggg ttc cca tgc      192
Tyr Lys Arg Tyr Lys Asp Glu Gly Phe Thr Ile Ile Gly Phe Pro Cys
    50                  55                  60

aac cag ttt ggc cac caa gaa cct ggc tct gat gaa gaa att gcc cag      240
Asn Gln Phe Gly His Gln Glu Pro Gly Ser Asp Glu Glu Ile Ala Gln
65                  70                  75                  80

ttc tgc caa ctg aac tat ggc gtg act ttc ccc att atg aaa aaa att      288
Phe Cys Gln Leu Asn Tyr Gly Val Thr Phe Pro Ile Met Lys Lys Ile
                85                  90                  95

gac gtt aat ggt ggc aat gag gac cct gtt tac aag ttt ttg aag agc      336
Asp Val Asn Gly Gly Asn Glu Asp Pro Val Tyr Lys Phe Leu Lys Ser
            100                 105                 110

caa aaa tcc ggt atg ttg ggc ttg aga ggt atc aaa tgg aat ttt gaa      384
Gln Lys Ser Gly Met Leu Gly Leu Arg Gly Ile Lys Trp Asn Phe Glu
        115                 120                 125

aaa ttc tta gtc gat aaa aag ggt aaa gtg tac gaa aga tac tct tca      432
Lys Phe Leu Val Asp Lys Lys Gly Lys Val Tyr Glu Arg Tyr Ser Ser
    130                 135                 140

cta acc aaa cct tct tcg ttg tcc gaa acc atc gaa gaa ctt ttg aaa      480
Leu Thr Lys Pro Ser Ser Leu Ser Glu Thr Ile Glu Glu Leu Leu Lys
145                 150                 155                 160

gag gtg gaa tag                                                      492
Glu Val Glu


<210> SEQ ID NO 26
<211> LENGTH: 163
<212> TYPE: PRT
<213> ORGANISM: Saccharomyces cerevisiae

<400> SEQUENCE: 26

Met Ser Glu Phe Tyr Lys Leu Ala Pro Val Asp Lys Lys Gly Gln Pro
1               5                   10                  15

Phe Pro Phe Asp Gln Leu Lys Gly Lys Val Val Leu Ile Val Asn Val
            20                  25                  30

Ala Ser Lys Cys Gly Phe Thr Pro Gln Tyr Lys Glu Leu Glu Ala Leu
        35                  40                  45

Tyr Lys Arg Tyr Lys Asp Glu Gly Phe Thr Ile Ile Gly Phe Pro Cys
    50                  55                  60

Asn Gln Phe Gly His Gln Glu Pro Gly Ser Asp Glu Glu Ile Ala Gln
65                  70                  75                  80

Phe Cys Gln Leu Asn Tyr Gly Val Thr Phe Pro Ile Met Lys Lys Ile
                85                  90                  95

Asp Val Asn Gly Gly Asn Glu Asp Pro Val Tyr Lys Phe Leu Lys Ser
            100                 105                 110
```

```
Gln Lys Ser Gly Met Leu Gly Leu Arg Gly Ile Lys Trp Asn Phe Glu
        115                 120                 125

Lys Phe Leu Val Asp Lys Lys Gly Lys Val Tyr Glu Arg Tyr Ser Ser
    130                 135                 140

Leu Thr Lys Pro Ser Ser Leu Ser Glu Thr Ile Glu Glu Leu Leu Lys
145                 150                 155                 160

Glu Val Glu


<210> SEQ ID NO 27
<211> LENGTH: 507
<212> TYPE: DNA
<213> ORGANISM: Yarrowia lipolytica
<220> FEATURE:
<221> NAME/KEY: CDS
<222> LOCATION: (1)..(507)
<223> OTHER INFORMATION: YALI0E02310; GenBank Accession No. XP_503454

<400> SEQUENCE: 27

atg tcc gcc gag aaa acc aat acc gct ttc tac aac ctc gct cca ctc       48
Met Ser Ala Glu Lys Thr Asn Thr Ala Phe Tyr Asn Leu Ala Pro Leu
1               5                   10                  15

gac aag aac gga gag cct ttc ccc ttc aag cag ctt gag ggc aag gtc       96
Asp Lys Asn Gly Glu Pro Phe Pro Phe Lys Gln Leu Glu Gly Lys Val
            20                  25                  30

gtg ctc atc gtg aac gtc gcc tcc aag tgt ggc ttt act ccc caa tac      144
Val Leu Ile Val Asn Val Ala Ser Lys Cys Gly Phe Thr Pro Gln Tyr
        35                  40                  45

aag ggc ctt gag gag gtc tac cag aag tac aag gat cag gga ttc acc      192
Lys Gly Leu Glu Glu Val Tyr Gln Lys Tyr Lys Asp Gln Gly Phe Thr
    50                  55                  60

atc atc ggc ttc ccc tgc aac cag ttt ggt ggc caa gag cct ggt tcc      240
Ile Ile Gly Phe Pro Cys Asn Gln Phe Gly Gly Gln Glu Pro Gly Ser
65                  70                  75                  80

gct gac gag atc tcc tcc ttc tgt cag ctg aac tac ggc gtc act ttc      288
Ala Asp Glu Ile Ser Ser Phe Cys Gln Leu Asn Tyr Gly Val Thr Phe
                85                  90                  95

ccc gtt ctt cag aag atc aac gtc aac ggc aac gac gcc gac ccc gtc      336
Pro Val Leu Gln Lys Ile Asn Val Asn Gly Asn Asp Ala Asp Pro Val
            100                 105                 110

tac gtc tac ctg aag gag cag aag gct ggt ctg ctg ggc ttc cga gga      384
Tyr Val Tyr Leu Lys Glu Gln Lys Ala Gly Leu Leu Gly Phe Arg Gly
        115                 120                 125

atc aag tgg aac ttt gag aag ttc ctg gtt gat aag cac ggt aac gtc      432
Ile Lys Trp Asn Phe Glu Lys Phe Leu Val Asp Lys His Gly Asn Val
    130                 135                 140

gtc gac cga tat gct tcc ctc aag acc ccc gcc ggc ctc gaa tcc acc      480
Val Asp Arg Tyr Ala Ser Leu Lys Thr Pro Ala Gly Leu Glu Ser Thr
145                 150                 155                 160

atc gag acc ctc ctc aaa aag ccc taa                                  507
Ile Glu Thr Leu Leu Lys Lys Pro
                165


<210> SEQ ID NO 28
<211> LENGTH: 168
<212> TYPE: PRT
<213> ORGANISM: Yarrowia lipolytica

<400> SEQUENCE: 28

Met Ser Ala Glu Lys Thr Asn Thr Ala Phe Tyr Asn Leu Ala Pro Leu
1               5                   10                  15

Asp Lys Asn Gly Glu Pro Phe Pro Phe Lys Gln Leu Glu Gly Lys Val
```

```
            20                  25                  30

Val Leu Ile Val Asn Val Ala Ser Lys Cys Gly Phe Thr Pro Gln Tyr
        35                  40                  45

Lys Gly Leu Glu Glu Val Tyr Gln Lys Tyr Lys Asp Gln Gly Phe Thr
    50                  55                  60

Ile Ile Gly Phe Pro Cys Asn Gln Phe Gly Gly Gln Glu Pro Gly Ser
65                  70                  75                  80

Ala Asp Glu Ile Ser Ser Phe Cys Gln Leu Asn Tyr Gly Val Thr Phe
                85                  90                  95

Pro Val Leu Gln Lys Ile Asn Val Asn Gly Asn Asp Ala Asp Pro Val
            100                 105                 110

Tyr Val Tyr Leu Lys Glu Gln Lys Ala Gly Leu Leu Gly Phe Arg Gly
        115                 120                 125

Ile Lys Trp Asn Phe Glu Lys Phe Leu Val Asp Lys His Gly Asn Val
    130                 135                 140

Val Asp Arg Tyr Ala Ser Leu Lys Thr Pro Ala Gly Leu Glu Ser Thr
145                 150                 155                 160

Ile Glu Thr Leu Leu Lys Lys Pro
                165
```

<210> SEQ ID NO 29
<211> LENGTH: 7651
<212> TYPE: DNA
<213> ORGANISM: Artificial Sequence
<220> FEATURE:
<223> OTHER INFORMATION: Plasmid pYRH65

<400> SEQUENCE: 29

```
ggccgcaagt gtggatgggg aagtgagtgc ccggttctgt gtgcacaatt ggcaatccaa     60

gatggatgga ttcaacacag ggatatagcg agctacgtgg tggtgcgagg atatagcaac    120

ggatatttat gtttgacact tgagaatgta cgatacaagc actgtccaag tacaatacta    180

aacatactgt acatactcat actcgtaccc gggcaacggt ttcacttgag tgcagtggct    240

agtgctctta ctcgtacagt gtgcaatact gcgtatcata gtctttgatg tatatcgtat    300

tcattcatgt tagttgcgta cgttgattga ggtggagcca gatgggctat tgtttcatat    360

atagactggc agccacctct ttggcccagc atgtttgtat acctggaagg gaaaactaaa    420

gaagctggct agtttagttt gattattata gtagatgtcc taatcactag agattagaat    480

gtcttggcga tgattagtcg tcgtcccctg tatcatgtct agaccaactg tgtcatgaag    540

ttggtgctgg tgttttacct gtgtactaca agtaggtgtc ctagatctag tgtacagagc    600

cgtttagacc catgtggact tcaccattaa cgatggaaaa tgttcattat atgacagtat    660

attacaatgg acttgctcca tttcttcctt gcatcacatg ttctccacct ccatagttga    720

tcaacacatc atagtagcta aggctgctgc tctcccacta cagtccacca caagttaagt    780

agcaccgtca gtacagctaa aagtacacgt ctagtacgtt tcataactag tcaagtagcc    840

cctattacag atatcagcac tatcacgcac gagtttttct ctgtgctatc taatcaactt    900

gccaagtatt cggagaagat acactttctt ggcatcaggt atacgaggga gcctatcaga    960

tgaaaaaggg tatattggat ccattcatat ccacctacac gttgtcataa tctcctcatt   1020

cacgtgattc atttcgtgac actagtttct cactttcccc cccgcaccta tagtcaactt   1080

ggcggacacg ctacttgtag ctgacgttga tttatagacc caatcaaagc gggttatcgg   1140

tcaggtagca cttatcattc atcgttcata ctacgatgag caatctcggg catgtccgga   1200
```

-continued

```
aaagtgtcgg gcgcgccagc tgcattaatg aatcggccaa cgcgcgggga gaggcggttt   1260
gcgtattggg cgctcttccg cttcctcgct cactgactcg ctgcgctcgg tcgttcggct   1320
gcggcgagcg gtatcagctc actcaaaggc ggtaatacgg ttatccacag aatcagggga   1380
taacgcagga aagaacatgt gagcaaaagg ccagcaaaag gccaggaacc gtaaaaaggc   1440
cgcgttgctg gcgtttttcc ataggctccg cccccctgac gagcatcaca aaaatcgacg   1500
ctcaagtcag aggtggcgaa acccgacagg actataaaga taccaggcgt ttccccctgg   1560
aagctccctc gtgcgctctc ctgttccgac cctgccgctt accggatacc tgtccgcctt   1620
tctcccttcg ggaagcgtgg cgctttctca tagctcacgc tgtaggtatc tcagttcggt   1680
gtaggtcgtt cgctccaagc tgggctgtgt gcacgaaccc cccgttcagc ccgaccgctg   1740
cgccttatcc ggtaactatc gtcttgagtc caacccggta agacacgact tatcgccact   1800
ggcagcagcc actggtaaca ggattagcag agcgaggtat gtaggcggtg ctacagagtt   1860
cttgaagtgg tggcctaact acggctacac tagaagaaca gtatttggta tctgcgctct   1920
gctgaagcca gttaccttcg gaaaaagagt tggtagctct tgatccggca aacaaaccac   1980
cgctggtagc ggtggttttt ttgtttgcaa gcagcagatt acgcgcagaa aaaaaggatc   2040
tcaagaagat cctttgatct tttctacggg gtctgacgct cagtggaacg aaaactcacg   2100
ttaagggatt ttggtcatga gattatcaaa aaggatcttc acctagatcc ttttaaatta   2160
aaaatgaagt tttaaatcaa tctaaagtat atatgagtaa acttggtctg acagttacca   2220
atgcttaatc agtgaggcac ctatctcagc gatctgtcta tttcgttcat ccatagttgc   2280
ctgactcccc gtcgtgtaga taactacgat acgggagggc ttaccatctg gccccagtgc   2340
tgcaatgata ccgcgagacc cacgctcacc ggctccagat ttatcagcaa taaaccagcc   2400
agccggaagg gccgagcgca gaagtggtcc tgcaacttta tccgcctcca tccagtctat   2460
taattgttgc cgggaagcta gagtaagtag ttcgccagtt aatagtttgc gcaacgttgt   2520
tgccattgct acaggcatcg tggtgtcacg ctcgtcgttt ggtatggctt cattcagctc   2580
cggttcccaa cgatcaaggc gagttacatg atcccccatg ttgtgcaaaa aagcggttag   2640
ctccttcggt cctccgatcg ttgtcagaag taagttggcc gcagtgttat cactcatggt   2700
tatggcagca ctgcataatt ctcttactgt catgccatcc gtaagatgct tttctgtgac   2760
tggtgagtac tcaaccaagt cattctgaga atagtgtatg cggcgaccga gttgctcttg   2820
cccggcgtca atacgggata ataccgcgcc acatagcaga actttaaaag tgctcatcat   2880
tggaaaacgt tcttcggggc gaaaactctc aaggatctta ccgctgttga gatccagttc   2940
gatgtaaccc actcgtgcac ccaactgatc ttcagcatct tttactttca ccagcgtttc   3000
tgggtgagca aaaacaggaa ggcaaaatgc cgcaaaaaag ggaataaggg cgacacggaa   3060
atgttgaata ctcatactct tcctttttca atattattga agcatttatc agggttattg   3120
tctcatgagc ggatacatat ttgaatgtat ttagaaaaat aaacaaatag gggttccgcg   3180
cacatttccc cgaaaagtgc cacctgatgc ggtgtgaaat accgcacaga tgcgtaagga   3240
gaaaataccg catcaggaaa ttgtaagcgt taatattttg ttaaaattcg cgttaaattt   3300
ttgttaaatc agctcatttt ttaaccaata ggccgaaatc ggcaaaatcc cttataaatc   3360
aaaagaatag accgagatag ggttgagtgt tgttccagtt tggaacaaga gtccactatt   3420
aaagaacgtg gactccaacg tcaaagggcg aaaaaccgtc tatcagggcg atggcccact   3480
acgtgaacca tcaccctaat caagtttttt ggggtcgagg tgccgtaaag cactaaatcg   3540
gaaccctaaa gggagccccc gatttagagc ttgacgggga aagccggcga acgtggcgag   3600
```

```
aaaggaaggg aagaaagcga aaggagcggg cgctagggcg ctggcaagtg tagcggtcac   3660
gctgcgcgta accaccacac ccgccgcgct taatgcgccg ctacagggcg cgtccattcg   3720
ccattcaggc tgcgcaactg ttgggaaggg cgatcggtgc gggcctcttc gctattacgc   3780
cagctggcga aaggggggatg tgctgcaagg cgattaagtt gggtaacgcc agggttttcc   3840
cagtcacgac gttgtaaaac gacggccagt gaattgtaat acgactcact atagggcgaa   3900
ttgggcccga cgtcgcatgc attccgacag cagcgactgg gcaccatgat caagcgaaac   3960
accttccccc agctgccctg gcaaaccatc aagaacccta ctttcatcaa gtgcaagaac   4020
ggttctactc ttctcacctc cggtgtctac ggctggtgcc gaaagcctaa ctacaccgct   4080
gatttcatca tgtgcctcac ctgggctctc atgtgcggtg ttgcttctcc cctgccttac   4140
ttctacccgg tcttcttctt cctggtgctc atccaccgag cttaccgaga ctttgagcga   4200
ctggagcgaa agtacggtga ggactaccag gagttcaagc gacaggtccc ttggatcttc   4260
atcccttatg ttttctaaac gataagctta gtgagcgaat ggtgaggtta cttaattgag   4320
tggccagcct atgggattgt ataacagaca gtcaatatat tactgaaaag actgaacagc   4380
cagacggagt gaggttgtga gtgaatcgta gagggcggct attacagcaa gtctactcta   4440
cagtgtacta acacagcaga gaacaaatac aggtgtgcat tcggctatct gagaattagt   4500
tggagagctc gagaccctcg gcgataaact gctcctcggt tttgtgtcca tacttgtacg   4560
gaccattgta atggggcaag tcgttgagtt ctcgtcgtcc gacgttcaga gcacagaaac   4620
caatgtaatc aatgtagcag agatggttct gcaaaagatt gatttgtgcg agcaggttaa   4680
ttaagtcata cacaagtcag ctttcttcga gcctcatata agtataagta gttcaacgta   4740
ttagcactgt acccagcatc tccgtatcga gaaacacaac aacatgcccc attggacaga   4800
tcatgcggat acacaggttg tgcagtatca tacatactcg atcagacagg tcgtctgacc   4860
atcatacaag ctgaacaagc gctccatact tgcacgctct ctatatacac agttaaatta   4920
catatccata gtctaacctc taacagttaa tcttctggta agcctcccag ccagccttct   4980
ggtatcgctt ggcctcctca ataggatctc ggttctggcc gtacagacct cggccgacaa   5040
ttatgatatc cgttccggta gacatgacat cctcaacagt tcggtactgc tgtccgagag   5100
cgtctccctt gtcgtcaaga cccaccccgg gggtcagaat aagccagtcc tcagagtcgc   5160
ccttaggtcg gttctgggca atgaagccaa ccacaaactc ggggtcggat cgggcaagct   5220
caatggtctg cttggagtac tcgccagtgg ccagagagcc cttgcaagac agctcggcca   5280
gcatgagcag acctctggcc agcttctcgt tgggagaggg gactaggaac tccttgtact   5340
gggagttctc gtagtcagag acgtcctcct tcttctgttc agagacagtt tcctcggcac   5400
cagctcgcag gccagcaatg attccggttc cgggtacacc gtgggcgttg gtgatatcgg   5460
accactcggc gattcggtga caccggtact ggtgcttgac agtgttgcca atatctgcga   5520
actttctgtc ctcgaacagg aagaaaccgt gcttaagagc aagttccttg agggggagca   5580
cagtgccggc gtaggtgaag tcgtcaatga tgtcgatatg ggttttgatc atgcacacat   5640
aaggtccgac cttatcggca agctcaatga gctccttggt ggtggtaaca tccagagaag   5700
cacacaggtt ggttttcttg gctgccacga gcttgagcac tcgagcggca aaggcggact   5760
tgtggacgtt agctcgagct tcgtaggagg gcattttggt ggtgaagagg agactgaaat   5820
aaatttagtc tgcagaactt tttatcggaa ccttatctgg ggcagtgaag tatatgttat   5880
ggtaatagtt acgagttagt tgaacttata gatagactgg actatacggc tatcggtcca   5940
```

```
aattagaaag aacgtcaatg gctctctggg cgtcgccttt gccgacaaaa atgtgatcat   6000

gatgaaagcc agcaatgacg ttgcagctga tattgttgtc ggccaaccgc gccgaaaacg   6060

cagctgtcag acccacagcc tccaacgaag aatgtatcgt caaagtgatc caagcacact   6120

catagttgga gtcgtactcc aaaggcggca atgacgagtc agacagatac tcgtcgacgt   6180

ttaaacagtg tacgcagatc tactatagag gaacatttaa attgccccgg agaagacggc   6240

caggccgcct agatgacaaa ttcaacaact cacagctgac tttctgccat tgccactagg   6300

ggggggcctt tttatatggc caagccaagc tctccacgtc ggttgggctg cacccaacaa   6360

taaatgggta gggttgcacc aacaaaggga tgggatgggg ggtagaagat acgaggataa   6420

cggggctcaa tggcacaaat aagaacgaat actgccatta agactcgtga tccagcgact   6480

gacaccattg catcatctaa gggcctcaaa actacctcgg aactgctgcg ctgatctgga   6540

caccacagag gttccgagca ctttaggttg caccaaatgt cccaccaggt gcaggcagaa   6600

aacgctggaa cagcgtgtac agtttgtctt aacaaaaagt gagggcgctg aggtcgagca   6660

gggtggtgtg acttgttata gcctttagag ctgcgaaagc gcgtatggat ttggctcatc   6720

aggccagatt gagggtctgt ggacacatgt catgttagtg tacttcaatc gccccctgga   6780

tatagccccg acaataggcc gtggcctcat ttttttgcct tccgcacatt tccattgctc   6840

gatacccaca ccttgcttct cctgcacttg ccaaccttaa tactggttta cattgaccaa   6900

catcttacaa gcggggggct tgtctagggt atatataaac agtggctctc ccaatcggtt   6960

gccagtctct tttttccttt ctttccccac agattcgaaa tctaaactac acatcacaga   7020

attccgagcc gtgagtatcc acgacaagat cagtgtcgag acgacgcgtt ttgtgtaatg   7080

acacaatccg aaagtcgcta gcaacacaca ctctctacac aaactaaccc agctctggta   7140

ccatggccgc cgagaaaacc aataccgctt tctacaacct cgctccactc gacaagaacg   7200

gagagccttt ccccttcaag cagcttgagg gcaaggtcgt gctcatcgtg aacgtcgcct   7260

ccaagtgtgg ctttactccc caatacaagg gccttgagga ggtctaccag aagtacaagg   7320

atcagggatt caccatcatc ggcttcccct gcaaccagtt tggtggccaa gagcctggtt   7380

ccgctgacga gatctcctcc ttctgtcagc tgaactacgg cgtcactttc cccgttcttc   7440

agaagatcaa cgtcaacggc aacgacgccg accccgtcta cgtctacctg aaggagcaga   7500

aggctggtct gctgggcttc cgaggaatca agtggaactt tgagaagttc ctggttgata   7560

agcacggtaa cgtcgtcgac cgatatgctt ccctcaagac ccccgccggc ctcgaatcca   7620

ccatcgagac cctcctcaaa aagccctaag c                                  7651
```

<210> SEQ ID NO 30
<211> LENGTH: 44
<212> TYPE: DNA
<213> ORGANISM: Artificial Sequence
<220> FEATURE:
<223> OTHER INFORMATION: primer GPX3-F

<400> SEQUENCE: 30

```
gatcaaccat ggccgccgag aaaaccaata ccgctttcta caac                      44
```

<210> SEQ ID NO 31
<211> LENGTH: 45
<212> TYPE: DNA
<213> ORGANISM: Artificial Sequence
<220> FEATURE:
<223> OTHER INFORMATION: primer GPX3-R

<400> SEQUENCE: 31

```
gatcaagcgg ccgcttaggg ctttttgagg agggtctcga tggtg                   45


<210> SEQ ID NO 32
<211> LENGTH: 1164
<212> TYPE: DNA
<213> ORGANISM: Yarrowia lipolytica

<400> SEQUENCE: 32

taaagtagag agcatcccaa acaagcagtc gcagtcgcac tcatcgatat gcatatgtgc     60

tacttaactg tacgagtact gtacagtaca tacagtacct gtagtgattc acattcagtc    120

atacagtgca ggagtacttc cgcttgtctc acaggctttg tccatgtgcc aatgagtcag    180

acagacactt gtgcatgagg cagagcacac acatggcttc gttcaatctg ctgataggtc    240

gacattctgg gatctgctca ggttgttcag atgaccacct tctttttcac cccctctccc    300

tgtaccacca ggaccgtttc cgagacccac gtgaccctca aaccgtcgct cttgactttc    360

cccaggctct ccacctttgc cggctcaaag ctcggcgtct gtttatccct gtatccaatt    420

ttgcccacgc tggcatagag cagaatctcc acctgtctct ccacgacgtt tcttgacttg    480

ccaaacttga ctgattcaga gtagaccccc tgggaggaat gggaagagtt tgcggagtta    540

ccgaacagcg aagagaaggt gcctccatgg gtttccatct gccaaacgac gacacgtgtt    600

tctccgtcga aatcgggccc agggacgcta ttagacccta ttcccgtgag tccagcaacc    660

atttttccat ccggagaaaa gaccaggccc cacaccggag cagcatgatt ggaattgaat    720

tcctgggggt caagataggc atactctgag ccgattctca agtcgtagac aatcagagaa    780

caggtgtcgg tgaccttaat atccaggtct ctgttgagtt cagacagaga agatcttcgt    840

cgagacacat tcttttcaat catcacagca gtggcagtag gataaatagc cacagccaga    900

cgttgactgg gcttatggaa cgtgacaatg tacggaaatg tctgtgtgat ttgagacagt    960

agagctgtga ccttggactg cagagaaacg cctctctgga gggtcgagtg acgcagcaag   1020

tccggattca gcattttgca agcagtgtgc atcacaaacg gcacaaacat gtccatggag   1080

gaggattttc gggtgtggct gaagaagctg gaaagcacat cgatagctgt gattcgcaca   1140

actaacggct tgtcgaggtg catg                                          1164


<210> SEQ ID NO 33
<211> LENGTH: 591
<212> TYPE: DNA
<213> ORGANISM: Saccharomyces cerevisiae
<220> FEATURE:
<221> NAME/KEY: CDS
<222> LOCATION: (1)..(591)
<223> OTHER INFORMATION: GenBank Accession No. NM_001182386.1

<400> SEQUENCE: 33

atg gtc gct caa gtt caa aag caa gct cca act ttt aag aaa act gcc       48
Met Val Ala Gln Val Gln Lys Gln Ala Pro Thr Phe Lys Lys Thr Ala
1               5                   10                  15

gtc gtc gac ggt gtc ttt gac gaa gtc tcc ttg gac aaa tac aag ggt       96
Val Val Asp Gly Val Phe Asp Glu Val Ser Leu Asp Lys Tyr Lys Gly
            20                  25                  30

aag tac gtt gtc cta gcc ttt att cca ttg gcc ttc act ttc gtc tgt      144
Lys Tyr Val Val Leu Ala Phe Ile Pro Leu Ala Phe Thr Phe Val Cys
        35                  40                  45

cca acc gaa atc att gct ttc tca gaa gct gct aag aaa ttc gaa gaa      192
Pro Thr Glu Ile Ile Ala Phe Ser Glu Ala Ala Lys Lys Phe Glu Glu
    50                  55                  60
```

```
caa ggc gct caa gtt ctt ttc gcc tcc act gac tcc gaa tac tcc ctt      240
Gln Gly Ala Gln Val Leu Phe Ala Ser Thr Asp Ser Glu Tyr Ser Leu
65                  70                  75                  80

ttg gca tgg acc aat atc cca aga aag gaa ggt ggt ttg ggc cca atc      288
Leu Ala Trp Thr Asn Ile Pro Arg Lys Glu Gly Gly Leu Gly Pro Ile
                85                  90                  95

aac att cca ttg ttg gct gac acc aac cac tct ttg tcc aga gac tat      336
Asn Ile Pro Leu Leu Ala Asp Thr Asn His Ser Leu Ser Arg Asp Tyr
            100                 105                 110

ggt gtc ttg atc gaa gaa gaa ggt gtc gcc ttg aga ggt ttg ttc atc      384
Gly Val Leu Ile Glu Glu Glu Gly Val Ala Leu Arg Gly Leu Phe Ile
        115                 120                 125

atc gac cca aag ggt gtc att aga cac atc acc att aac gat ttg cca      432
Ile Asp Pro Lys Gly Val Ile Arg His Ile Thr Ile Asn Asp Leu Pro
    130                 135                 140

gtc ggt aga aac gtt gac gaa gcc ttg aga ttg gtt gaa gcc ttc caa      480
Val Gly Arg Asn Val Asp Glu Ala Leu Arg Leu Val Glu Ala Phe Gln
145                 150                 155                 160

tgg acc gac aag aac ggt act gtc ttg cca tgt aac tgg act cca ggt      528
Trp Thr Asp Lys Asn Gly Thr Val Leu Pro Cys Asn Trp Thr Pro Gly
                165                 170                 175

gct gct acc atc aag cca acc gtt gaa gac tcc aag gaa tac ttc gaa      576
Ala Ala Thr Ile Lys Pro Thr Val Glu Asp Ser Lys Glu Tyr Phe Glu
            180                 185                 190

gct gcc aac aaa taa                                                  591
Ala Ala Asn Lys
        195


<210> SEQ ID NO 34
<211> LENGTH: 196
<212> TYPE: PRT
<213> ORGANISM: Saccharomyces cerevisiae

<400> SEQUENCE: 34

Met Val Ala Gln Val Gln Lys Gln Ala Pro Thr Phe Lys Lys Thr Ala
1               5                   10                  15

Val Val Asp Gly Val Phe Asp Glu Val Ser Leu Asp Lys Tyr Lys Gly
            20                  25                  30

Lys Tyr Val Val Leu Ala Phe Ile Pro Leu Ala Phe Thr Phe Val Cys
        35                  40                  45

Pro Thr Glu Ile Ile Ala Phe Ser Glu Ala Ala Lys Lys Phe Glu Glu
    50                  55                  60

Gln Gly Ala Gln Val Leu Phe Ala Ser Thr Asp Ser Glu Tyr Ser Leu
65                  70                  75                  80

Leu Ala Trp Thr Asn Ile Pro Arg Lys Glu Gly Gly Leu Gly Pro Ile
                85                  90                  95

Asn Ile Pro Leu Leu Ala Asp Thr Asn His Ser Leu Ser Arg Asp Tyr
            100                 105                 110

Gly Val Leu Ile Glu Glu Glu Gly Val Ala Leu Arg Gly Leu Phe Ile
        115                 120                 125

Ile Asp Pro Lys Gly Val Ile Arg His Ile Thr Ile Asn Asp Leu Pro
    130                 135                 140

Val Gly Arg Asn Val Asp Glu Ala Leu Arg Leu Val Glu Ala Phe Gln
145                 150                 155                 160

Trp Thr Asp Lys Asn Gly Thr Val Leu Pro Cys Asn Trp Thr Pro Gly
                165                 170                 175

Ala Ala Thr Ile Lys Pro Thr Val Glu Asp Ser Lys Glu Tyr Phe Glu
            180                 185                 190
```

```
Ala Ala Asn Lys
        195


<210> SEQ ID NO 35
<211> LENGTH: 591
<212> TYPE: DNA
<213> ORGANISM: Yarrowia lipolytica
<220> FEATURE:
<221> NAME/KEY: CDS
<222> LOCATION: (1)..(591)
<223> OTHER INFORMATION: YALI0B15125; GenBank Accession No. XM_500915

<400> SEQUENCE: 35

atg gtc gcc act gtt cag cat ccc gcc ccc gac ttc aag aag act gcc       48
Met Val Ala Thr Val Gln His Pro Ala Pro Asp Phe Lys Lys Thr Ala
1               5                   10                  15

gtc tct ggt ggt gtc ttc gag gag gtc tcc ctc gac cag ttc aag ggt       96
Val Ser Gly Gly Val Phe Glu Glu Val Ser Leu Asp Gln Phe Lys Gly
            20                  25                  30

aag tgg gtt gtc ctc gcc ttc atc ccc ctg gct ttc acc ttc gtc tgc      144
Lys Trp Val Val Leu Ala Phe Ile Pro Leu Ala Phe Thr Phe Val Cys
        35                  40                  45

ccc acc gag atc atc gct tac tcc gat gcc gtc tct cag ttc aag gag      192
Pro Thr Glu Ile Ile Ala Tyr Ser Asp Ala Val Ser Gln Phe Lys Glu
    50                  55                  60

cga ggc gcc gag gtt ctc ttt gcc tcc acc gac tcc gag tac tct ctg      240
Arg Gly Ala Glu Val Leu Phe Ala Ser Thr Asp Ser Glu Tyr Ser Leu
65                  70                  75                  80

ctt gcc tgg acc aac gtt gcc cga aag gat ggt ggt ctt ggt ccc gtc      288
Leu Ala Trp Thr Asn Val Ala Arg Lys Asp Gly Gly Leu Gly Pro Val
                85                  90                  95

aac atc ccc ctg ctt gct gac acc aac cac acc ctg tcc aag gac tac      336
Asn Ile Pro Leu Leu Ala Asp Thr Asn His Thr Leu Ser Lys Asp Tyr
            100                 105                 110

ggt gtt ctc atc ccc gag gcc ggt gtc gct ctc cga ggt atc ttc atc      384
Gly Val Leu Ile Pro Glu Ala Gly Val Ala Leu Arg Gly Ile Phe Ile
        115                 120                 125

att gac ccc aag ggc gtt gtc cga cag atc acc atc aac gat ctc ccc      432
Ile Asp Pro Lys Gly Val Val Arg Gln Ile Thr Ile Asn Asp Leu Pro
    130                 135                 140

gtt ggc cga tcc gtc gag gag acc ctc cga ctc atc gat gcc ttc cag      480
Val Gly Arg Ser Val Glu Glu Thr Leu Arg Leu Ile Asp Ala Phe Gln
145                 150                 155                 160

ttc act gag aag cac ggt gag gtc tgc ccc gcc aac tgg cag aag ggc      528
Phe Thr Glu Lys His Gly Glu Val Cys Pro Ala Asn Trp Gln Lys Gly
                165                 170                 175

tcc gat act atc aag gct gac cct gtc aac gcc aag gag tac ttc gag      576
Ser Asp Thr Ile Lys Ala Asp Pro Val Asn Ala Lys Glu Tyr Phe Glu
            180                 185                 190

aag gcc aac aaa taa                                                  591
Lys Ala Asn Lys
        195


<210> SEQ ID NO 36
<211> LENGTH: 196
<212> TYPE: PRT
<213> ORGANISM: Yarrowia lipolytica

<400> SEQUENCE: 36

Met Val Ala Thr Val Gln His Pro Ala Pro Asp Phe Lys Lys Thr Ala
1               5                   10                  15
```

```
Val Ser Gly Gly Val Phe Glu Glu Val Ser Leu Asp Gln Phe Lys Gly
            20                  25                  30

Lys Trp Val Val Leu Ala Phe Ile Pro Leu Ala Phe Thr Phe Val Cys
        35                  40                  45

Pro Thr Glu Ile Ile Ala Tyr Ser Asp Ala Val Ser Gln Phe Lys Glu
    50                  55                  60

Arg Gly Ala Glu Val Leu Phe Ala Ser Thr Asp Ser Glu Tyr Ser Leu
65                  70                  75                  80

Leu Ala Trp Thr Asn Val Ala Arg Lys Asp Gly Gly Leu Gly Pro Val
                85                  90                  95

Asn Ile Pro Leu Leu Ala Asp Thr Asn His Thr Leu Ser Lys Asp Tyr
            100                 105                 110

Gly Val Leu Ile Pro Glu Ala Gly Val Ala Leu Arg Gly Ile Phe Ile
        115                 120                 125

Ile Asp Pro Lys Gly Val Val Arg Gln Ile Thr Ile Asn Asp Leu Pro
    130                 135                 140

Val Gly Arg Ser Val Glu Glu Thr Leu Arg Leu Ile Asp Ala Phe Gln
145                 150                 155                 160

Phe Thr Glu Lys His Gly Glu Val Cys Pro Ala Asn Trp Gln Lys Gly
                165                 170                 175

Ser Asp Thr Ile Lys Ala Asp Pro Val Asn Ala Lys Glu Tyr Phe Glu
            180                 185                 190

Lys Ala Asn Lys
        195


<210> SEQ ID NO 37
<211> LENGTH: 2025
<212> TYPE: DNA
<213> ORGANISM: Saccharomyces cerevisiae
<220> FEATURE:
<221> NAME/KEY: CDS
<222> LOCATION: (1)..(2025)
<223> OTHER INFORMATION: GenBank Accession No. NM_001178564.1

<400> SEQUENCE: 37

atg gaa cca att gat gac ata ctt ttt gag gtt act gat gcg ttc aaa      48
Met Glu Pro Ile Asp Asp Ile Leu Phe Glu Val Thr Asp Ala Phe Lys
1               5                   10                  15

act cag aag gag gat ctt ctt gag ttg gta aca ttg att gat ata tat      96
Thr Gln Lys Glu Asp Leu Leu Glu Leu Val Thr Leu Ile Asp Ile Tyr
            20                  25                  30

ggc gag caa gtt aac caa gag ggg agc tat gaa gaa aag acg aga ttc     144
Gly Glu Gln Val Asn Gln Glu Gly Ser Tyr Glu Glu Lys Thr Arg Phe
        35                  40                  45

att gaa act ttg aat aca ttg tta gag gat aat ccg agt act act ggt     192
Ile Glu Thr Leu Asn Thr Leu Leu Glu Asp Asn Pro Ser Thr Thr Gly
    50                  55                  60

gaa atc ggt tgg gat ctg cct aag gga tta ttg aag ttc ttg tca aag     240
Glu Ile Gly Trp Asp Leu Pro Lys Gly Leu Leu Lys Phe Leu Ser Lys
65                  70                  75                  80

gat aat gtc gat gta aat gga aga cta ggt acg aat atg att gtc caa     288
Asp Asn Val Asp Val Asn Gly Arg Leu Gly Thr Asn Met Ile Val Gln
                85                  90                  95

ggt gta atg aag tgt ttc tat gcc atc tca atc caa ggc gag ccc aaa     336
Gly Val Met Lys Cys Phe Tyr Ala Ile Ser Ile Gln Gly Glu Pro Lys
            100                 105                 110

aaa tgt tta att act ggg ttg gag ttg ctt tca tcc ctt tgt tca aaa     384
Lys Cys Leu Ile Thr Gly Leu Glu Leu Leu Ser Ser Leu Cys Ser Lys
        115                 120                 125
```

```
gat ttt tcc aag agt gat caa cag aat aag gaa gac ttt gtt gat aaa      432
Asp Phe Ser Lys Ser Asp Gln Gln Asn Lys Glu Asp Phe Val Asp Lys
    130                 135                 140

aag gcc aat acg tta cct cct gaa gga gta atc gaa aat tcc tct aat      480
Lys Ala Asn Thr Leu Pro Pro Glu Gly Val Ile Glu Asn Ser Ser Asn
145                 150                 155                 160

cga aaa gat ttt cca tcc tac ggt gaa agc aag agt tca aat gaa ttt      528
Arg Lys Asp Phe Pro Ser Tyr Gly Glu Ser Lys Ser Ser Asn Glu Phe
                165                 170                 175

ttc ttg aag ttg aaa tcc tac att tta ttt gaa ttc ata ggg gcg agt      576
Phe Leu Lys Leu Lys Ser Tyr Ile Leu Phe Glu Phe Ile Gly Ala Ser
            180                 185                 190

ctg aaa agg att tct act ctg ttt cct tcg aaa tat ctg gga gct gct      624
Leu Lys Arg Ile Ser Thr Leu Phe Pro Ser Lys Tyr Leu Gly Ala Ala
        195                 200                 205

gtg tca aca att gag aaa ttt gtg tat agt cat gcg gac act ttt gaa      672
Val Ser Thr Ile Glu Lys Phe Val Tyr Ser His Ala Asp Thr Phe Glu
    210                 215                 220

gat gcc ctt ttc ctt ctt cgt agg gtg tac aca ttc tgc agg aac tat      720
Asp Ala Leu Phe Leu Leu Arg Arg Val Tyr Thr Phe Cys Arg Asn Tyr
225                 230                 235                 240

att ccc cct gat cca cca aaa gat ata caa ttg aac gaa gat ttt act      768
Ile Pro Pro Asp Pro Pro Lys Asp Ile Gln Leu Asn Glu Asp Phe Thr
                245                 250                 255

cga gag atg ttt gat aaa gtt gtg gag gaa gaa agt gaa tta cag gtt      816
Arg Glu Met Phe Asp Lys Val Val Glu Glu Glu Ser Glu Leu Gln Val
            260                 265                 270

aga cta ttg cgt agg ctt tgt act ttt ggt att tcg aca ccc ata aaa      864
Arg Leu Leu Arg Arg Leu Cys Thr Phe Gly Ile Ser Thr Pro Ile Lys
        275                 280                 285

act gtc acc acc aat gcc gac gtg aaa tac tat tgt gca cta aat caa      912
Thr Val Thr Thr Asn Ala Asp Val Lys Tyr Tyr Cys Ala Leu Asn Gln
    290                 295                 300

cag aag ttt gaa tta tct gca tat tac acc gaa tat ctt gag cta ttt      960
Gln Lys Phe Glu Leu Ser Ala Tyr Tyr Thr Glu Tyr Leu Glu Leu Phe
305                 310                 315                 320

tgc agg tat tac caa atg gcg ttc tcg ctt gat gtt gat ata gag gga     1008
Cys Arg Tyr Tyr Gln Met Ala Phe Ser Leu Asp Val Asp Ile Glu Gly
                325                 330                 335

gaa ttt cag aat gtg ata aaa gaa tgt agg att att tat aag tct gta     1056
Glu Phe Gln Asn Val Ile Lys Glu Cys Arg Ile Ile Tyr Lys Ser Val
            340                 345                 350

ccc cag gag att tcc gct gtt aat gat gaa gca aag ttg gtt ttg gaa     1104
Pro Gln Glu Ile Ser Ala Val Asn Asp Glu Ala Lys Leu Val Leu Glu
        355                 360                 365

aga atg gta tat aaa ttg gct tat aca ttc gaa gta caa aag gcc gct     1152
Arg Met Val Tyr Lys Leu Ala Tyr Thr Phe Glu Val Gln Lys Ala Ala
    370                 375                 380

aaa gaa aaa aat gtt ggt ttg gac tat aat ggt gta ata tta ttt tct     1200
Lys Glu Lys Asn Val Gly Leu Asp Tyr Asn Gly Val Ile Leu Phe Ser
385                 390                 395                 400

ggt atc cac tat ttg gaa acc aat caa cat tta gta aag gaa atg aat     1248
Gly Ile His Tyr Leu Glu Thr Asn Gln His Leu Val Lys Glu Met Asn
                405                 410                 415

ata acg gat gcc att tat ctc tac ttg aga ttt aca act cca tca tta     1296
Ile Thr Asp Ala Ile Tyr Leu Tyr Leu Arg Phe Thr Thr Pro Ser Leu
            420                 425                 430

tat tct aaa gtt tac tat aat gta gca gtt gaa tca gtt agt cgc tac     1344
Tyr Ser Lys Val Tyr Tyr Asn Val Ala Val Glu Ser Val Ser Arg Tyr
```

```
        435                 440                 445

tgg cta tgg tat gct att aca acc gag ccc ttg gag gat gta aaa aaa      1392
Trp Leu Trp Tyr Ala Ile Thr Thr Glu Pro Leu Glu Asp Val Lys Lys
    450                 455                 460

gaa ttg aag aat ctt tca gtg ttt gtt aca aaa aca tta ttg cat gtt      1440
Glu Leu Lys Asn Leu Ser Val Phe Val Thr Lys Thr Leu Leu His Val
465                 470                 475                 480

cta ctt caa aag aac tgt att cag gtc aat cag cag tta aga atg ata      1488
Leu Leu Gln Lys Asn Cys Ile Gln Val Asn Gln Gln Leu Arg Met Ile
                485                 490                 495

act ttc act ctt ctc acc aga tta cta tgt tta ata cct gaa aaa gtt      1536
Thr Phe Thr Leu Leu Thr Arg Leu Leu Cys Leu Ile Pro Glu Lys Val
            500                 505                 510

gca ttt gag ttt atc tta gat gtg ctt aag aca tct ccc ctt cca ttg      1584
Ala Phe Glu Phe Ile Leu Asp Val Leu Lys Thr Ser Pro Leu Pro Leu
        515                 520                 525

gct aag acg tcc gta tta tgt gtt ttt aaa gac ctt tca agg cga cgc      1632
Ala Lys Thr Ser Val Leu Cys Val Phe Lys Asp Leu Ser Arg Arg Arg
    530                 535                 540

atc tcc acc aag gat aac gat tct gag acg gat ttg att gtc gaa aaa      1680
Ile Ser Thr Lys Asp Asn Asp Ser Glu Thr Asp Leu Ile Val Glu Lys
545                 550                 555                 560

tta tcc aaa ctg aag gtc aat gat agt aac aaa gct cag caa agt aac      1728
Leu Ser Lys Leu Lys Val Asn Asp Ser Asn Lys Ala Gln Gln Ser Asn
                565                 570                 575

atc aga cat tat atc caa cta gat tct tcc aaa atg aaa gct gtt cat      1776
Ile Arg His Tyr Ile Gln Leu Asp Ser Ser Lys Met Lys Ala Val His
            580                 585                 590

gac tgt tgt ctg cag act atc caa gat tca ttt acg gca gat gcc aag      1824
Asp Cys Cys Leu Gln Thr Ile Gln Asp Ser Phe Thr Ala Asp Ala Lys
        595                 600                 605

aag agt gat ata tta tta ctg cta act tac ttg aat att ttc att gtg      1872
Lys Ser Asp Ile Leu Leu Leu Leu Thr Tyr Leu Asn Ile Phe Ile Val
    610                 615                 620

cta aaa aaa aca tgg gat gaa gat cta ctg aag att gtt tgt tcg aag      1920
Leu Lys Lys Thr Trp Asp Glu Asp Leu Leu Lys Ile Val Cys Ser Lys
625                 630                 635                 640

att gat tct aat ttg aag tca gtc gaa cct gat aaa ctt ccg aag tat      1968
Ile Asp Ser Asn Leu Lys Ser Val Glu Pro Asp Lys Leu Pro Lys Tyr
                645                 650                 655

aag gaa att gtg gat aaa aac gaa tct cta aat gac tat ttt act ggt      2016
Lys Glu Ile Val Asp Lys Asn Glu Ser Leu Asn Asp Tyr Phe Thr Gly
            660                 665                 670

ata aaa tga                                                          2025
Ile Lys


<210> SEQ ID NO 38
<211> LENGTH: 674
<212> TYPE: PRT
<213> ORGANISM: Saccharomyces cerevisiae

<400> SEQUENCE: 38

Met Glu Pro Ile Asp Asp Ile Leu Phe Glu Val Thr Asp Ala Phe Lys
1               5                   10                  15

Thr Gln Lys Glu Asp Leu Leu Glu Leu Val Thr Leu Ile Asp Ile Tyr
            20                  25                  30

Gly Glu Gln Val Asn Gln Glu Gly Ser Tyr Glu Glu Lys Thr Arg Phe
        35                  40                  45

Ile Glu Thr Leu Asn Thr Leu Leu Glu Asp Asn Pro Ser Thr Thr Gly
```

```
    50                  55                  60

Glu Ile Gly Trp Asp Leu Pro Lys Gly Leu Leu Lys Phe Leu Ser Lys
65                  70                  75                  80

Asp Asn Val Asp Val Asn Gly Arg Leu Gly Thr Asn Met Ile Val Gln
                85                  90                  95

Gly Val Met Lys Cys Phe Tyr Ala Ile Ser Ile Gln Gly Glu Pro Lys
            100                 105                 110

Lys Cys Leu Ile Thr Gly Leu Glu Leu Leu Ser Ser Leu Cys Ser Lys
        115                 120                 125

Asp Phe Ser Lys Ser Asp Gln Gln Asn Lys Glu Asp Phe Val Asp Lys
    130                 135                 140

Lys Ala Asn Thr Leu Pro Pro Glu Gly Val Ile Glu Asn Ser Ser Asn
145                 150                 155                 160

Arg Lys Asp Phe Pro Ser Tyr Gly Glu Ser Lys Ser Ser Asn Glu Phe
                165                 170                 175

Phe Leu Lys Leu Lys Ser Tyr Ile Leu Phe Glu Phe Ile Gly Ala Ser
            180                 185                 190

Leu Lys Arg Ile Ser Thr Leu Phe Pro Ser Lys Tyr Leu Gly Ala Ala
        195                 200                 205

Val Ser Thr Ile Glu Lys Phe Val Tyr Ser His Ala Asp Thr Phe Glu
    210                 215                 220

Asp Ala Leu Phe Leu Leu Arg Arg Val Tyr Thr Phe Cys Arg Asn Tyr
225                 230                 235                 240

Ile Pro Pro Asp Pro Pro Lys Asp Ile Gln Leu Asn Glu Asp Phe Thr
                245                 250                 255

Arg Glu Met Phe Asp Lys Val Val Glu Glu Glu Ser Glu Leu Gln Val
            260                 265                 270

Arg Leu Leu Arg Arg Leu Cys Thr Phe Gly Ile Ser Thr Pro Ile Lys
        275                 280                 285

Thr Val Thr Thr Asn Ala Asp Val Lys Tyr Tyr Cys Ala Leu Asn Gln
    290                 295                 300

Gln Lys Phe Glu Leu Ser Ala Tyr Tyr Thr Glu Tyr Leu Glu Leu Phe
305                 310                 315                 320

Cys Arg Tyr Tyr Gln Met Ala Phe Ser Leu Asp Val Asp Ile Glu Gly
                325                 330                 335

Glu Phe Gln Asn Val Ile Lys Glu Cys Arg Ile Ile Tyr Lys Ser Val
            340                 345                 350

Pro Gln Glu Ile Ser Ala Val Asn Asp Glu Ala Lys Leu Val Leu Glu
        355                 360                 365

Arg Met Val Tyr Lys Leu Ala Tyr Thr Phe Glu Val Gln Lys Ala Ala
    370                 375                 380

Lys Glu Lys Asn Val Gly Leu Asp Tyr Asn Gly Val Ile Leu Phe Ser
385                 390                 395                 400

Gly Ile His Tyr Leu Glu Thr Asn Gln His Leu Val Lys Glu Met Asn
                405                 410                 415

Ile Thr Asp Ala Ile Tyr Leu Tyr Leu Arg Phe Thr Thr Pro Ser Leu
            420                 425                 430

Tyr Ser Lys Val Tyr Tyr Asn Val Ala Val Glu Ser Val Ser Arg Tyr
        435                 440                 445

Trp Leu Trp Tyr Ala Ile Thr Thr Glu Pro Leu Glu Asp Val Lys Lys
    450                 455                 460

Glu Leu Lys Asn Leu Ser Val Phe Val Thr Lys Thr Leu Leu His Val
465                 470                 475                 480
```

```
Leu Leu Gln Lys Asn Cys Ile Gln Val Asn Gln Gln Leu Arg Met Ile
                485                 490                 495

Thr Phe Thr Leu Leu Thr Arg Leu Leu Cys Leu Ile Pro Glu Lys Val
            500                 505                 510

Ala Phe Glu Phe Ile Leu Asp Val Leu Lys Thr Ser Pro Leu Pro Leu
        515                 520                 525

Ala Lys Thr Ser Val Leu Cys Val Phe Lys Asp Leu Ser Arg Arg Arg
    530                 535                 540

Ile Ser Thr Lys Asp Asn Asp Ser Glu Thr Asp Leu Ile Val Glu Lys
545                 550                 555                 560

Leu Ser Lys Leu Lys Val Asn Asp Ser Asn Lys Ala Gln Gln Ser Asn
                565                 570                 575

Ile Arg His Tyr Ile Gln Leu Asp Ser Ser Lys Met Lys Ala Val His
            580                 585                 590

Asp Cys Cys Leu Gln Thr Ile Gln Asp Ser Phe Thr Ala Asp Ala Lys
        595                 600                 605

Lys Ser Asp Ile Leu Leu Leu Leu Thr Tyr Leu Asn Ile Phe Ile Val
    610                 615                 620

Leu Lys Lys Thr Trp Asp Glu Asp Leu Leu Lys Ile Val Cys Ser Lys
625                 630                 635                 640

Ile Asp Ser Asn Leu Lys Ser Val Glu Pro Asp Lys Leu Pro Lys Tyr
                645                 650                 655

Lys Glu Ile Val Asp Lys Asn Glu Ser Leu Asn Asp Tyr Phe Thr Gly
            660                 665                 670

Ile Lys


<210> SEQ ID NO 39
<211> LENGTH: 2025
<212> TYPE: DNA
<213> ORGANISM: Yarrowia lipolytica
<220> FEATURE:
<221> NAME/KEY: CDS
<222> LOCATION: (1)..(2025)
<223> OTHER INFORMATION: YALI0B03762; GenBank Accession No. XM_500469

<400> SEQUENCE: 39

atg caa cta acc gac gac cat aag aaa gac ctg gaa aag ctg ggc gag       48
Met Gln Leu Thr Asp Asp His Lys Lys Asp Leu Glu Lys Leu Gly Glu
1               5                   10                  15

gaa ttg aag ggc aag gag gag cac acg gtg gct ggg gag gat gag gaa       96
Glu Leu Lys Gly Lys Glu Glu His Thr Val Ala Gly Glu Asp Glu Glu
            20                  25                  30

gat gtc aac cat ggc gcc gac gat tcc gaa gac gcc gaa gac gaa gac      144
Asp Val Asn His Gly Ala Asp Asp Ser Glu Asp Ala Glu Asp Glu Asp
        35                  40                  45

gcc gaa gac gag aac gac tac acc gaa ctg gat gtg gac att gtg tgc      192
Ala Glu Asp Glu Asn Asp Tyr Thr Glu Leu Asp Val Asp Ile Val Cys
    50                  55                  60

caa ttc atc aag gac gcc gcc aga gag gcc gag aag acg ggc gac tac      240
Gln Phe Ile Lys Asp Ala Ala Arg Glu Ala Glu Lys Thr Gly Asp Tyr
65                  70                  75                  80

att tcc tac gca acc gtc atc gac atc cac tgc tcg gat cca tcc aga      288
Ile Ser Tyr Ala Thr Val Ile Asp Ile His Cys Ser Asp Pro Ser Arg
                85                  90                  95

tac aag cac gta gac agg gtc aag atc ctc acg tct ctt ctg gag gtg      336
Tyr Lys His Val Asp Arg Val Lys Ile Leu Thr Ser Leu Leu Glu Val
            100                 105                 110
```

```
ctg cgg acc aac ccc aag att tgc gag gaa att ggc tgg gat ctt cca      384
Leu Arg Thr Asn Pro Lys Ile Cys Glu Glu Ile Gly Trp Asp Leu Pro
        115                 120                 125

gcg ctt ttg ctg ccc tac ttc aat gtc gag gac ttt gat ttc aac gac      432
Ala Leu Leu Leu Pro Tyr Phe Asn Val Glu Asp Phe Asp Phe Asn Asp
    130                 135                 140

ggt ctc gag ggt cac ccg acc ttc tac cct ctg att atg ctg ttc tcg      480
Gly Leu Glu Gly His Pro Thr Phe Tyr Pro Leu Ile Met Leu Phe Ser
145                 150                 155                 160

acc ctg gca gag tac ggc aac ccc aag gag ctg ttt ctc aag acc gtc      528
Thr Leu Ala Glu Tyr Gly Asn Pro Lys Glu Leu Phe Leu Lys Thr Val
                165                 170                 175

gag acg ctc agt aca ctg acc tgt gac cgc gca ccc gaa aat gac aaa      576
Glu Thr Leu Ser Thr Leu Thr Cys Asp Arg Ala Pro Glu Asn Asp Lys
            180                 185                 190

ctc aag ttc aaa cag gcc gaa tct cta cgg aaa ttc gag gtc tgc aag      624
Leu Lys Phe Lys Gln Ala Glu Ser Leu Arg Lys Phe Glu Val Cys Lys
        195                 200                 205

ttc cac gtt ctc gag gaa ctc atg agc tcg tgc atg aag aaa atc aag      672
Phe His Val Leu Glu Glu Leu Met Ser Ser Cys Met Lys Lys Ile Lys
    210                 215                 220

acc cag tac ccc tcc cgg ttc ttg gct tcc gct gct tcc gcc att ctc      720
Thr Gln Tyr Pro Ser Arg Phe Leu Ala Ser Ala Ala Ser Ala Ile Leu
225                 230                 235                 240

atg ttc tcc gct cga aat gcg gca ctt ttc aga cac ttc cct ctc att      768
Met Phe Ser Ala Arg Asn Ala Ala Leu Phe Arg His Phe Pro Leu Ile
                245                 250                 255

gtc ggc att ctg gct aga aga gtc tac gta ttt att cga gac tgg ggg      816
Val Gly Ile Leu Ala Arg Arg Val Tyr Val Phe Ile Arg Asp Trp Gly
            260                 265                 270

atg gac gga gac gaa ccc atg gac atg tcg cct gac gaa caa gcc aag      864
Met Asp Gly Asp Glu Pro Met Asp Met Ser Pro Asp Glu Gln Ala Lys
        275                 280                 285

agc gcc aag att cta cag tcc ctg tcc acg tac ttt ttt tac tcg tgg      912
Ser Ala Lys Ile Leu Gln Ser Leu Ser Thr Tyr Phe Phe Tyr Ser Trp
    290                 295                 300

ttc cac cgg gtg gct gtc cga tgg agt agc aat ctc ttc cga gag atc      960
Phe His Arg Val Ala Val Arg Trp Ser Ser Asn Leu Phe Arg Glu Ile
305                 310                 315                 320

aaa cac tca atc cac gag ttg ccc aga gcc gaa aga gcc aag tac gac     1008
Lys His Ser Ile His Glu Leu Pro Arg Ala Glu Arg Ala Lys Tyr Asp
                325                 330                 335

aac ccg aaa tca aat gga tcg gcc gtt tac acc att tac aac cga tgg     1056
Asn Pro Lys Ser Asn Gly Ser Ala Val Tyr Thr Ile Tyr Asn Arg Trp
            340                 345                 350

ggc act ctg gcg cta tct ctg gat ctt gat ccc agt caa tat ttc ctt     1104
Gly Thr Leu Ala Leu Ser Leu Asp Leu Asp Pro Ser Gln Tyr Phe Leu
        355                 360                 365

cct ctg atc cag gag atc cag gag gac gtc cag gag gcc acc aag gga     1152
Pro Leu Ile Gln Glu Ile Gln Glu Asp Val Gln Glu Ala Thr Lys Gly
    370                 375                 380

ggg ttg gac gat act ctt gcg gga ttc agc aag agt tca ctt tca gac     1200
Gly Leu Asp Asp Thr Leu Ala Gly Phe Ser Lys Ser Ser Leu Ser Asp
385                 390                 395                 400

gcc tcc ccc atc gca ttt gtt gac tac agc atg tac gat gac gcc tct     1248
Ala Ser Pro Ile Ala Phe Val Asp Tyr Ser Met Tyr Asp Asp Ala Ser
                405                 410                 415

gag att cct ctg tct cag gag ggt ctg ctt atg ctt gct acc cag tac     1296
Glu Ile Pro Leu Ser Gln Glu Gly Leu Leu Met Leu Ala Thr Gln Tyr
            420                 425                 430
```

```
atg atg gag aac cgc gac cac agt ctc aat att tct cta gat cag ctg      1344
Met Met Glu Asn Arg Asp His Ser Leu Asn Ile Ser Leu Asp Gln Leu
        435                 440                 445

gtt tct ctg aca cta tat ctt gtg cac aga tcc tcc cct aag gaa cct      1392
Val Ser Leu Thr Leu Tyr Leu Val His Arg Ser Ser Pro Lys Glu Pro
    450                 455                 460

ctt cct ttt gcc att aca gac ttg ctc ctg ttc tgg gga tgg tgg act      1440
Leu Pro Phe Ala Ile Thr Asp Leu Leu Leu Phe Trp Gly Trp Trp Thr
465                 470                 475                 480

ctc aaa gac atg gag cgt ccc gag gtg cga caa ctt gat gaa gca ttt      1488
Leu Lys Asp Met Glu Arg Pro Glu Val Arg Gln Leu Asp Glu Ala Phe
                485                 490                 495

tac gtc aag tat ctg cag ttc ctg gtg ttt att tcg gca tct tct ccc      1536
Tyr Val Lys Tyr Leu Gln Phe Leu Val Phe Ile Ser Ala Ser Ser Pro
            500                 505                 510

ttg ccc gaa atc aga aac att gcc tac aca ctc tgt ggg cgg ctg ttg      1584
Leu Pro Glu Ile Arg Asn Ile Ala Tyr Thr Leu Cys Gly Arg Leu Leu
        515                 520                 525

tac ctg cag cac gag tct gtc tcg ttc gcc ttc atc gca gac act att      1632
Tyr Leu Gln His Glu Ser Val Ser Phe Ala Phe Ile Ala Asp Thr Ile
    530                 535                 540

gcg gat tgt ccg ttt gag aat gcc cag gta gcc atg gta ggt att ctc      1680
Ala Asp Cys Pro Phe Glu Asn Ala Gln Val Ala Met Val Gly Ile Leu
545                 550                 555                 560

aag cgt ctg atg atc cct gac gag atc tcc gac cag ctc tca aaa ctc      1728
Lys Arg Leu Met Ile Pro Asp Glu Ile Ser Asp Gln Leu Ser Lys Leu
                565                 570                 575

aga att ccc gat gtg ccg acc cga gag gga gtc gaa cac cag aag gcc      1776
Arg Ile Pro Asp Val Pro Thr Arg Glu Gly Val Glu His Gln Lys Ala
            580                 585                 590

tcc cag acc acc atc ccg aca act ccc gag cat gtg gat act atc aag      1824
Ser Gln Thr Thr Ile Pro Thr Thr Pro Glu His Val Asp Thr Ile Lys
        595                 600                 605

agt ctt tgt aac gct gca ttg gaa cag gag aac acg cac ctg gtg atc      1872
Ser Leu Cys Asn Ala Ala Leu Glu Gln Glu Asn Thr His Leu Val Ile
    610                 615                 620

acc tgg ctc aac ttc ctg tcc aca gtg aag ctg gac tgc ggt ttc gcg      1920
Thr Trp Leu Asn Phe Leu Ser Thr Val Lys Leu Asp Cys Gly Phe Ala
625                 630                 635                 640

ggt gac tat gct gag cgg gtg gag aag gtg att gac gag gtg gag gat      1968
Gly Asp Tyr Ala Glu Arg Val Glu Lys Val Ile Asp Glu Val Glu Asp
                645                 650                 655

gag aac gac cgg act ctg att aga ctg gct ctg gac gtg ttg gca aag      2016
Glu Asn Asp Arg Thr Leu Ile Arg Leu Ala Leu Asp Val Leu Ala Lys
            660                 665                 670

acc gtc tag                                                          2025
Thr Val

<210> SEQ ID NO 40
<211> LENGTH: 674
<212> TYPE: PRT
<213> ORGANISM: Yarrowia lipolytica

<400> SEQUENCE: 40

Met Gln Leu Thr Asp Asp His Lys Lys Asp Leu Glu Lys Leu Gly Glu
1               5                   10                  15

Glu Leu Lys Gly Lys Glu Glu His Thr Val Ala Gly Glu Asp Glu Glu
            20                  25                  30

Asp Val Asn His Gly Ala Asp Asp Ser Glu Asp Ala Glu Asp Glu Asp
```

```
        35                  40                  45

Ala Glu Asp Glu Asn Asp Tyr Thr Glu Leu Asp Val Asp Ile Val Cys
    50                  55                  60

Gln Phe Ile Lys Asp Ala Ala Arg Glu Ala Glu Lys Thr Gly Asp Tyr
65                  70                  75                  80

Ile Ser Tyr Ala Thr Val Ile Asp Ile His Cys Ser Asp Pro Ser Arg
                85                  90                  95

Tyr Lys His Val Asp Arg Val Lys Ile Leu Thr Ser Leu Leu Glu Val
            100                 105                 110

Leu Arg Thr Asn Pro Lys Ile Cys Glu Glu Ile Gly Trp Asp Leu Pro
        115                 120                 125

Ala Leu Leu Leu Pro Tyr Phe Asn Val Glu Asp Phe Asp Phe Asn Asp
    130                 135                 140

Gly Leu Glu Gly His Pro Thr Phe Tyr Pro Leu Ile Met Leu Phe Ser
145                 150                 155                 160

Thr Leu Ala Glu Tyr Gly Asn Pro Lys Glu Leu Phe Leu Lys Thr Val
                165                 170                 175

Glu Thr Leu Ser Thr Leu Thr Cys Asp Arg Ala Pro Glu Asn Asp Lys
            180                 185                 190

Leu Lys Phe Lys Gln Ala Glu Ser Leu Arg Lys Phe Glu Val Cys Lys
        195                 200                 205

Phe His Val Leu Glu Glu Leu Met Ser Ser Cys Met Lys Lys Ile Lys
    210                 215                 220

Thr Gln Tyr Pro Ser Arg Phe Leu Ala Ser Ala Ala Ser Ala Ile Leu
225                 230                 235                 240

Met Phe Ser Ala Arg Asn Ala Ala Leu Phe Arg His Phe Pro Leu Ile
                245                 250                 255

Val Gly Ile Leu Ala Arg Arg Val Tyr Val Phe Ile Arg Asp Trp Gly
            260                 265                 270

Met Asp Gly Asp Glu Pro Met Asp Met Ser Pro Asp Glu Gln Ala Lys
        275                 280                 285

Ser Ala Lys Ile Leu Gln Ser Leu Ser Thr Tyr Phe Phe Tyr Ser Trp
    290                 295                 300

Phe His Arg Val Ala Val Arg Trp Ser Ser Asn Leu Phe Arg Glu Ile
305                 310                 315                 320

Lys His Ser Ile His Glu Leu Pro Arg Ala Glu Arg Ala Lys Tyr Asp
                325                 330                 335

Asn Pro Lys Ser Asn Gly Ser Ala Val Tyr Thr Ile Tyr Asn Arg Trp
            340                 345                 350

Gly Thr Leu Ala Leu Ser Leu Asp Leu Asp Pro Ser Gln Tyr Phe Leu
        355                 360                 365

Pro Leu Ile Gln Glu Ile Gln Glu Asp Val Gln Glu Ala Thr Lys Gly
    370                 375                 380

Gly Leu Asp Asp Thr Leu Ala Gly Phe Ser Lys Ser Ser Leu Ser Asp
385                 390                 395                 400

Ala Ser Pro Ile Ala Phe Val Asp Tyr Ser Met Tyr Asp Asp Ala Ser
                405                 410                 415

Glu Ile Pro Leu Ser Gln Glu Gly Leu Leu Met Leu Ala Thr Gln Tyr
            420                 425                 430

Met Met Glu Asn Arg Asp His Ser Leu Asn Ile Ser Leu Asp Gln Leu
        435                 440                 445

Val Ser Leu Thr Leu Tyr Leu Val His Arg Ser Ser Pro Lys Glu Pro
    450                 455                 460
```

Leu Pro Phe Ala Ile Thr Asp Leu Leu Leu Phe Trp Gly Trp Trp Thr
465 470 475 480

Leu Lys Asp Met Glu Arg Pro Glu Val Arg Gln Leu Asp Glu Ala Phe
485 490 495

Tyr Val Lys Tyr Leu Gln Phe Leu Val Phe Ile Ser Ala Ser Ser Pro
500 505 510

Leu Pro Glu Ile Arg Asn Ile Ala Tyr Thr Leu Cys Gly Arg Leu Leu
515 520 525

Tyr Leu Gln His Glu Ser Val Ser Phe Ala Phe Ile Ala Asp Thr Ile
530 535 540

Ala Asp Cys Pro Phe Glu Asn Ala Gln Val Ala Met Val Gly Ile Leu
545 550 555 560

Lys Arg Leu Met Ile Pro Asp Glu Ile Ser Asp Gln Leu Ser Lys Leu
565 570 575

Arg Ile Pro Asp Val Pro Thr Arg Glu Gly Val Glu His Gln Lys Ala
580 585 590

Ser Gln Thr Thr Ile Pro Thr Thr Pro Glu His Val Asp Thr Ile Lys
595 600 605

Ser Leu Cys Asn Ala Ala Leu Glu Gln Glu Asn Thr His Leu Val Ile
610 615 620

Thr Trp Leu Asn Phe Leu Ser Thr Val Lys Leu Asp Cys Gly Phe Ala
625 630 635 640

Gly Asp Tyr Ala Glu Arg Val Glu Lys Val Ile Asp Glu Val Glu Asp
645 650 655

Glu Asn Asp Arg Thr Leu Ile Arg Leu Ala Leu Asp Val Leu Ala Lys
660 665 670

Thr Val

<210> SEQ ID NO 41
<211> LENGTH: 4
<212> TYPE: PRT
<213> ORGANISM: Artificial Sequence
<220> FEATURE:
<223> OTHER INFORMATION: HPGS motif

<400> SEQUENCE: 41

His Pro Gly Ser
1

<210> SEQ ID NO 42
<211> LENGTH: 4
<212> TYPE: PRT
<213> ORGANISM: Artificial Sequence
<220> FEATURE:
<223> OTHER INFORMATION: HAGG motif

<400> SEQUENCE: 42

His Ala Gly Gly
1

<210> SEQ ID NO 43
<211> LENGTH: 655
<212> TYPE: PRT
<213> ORGANISM: Candida glabrata

<400> SEQUENCE: 43

Met Ser Asp Ala Phe Glu Glu Val Cys Asp Ala Leu Lys Ala Ser Phe
1 5 10 15

```
Thr Asp Asp Lys Glu Asp Ser Leu Thr Leu Val Thr Met Ile Asp Thr
            20                  25                  30

Leu Ser Glu Glu Val Asp Glu Gly Phe Glu Val Lys Glu Lys Glu Gln
        35                  40                  45

Phe Leu Glu Leu Leu Leu Asn Leu Leu Glu Ala Asp Thr Glu Leu Val
    50                  55                  60

Ser Ala Val Gly Trp Asp Leu Pro Arg Thr Leu Leu Arg Phe Cys Asn
65                  70                  75                  80

Ala Lys Asn Ile Lys Asn Ser Asp Arg Leu Arg Lys Cys Lys Val Val
                85                  90                  95

Thr Ile Cys Met Ala Ile Phe Asn Leu Leu Ala Leu His Ala Lys Pro
            100                 105                 110

Gln Glu Cys Leu Val Thr Thr Leu Glu Leu Leu Ser Glu Leu Asn Phe
        115                 120                 125

Lys Asn Ile Val Glu Glu Cys His Gln Leu Ser Glu Asp Gly Ser Asp
    130                 135                 140

Asn Asn Thr Ala Glu Glu Asp Asn Asp Ala Val Glu Asp Tyr Met Lys
145                 150                 155                 160

Asp Arg Asp Gln Pro Glu Ile Ile Phe Gly Val Lys Ser Tyr Ala Leu
                165                 170                 175

Phe Glu Leu Ala Gly Ser Leu Ile Arg Arg Val Ala Thr Leu His Pro
            180                 185                 190

Ser Lys Tyr Leu Glu Glu Ala Val Thr Ala Ile Arg Lys Tyr Val Thr
        195                 200                 205

Asn Asn Thr Glu Val Val Glu Asp Val Lys Phe Ile Leu Arg Arg Val
    210                 215                 220

Phe Ala Phe Cys Arg Gly Tyr Ile Pro Pro Glu Pro Pro Arg Gln Leu
225                 230                 235                 240

Ile Val Asp Leu Lys Met Asn His Glu Glu Tyr Asp Glu Ile Met Asn
                245                 250                 255

Ser Glu Ile Glu Leu Gln Val Arg Leu Leu Arg Asn Leu Cys Thr Phe
            260                 265                 270

Ser Val Ala Tyr Cys Val Lys Phe Leu Asn Asp Lys Thr Glu Val Val
        275                 280                 285

Tyr Phe His Lys Leu Ile Asn Lys Asp Leu Gln Leu Pro Glu Phe Tyr
    290                 295                 300

Arg Ser Val His Asp Ile Ile Ser Arg Tyr Tyr Gln Ile Ala Phe Ser
305                 310                 315                 320

Phe Asp Ile Asp Leu Asn Asp Glu Phe Asn Asp Ile Leu Arg Glu Thr
                325                 330                 335

Arg Gly Ile Tyr Glu Asp Val Ile Lys Arg Ile Asn Glu Thr Asn Asn
            340                 345                 350

Thr Asp Lys Asn Ala Lys Ser Asp Ile Leu Leu Lys Ala Gly Tyr Tyr
        355                 360                 365

Tyr Glu Val Gln Lys Thr Ala Arg Glu Lys Glu Ile Asn Pro Asp Thr
    370                 375                 380

Lys Gly Ile Ile Leu Leu Ser Gly Phe Asn Tyr Ile Glu Asn Gly Asp
385                 390                 395                 400

His Leu Ile Asp Ile Asp Ile Ala Asp Ala Leu Tyr Leu Tyr Leu Arg
                405                 410                 415

Phe Ala Ser Glu Ser Leu Phe Ser Pro Thr Cys His Asn Val Thr Ile
            420                 425                 430

Glu Gly Val Ala Arg Tyr Trp Ile Trp Ala Ala Leu Thr Thr Thr Asp
```

```
        435                 440                 445

Asn Asn Ile Leu Lys Glu Lys Leu Ala Glu Leu Ser Pro Leu Val Leu
    450                 455                 460

His Ser Val Leu Asn Leu Leu Leu Val Lys Asn Cys His Gln Val Asn
465                 470                 475                 480

Glu Glu Ile Arg Met Ile Thr Phe Thr Leu Ile Thr Arg Ile Leu Cys
                485                 490                 495

Leu Leu Pro Glu Asn Cys Ser Tyr Glu Phe Leu Met Asp Glu Leu Asp
            500                 505                 510

Asn Cys Ala Val Val Phe Gly Lys Ser Cys Val Leu Gly Ile Leu Arg
        515                 520                 525

Asp Leu Val Ile Lys Val Asp His Ser Val Ser Ser Asn Asn Thr Asp
    530                 535                 540

Thr Glu Asp Leu Ser Glu Ser Met Ala Gln Leu Lys Ile Asn Asn Glu
545                 550                 555                 560

Lys Arg Ala Lys Lys Thr Phe Ile Thr Leu Asp Pro Lys Arg Ala Gly
                565                 570                 575

Glu Ile Glu Asp Leu Ala Ile Lys Thr Leu Lys Glu Thr Lys Lys Ser
            580                 585                 590

Met Lys Lys Asp Tyr Ile Leu Leu Val Leu Asn Tyr Ile Lys Phe Phe
        595                 600                 605

Ser Thr Phe Ala His Lys Trp Asn Lys Ser Lys Leu Asn Glu Phe Thr
    610                 615                 620

Thr Leu Val Ala Thr Asn Phe Ser Asp Ser Lys Met Leu Pro Glu Ile
625                 630                 635                 640

Asn Ala Ile Ile Asp Ala Asn Glu Lys Leu Arg Ser Leu Thr Glu
                645                 650                 655


<210> SEQ ID NO 44
<211> LENGTH: 702
<212> TYPE: PRT
<213> ORGANISM: Kluyveromyces lactis

<400> SEQUENCE: 44

Met Pro Leu Glu Val Glu Arg Phe Lys Glu Ile Glu Glu Lys Leu Leu
1               5                   10                  15

Thr Ala Phe Val Glu Glu Lys Ser Asp Ile Ile Thr Leu Val Thr Ile
            20                  25                  30

Leu Asp Leu Tyr Ser Glu Glu Val Asn Phe Lys Gly Ser Leu Glu Gln
        35                  40                  45

Lys Tyr Glu Tyr Leu Ser Glu Val Leu Ser Leu Leu Gln Gln Asn Lys
    50                  55                  60

Asp Val Val Tyr Glu Ile Gly Trp Asp Leu Pro Lys Ile Leu Ile Lys
65                  70                  75                  80

Phe Ile His Trp Gly Asn Asn Asn His Leu Gly Ala Asp Arg Ser Lys
                85                  90                  95

Lys Phe Leu Thr Val Ile Met Lys Cys Phe Asn Glu Val Ala Leu Phe
            100                 105                 110

Gly Asn Pro Lys Glu Cys Phe Phe Ala Gly Cys Glu Leu Met Ser Ser
        115                 120                 125

Leu Arg Ile Asn Asp Glu Ser Leu Val Arg Phe Ile Val Glu Glu Glu
    130                 135                 140

Pro Val Met Asp Pro Glu Asn Glu Asp Ser Gly Asp Glu Thr Tyr Thr
145                 150                 155                 160
```

```
Glu Asp Glu Gly Ser Ser Asp Lys Thr Glu Glu Glu Glu Glu Lys Asn
                165                 170                 175

Ala Val Lys Asp Ser Pro Thr Pro Lys Ser Ala Asn Glu Ser Ile Pro
            180                 185                 190

Asp Leu Lys Glu Gly Tyr Ala Phe Tyr Gly Arg Leu Pro Gln Glu Val
        195                 200                 205

Ile Thr Glu Leu Arg Phe Tyr Ser Ile Ile Glu Leu Met Gly Ser Thr
    210                 215                 220

Leu Lys Arg Ile Val Thr Leu His Pro Ser Lys Phe Leu Ser Glu Ala
225                 230                 235                 240

Val Glu Ala Phe Ser Arg Phe Asn Leu Gln Asn Asn Glu Asp Val Asp
                245                 250                 255

Asp Cys Leu Phe Ile Leu Arg Arg Leu Tyr Ser Phe Ile Arg Gly Tyr
            260                 265                 270

Ile Pro Pro Ser Pro Pro Pro Asp Ala Asp Lys Gln Val Ser Ala Glu
        275                 280                 285

Glu Leu Glu Glu Ile Lys Val Ser Glu Glu Val Leu Gln Arg Lys Leu
    290                 295                 300

Leu Cys Asn Ile Leu Thr Ser Ala Leu His Gln Leu Leu Lys Ala Arg
305                 310                 315                 320

Thr Cys Ile Ser Leu Leu Asn Tyr His Ser His Leu Gln Gly Ile Pro
                325                 330                 335

Thr Leu Ser Thr Ser Ser Glu Tyr Leu Gly Gln Leu Thr Asp Ile Leu
            340                 345                 350

Ser Arg Tyr Tyr Gln Leu Ala Thr Ser Phe Asp Ile Asp Val Ser Ala
        355                 360                 365

Glu Phe Lys Arg Leu Cys Val Asp Glu Ser Val Arg Ile Tyr Arg Ser
    370                 375                 380

Leu Pro Lys Asp Ser Glu Ile Lys Ser Asp Glu Glu Leu Lys Glu Ile
385                 390                 395                 400

Thr Asn Phe Val Tyr Gln Leu Ala Tyr Thr Tyr Glu Val Glu Lys Ile
                405                 410                 415

Ala Asn Val Lys Glu Ile Leu Leu Asp Pro Ala Gly Ile Leu Ile Leu
            420                 425                 430

Arg Ser Phe Ser Asn Glu Asp Phe Leu Pro Pro Ser Asp Ala Lys Ile
        435                 440                 445

Thr Leu Gln Glu Ala Ile Tyr Met Tyr Leu Arg Phe Val Thr Pro Ser
    450                 455                 460

Met Phe Ser Ala Leu Phe Glu Asn Arg Ser Ser His Asp Leu Ala Arg
465                 470                 475                 480

Thr Trp Ile Leu Phe Ala Leu Thr Asn Asn Ser Thr His Asp Leu Met
                485                 490                 495

Asp Ser Leu Lys Asp Leu Pro Ser Tyr Ile Ile Thr Val Tyr Leu Gln
            500                 505                 510

Thr Glu Leu Ile Arg Ala Cys Leu Gln Ile Asn Asp Asn Leu Arg Arg
        515                 520                 525

Thr Gln Phe Ser Ile Leu Thr Arg Ile Leu Cys Leu Leu Pro Glu Asp
    530                 535                 540

Phe Ala Phe Asn Phe Ile Arg Asp Thr Leu Leu Ser Cys Pro Tyr Glu
545                 550                 555                 560

Gln Ala Lys Cys Cys Ala Leu Ala Ile Leu Lys Asp Met Met Gln His
                565                 570                 575

Glu Arg Lys Val Pro Gln Lys Ser Asp Glu Asp Asp Leu Ala Lys Asp
```

```
            580                 585                 590

Met Glu Lys Leu Lys Ile Lys Asn Ser Pro Pro Pro Leu Pro Ser Arg
        595                 600                 605

Ala Tyr Met Leu Leu Asn Asp Asp Arg Ile Ala Thr Leu His Ser Ile
    610                 615                 620

Thr Leu Leu Ala Ile Asp Ser Cys Ala Ala Asp Pro Glu Ser Lys Lys
625                 630                 635                 640

Val Lys Thr Leu Leu Thr Tyr Leu Asn Phe Leu Asn Ala Phe Leu Thr
                645                 650                 655

Lys Trp Asp Ser Val Phe Leu Lys Glu Ile Cys Asp Ala Val Asn Asp
            660                 665                 670

Lys Leu Ile Lys Asn Glu Lys Val Gly Asp Lys Asp Glu Pro His Tyr
        675                 680                 685

Ser Leu Leu Val Ser Thr Val Ala Ser Ile Ser Ser Lys Leu
    690                 695                 700


<210> SEQ ID NO 45
<211> LENGTH: 673
<212> TYPE: PRT
<213> ORGANISM: Scheffersomyces stipitis

<400> SEQUENCE: 45

Met Ser Glu Ser Asp Val Ser Glu Asn Ser Glu Ser Thr Ile Glu Pro
1               5                   10                  15

Phe Val Phe Glu Arg Val Leu Glu Ser Leu Lys Thr Ala Ala Thr Glu
            20                  25                  30

Thr Leu Glu Ser Lys Asp Tyr Leu Ser Tyr Ser Thr Leu Leu Asp Ile
        35                  40                  45

Tyr Leu Gly Glu Pro Ala Lys Tyr Thr Tyr Asp Glu Arg Glu Glu Leu
    50                  55                  60

Leu Ser Ala Leu Leu Ser Ile Leu Ser Ala Asn Pro Gly Leu Thr Tyr
65                  70                  75                  80

Glu Ile Gly Trp Asp Leu Pro Gly Leu Leu Ile Leu Tyr Val Asp Ser
                85                  90                  95

Asp Phe Asp Phe Thr Gly Gly Leu Arg Lys Ala Pro Cys Val Tyr Lys
            100                 105                 110

Ile Leu Lys Ile Phe Glu Val Leu Ala Ile Asn Gly Asn Pro Lys Glu
        115                 120                 125

Leu Phe Leu Lys Ser Cys Glu Leu Leu Thr Thr Ile Ser Ala Asp Asp
    130                 135                 140

Ser Gln Val Thr Asp Asp Ser Ser Ile Lys Glu Lys Phe Phe Asp Val
145                 150                 155                 160

Lys Leu Tyr Cys Ile Phe Glu Leu Val Asp Ser Cys Phe Lys Arg Ile
                165                 170                 175

Lys Thr Tyr Tyr Pro Ser Arg Phe Leu Ala Met Thr Val Ala Ser Phe
            180                 185                 190

Ile Asn Leu Ala His Lys Asn Gly Asn Asp Ser Pro Asn Asn Ile Ser
        195                 200                 205

Phe Ile Met Lys Arg Ala Tyr Thr Phe Ala Arg Asn Tyr Ser Ser Pro
    210                 215                 220

Pro Leu Pro Asp Ser Asp Gly Asp Lys Met Ser Pro Glu Asp Leu Ser
225                 230                 235                 240

Lys Ile Lys Glu Asp Glu Glu Tyr Leu Gln Arg Lys Leu Leu Thr Gly
                245                 250                 255
```

```
Phe Ile Ser Gln Leu Ile Gln Leu Met Ser Asn Asp Asn Leu Asn Gly
            260                 265                 270

Tyr Thr Leu Asp His Leu Ser Phe Leu Gln Val Pro His Arg Gly Gln
        275                 280                 285

Leu Lys Lys Tyr Phe Glu Tyr Ser Val Asn Leu Pro Val Met Asp Arg
    290                 295                 300

Leu Ala Glu Leu Ala Leu Ser Tyr Asp Ile Asn Leu Thr Gln His Phe
305                 310                 315                 320

Lys Ser Met Val Ala Asp Ser His Thr Leu Leu Arg Ser Phe Asp Tyr
                325                 330                 335

Ser Ile Asp Arg Asp Glu Leu Ser Ala Gln Ile Phe Glu Lys Val Val
            340                 345                 350

Val Asp Tyr Gln Lys Thr Leu Ala Met Ser Ile Ile Asn Ser Asp Ala
        355                 360                 365

Lys Glu Ile Arg Asp Ser Pro Leu Gly Ile Phe Leu Leu Tyr Thr His
    370                 375                 380

Ala Ile Ser Val Arg Arg Thr Phe Asp Leu Ile Lys Val Ser Phe Ser
385                 390                 395                 400

Asp Ala Val Val Leu Thr Leu Arg Val Leu Val Pro Glu Leu Val Gln
                405                 410                 415

Ser Thr Phe Val Phe Lys Gly Val Glu Asp Ala Thr Ile Phe Trp Thr
            420                 425                 430

Trp Tyr Ala Leu Tyr Gln Thr Ser Leu Asn Asn Lys Ser Val Glu Thr
        435                 440                 445

Glu Ile Ala Ala Ile Ser Pro Val Leu Leu Thr Ile Tyr Tyr Gln Val
    450                 455                 460

Ile Phe Phe Val Val Ile Thr Asn Ser Asn Arg Pro Asn Phe Lys Tyr
465                 470                 475                 480

Ala Val Leu Thr Leu Leu Thr Arg Val Leu Ala Leu Ser Pro Glu Asp
                485                 490                 495

Leu Ser Tyr Asp Phe Val Lys Asp Ser Leu His Asn Cys Pro Tyr Glu
            500                 505                 510

Ser Glu Lys Pro Ile Met Ile Gly Val Leu Lys Glu Leu Leu Thr Lys
        515                 520                 525

Asp Lys Ser Ser Ser Thr Ser Asp Val Thr Glu Ala Leu Ala Asn Ser
    530                 535                 540

Glu Asp Ser Lys Val Pro Leu Pro Pro Thr Leu Pro Pro Arg Ala Ser
545                 550                 555                 560

Ser Ala Ser Ser Arg Tyr Phe Thr Leu Thr Lys Ala Arg Leu Glu Asp
                565                 570                 575

Ile Leu Ala Leu Val Gln Glu Ala Val Asp Ser Ala Phe Val Thr His
            580                 585                 590

Glu Ser Thr Val Ala Ile Asp Pro Ser Lys Leu Ser Thr Leu Ser Ala
        595                 600                 605

Tyr Leu Asn Leu Leu Val Ile Ile Lys Lys Asp Pro Val Val Leu Gln
    610                 615                 620

Asp Lys Lys Ala Leu Asp Lys Val Val Glu Ser Ala Glu Glu Asn Ile
625                 630                 635                 640

Ala Ala Val Lys Glu Lys His Lys Lys Tyr Pro Asn Ser Asn Lys Phe
                645                 650                 655

Glu Leu Asn Ala Ala Gly Ile Leu Glu Ile Thr Ile Asp Arg Ile Lys
            660                 665                 670

Ser
```

<210> SEQ ID NO 46
<211> LENGTH: 664
<212> TYPE: PRT
<213> ORGANISM: *Zygosaccharomyces rouxii*

<400> SEQUENCE: 46

```
Met Glu Asn Ile Asp Thr Val Cys Glu Asn Leu Glu Lys Ala Phe Ala
1               5                   10                  15

Glu Gln Lys Asp Asp Ser Val Thr Leu Ala Thr Ile Ile Asp Met Tyr
            20                  25                  30

Val Val Gln Ile Asn Asp Glu Gly Ser Asn Lys Asp Lys Glu Gln Phe
        35                  40                  45

Leu Thr Lys Leu Leu Asp Gln Leu Arg Ala Ser Pro Asp Ile Val Ala
    50                  55                  60

Glu Ile Gly Trp Asp Leu Pro Arg Gly Leu Leu Lys Phe Tyr Asn Lys
65                  70                  75                  80

Lys Asn Ile Asp Val Asp Ala Lys Leu Lys Ser Asn Pro Ile Val Gly
                85                  90                  95

Leu Val Met Gln Cys Phe Ser Glu Val Ala Leu Ser Gly Asn Pro Lys
            100                 105                 110

Glu Cys Leu Leu Thr Gly Cys Glu Ile Leu Ser Glu Leu Thr Thr Ile
        115                 120                 125

Gln Ile Asn Glu Gln Met Leu Glu Asp Asp Ser Lys Glu Glu Gly Asp
    130                 135                 140

Val Thr Lys Asp Glu Lys Lys Thr Asp Glu Lys Gly Glu Trp Ile Pro
145                 150                 155                 160

Glu Pro Pro His Arg Asp Pro Val Glu Phe Phe Leu Tyr Leu Asn Ser
                165                 170                 175

Tyr Val Leu Phe Glu Leu Ile Gln Thr Ala Leu Lys Arg Ile Ala Ser
            180                 185                 190

Leu Tyr Pro Ser Lys Phe Leu Gly Met Ala Val Ser Ala Ile Tyr Lys
        195                 200                 205

Phe Val Arg Asn Asn Ile Asp Glu Val Tyr Asn Thr Pro Phe Ile Leu
    210                 215                 220

Arg Arg Ile Tyr Thr Phe Cys Arg Gly Tyr Ile Pro Pro Glu Ile Pro
225                 230                 235                 240

Lys Gln Leu Leu Glu Asn Thr Lys Leu Glu Lys Lys Glu Leu Asp Lys
                245                 250                 255

Ile Thr Glu Asp Glu Ser Ile Leu Gln Gly Gln Leu Leu Arg Ser Leu
            260                 265                 270

Ser Thr Phe Ala Val Gly Glu Cys Leu Lys Asn Lys Ala Ser Arg Leu
        275                 280                 285

Asp Leu Glu Tyr Phe His Arg Leu Arg Asn Thr Glu Phe His Leu Ser
    290                 295                 300

Glu Asn Asp Glu Glu Leu Val Leu Ile Ser Lys Arg Phe Tyr Gln Leu
305                 310                 315                 320

Met Phe Ser Phe Asp Leu Asp Val Lys Glu Gln Phe Leu Ser Phe Ile
                325                 330                 335

Glu Glu Thr Lys Gly Ile Tyr Lys Ala Leu Pro Pro Asp Ser Glu Ile
            340                 345                 350

Pro Asn Asp Glu Ala Arg Arg Ala Ile Gly Gln Val Val Tyr Gln Leu
        355                 360                 365

Ser Tyr Thr Tyr Gln Leu Gln Lys Leu Thr Lys Leu Lys His Leu Glu
```

```
    370                 375                 380

Leu Asn Ser Asn Gly Ile Phe Ile Leu Ser Gly Leu His Tyr Gln Glu
385                 390                 395                 400

Thr Gln Lys His Leu Tyr Pro Glu Ile Ser Ile Lys Asp Thr Val Leu
                405                 410                 415

Leu Tyr Ile Arg Cys Ala Thr Pro Ser Leu Phe Ser Ser Thr Tyr Thr
            420                 425                 430

Asn Leu Tyr Ala Glu Gly Thr Ala Arg Tyr Trp Val Trp Val Ala Ile
        435                 440                 445

Thr Asn Asn Lys Val Gln Lys Leu Arg Glu Glu Leu Ser Glu Leu Pro
    450                 455                 460

Ser Tyr Ile Arg Thr Val Phe Leu Gln Met Val Leu Met Gln Ser Cys
465                 470                 475                 480

Asn Gln Pro Asn Glu Glu Ala Arg Met Ile Ser Phe Thr Leu Leu Thr
                485                 490                 495

Arg Ile Met Cys Leu Met Pro Glu Asp Thr Ser Phe Glu Phe Val Leu
            500                 505                 510

Asp Thr Leu Leu Thr Cys Pro Phe Thr His Ala Lys Ile Ala Val Leu
        515                 520                 525

Gly Ile Leu Lys Asp Leu Met Leu Arg Asn Cys Gln Asn Lys Gln Ser
    530                 535                 540

Leu Glu Glu Gln Phe Ser Asn Met Asn Leu Thr Ser Lys Asp Ser Asp
545                 550                 555                 560

Lys Arg Ser Thr Ser Thr Ser Pro Pro Ser Leu Pro Pro Arg Ala Tyr
                565                 570                 575

Ile Asp Ile Asn Glu Asp Arg Met Ala Ser Ile His Ser Ala Ala Met
            580                 585                 590

Met Thr Phe Gln Asp Gln Lys Ala Lys Gly Lys Asp Lys His Ile Leu
        595                 600                 605

Ile Leu Asn Phe Leu Asn Phe Phe Asn Gly Leu Ser Gln Lys Trp Asp
    610                 615                 620

Lys Asn Leu Leu Gln Ala Val His Lys Glu Val Ala Leu Gln Tyr Asn
625                 630                 635                 640

Glu Lys Thr Lys Glu Asp Val Pro Glu Val Gly Phe Ile Lys Ile Ala
                645                 650                 655

Asn Glu Thr Leu Gly Lys His Leu
            660


<210> SEQ ID NO 47
<211> LENGTH: 664
<212> TYPE: PRT
<213> ORGANISM: Candida albicans

<400> SEQUENCE: 47

Ser Glu Thr Asp His Ser Glu Thr Ser Glu Ser Thr Ile Glu Pro Phe
1               5                   10                  15

Gln Phe Glu Lys Val Met Glu Asn Leu Glu Ser Gly Ala Gln Asp Ala
            20                  25                  30

Leu Gln Ser Lys Asp Phe Leu Ser Tyr Ser Thr Leu Leu Asp Ile Tyr
        35                  40                  45

Leu Asn Asp Pro Thr Lys Tyr Ser Asn Glu Glu Lys Glu Gln Leu Leu
    50                  55                  60

Gly His Ile Leu Thr Ile Leu Ser Glu Asn Lys Gln Leu Thr Tyr Glu
65                  70                  75                  80
```

```
Ile Gly Trp Asp Leu Pro Gln Leu Leu Ile Leu Tyr Val Asp Ser Asp
                85                  90                  95

Tyr Glu Phe Asn Gly Pro Ile Arg Asp Ser Pro Gly Val Tyr Lys Ile
            100                 105                 110

Leu Lys Ile Phe Glu Asn Leu Ala Ile Asn Gly Asn His Lys Glu Leu
        115                 120                 125

Phe Leu Lys Ser Cys Glu Leu Leu Asn Asp Leu Glu Leu Ser Gln Asp
    130                 135                 140

Glu Asp Ile Glu Leu Leu Lys Arg Glu Asn Phe Phe Glu Ile Lys Leu
145                 150                 155                 160

Tyr Cys Val Phe Glu Leu Ile Asp Ala Cys Leu Lys Lys Ile His Thr
                165                 170                 175

Leu Tyr Pro Ser Arg Phe Leu Ala Met Thr Val Ser Ser Phe Asn Asn
            180                 185                 190

Leu Met Phe Lys Leu Thr Lys Gln His Gly Ser Leu Gly Asn Tyr His
        195                 200                 205

Phe Val Met Lys Arg Val Tyr Ser Phe Cys Arg Asn Tyr Ile Ser Pro
    210                 215                 220

Pro Leu Pro Thr Asn Ala Lys Glu Met Pro Gln Glu Glu Leu Asp Lys
225                 230                 235                 240

Ile Val Lys Asp Glu Glu Tyr Leu Gln Arg Arg Leu Leu Thr Gly Phe
                245                 250                 255

Leu Thr Gln Val Ile Tyr Leu Ala Asn Ile Asn Gly Thr Glu Gly Tyr
            260                 265                 270

Ser Ile Glu His Phe Ser Trp Leu Gln Gln Gln Ser Lys Ser Lys Ile
        275                 280                 285

Lys Phe Val Phe Glu Arg Asp Gly Ala Phe Cys Asp Arg Phe Val Glu
    290                 295                 300

Leu Ala Ser Ser Phe Asp Ile Asp Leu Leu Lys Cys Phe Gln Gly Phe
305                 310                 315                 320

Ile Thr Asp Ser His Lys Leu Leu Ile Gly Ile Asp Tyr Lys Asn Lys
                325                 330                 335

Asn Lys Ser Glu Asp Glu Ile Ile Glu Leu Leu Phe Glu Arg Val Val
            340                 345                 350

Val Asp Tyr Gln Lys Asn Val Leu Thr Ser Ile Val Asp Ser Asp Ala
        355                 360                 365

Lys Ala Ile Lys Asp Ser Ile Ile Gly Glu Leu Ile Leu Phe Thr His
    370                 375                 380

Ser Ile Ala Gly Lys Lys Asn Phe Ala Lys Pro Thr Met Ser Ile His
385                 390                 395                 400

Asp Ser Leu Val Met Thr Leu Arg Leu Ile Ile Pro Gln Met Val Asn
                405                 410                 415

Pro Lys Phe Ile Asn Ala Gly Asn His Asp Val Val Val Phe Trp Val
            420                 425                 430

Trp Phe Ala Leu Tyr Gln Gln Gln Ile Ile Asn Ser Lys Asn Leu Gln
        435                 440                 445

Leu Glu Ile Ser Tyr Ile Pro Lys Val Leu Leu Thr Thr Phe Phe Gln
    450                 455                 460

Cys Leu Leu Phe Ile Val Ile Lys Ser Glu Gly Lys Pro Asn Phe Lys
465                 470                 475                 480

Tyr Met Leu Leu Thr Leu Leu Thr Lys Leu Leu Thr Leu Ser Pro Asp
                485                 490                 495
```

-continued

```
Thr Gly Tyr Glu Phe Ile Lys Asp Ser Leu Asn Asn Cys Pro Tyr Glu
            500                 505                 510

Ser Val Tyr Pro Ser Leu Ile Gly Val Tyr Lys Gln Leu Leu Leu Asn
        515                 520                 525

Glu Lys Trp Asp Val Asn Ser Ile Glu Leu Glu Lys Leu Asn Ile Ser
    530                 535                 540

Ser Ser Ser Ser Asn Thr Pro Pro Lys Leu Pro Pro Arg Asn Gly Ile
545                 550                 555                 560

Lys Arg Lys His Phe Ser Leu Thr Asn Glu Ser Leu Asn Asp Leu Val
                565                 570                 575

Asp Leu Ile Asn Asn Ser Ser Lys Asn Ala Phe Val Glu Asp Asn Ser
            580                 585                 590

Lys Ile Asp Pro Ser Lys Leu Ser Thr Ile Ala Ala Tyr Leu Asn Leu
        595                 600                 605

Leu Val Ala Ile Lys Lys Asp Pro Val Ile Val Glu Asn Lys Glu Lys
    610                 615                 620

Leu Thr Thr Leu Ile Ser Ser Ile Glu Asn Lys Ile Lys Ser Val Lys
625                 630                 635                 640

Lys Ser Ser Gln Asn Gln Phe Glu Leu Asn Ala Ala Gly Met Leu Glu
                645                 650                 655

Ile Thr Ile Glu Arg Phe Asn Glu
            660
```